(12) United States Patent
McAleer et al.

(10) Patent No.: US 12,004,789 B2
(45) Date of Patent: Jun. 11, 2024

(54) DEVICES AND TECHNIQUES FOR TREATING METATARSUS ADDUCTUS

(71) Applicant: Treace Medical Concepts, Inc., Ponte Vedra, FL (US)

(72) Inventors: Jody McAleer, Jefferson City, MO (US); William DeCarbo, Pittsburgh, PA (US); Daniel Hatch, Greeley, CO (US); Paul Dayton, Ankeny, IA (US); Robert Santrock, Morgantown, WV (US); W. Bret Smith, Lexington, SC (US); Adriaan Kuyler, Ponte Vedra, FL (US); Sean Scanlan, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 411 days.

(21) Appl. No.: 17/325,167

(22) Filed: May 19, 2021

(65) Prior Publication Data
US 2021/0361330 A1 Nov. 25, 2021

Related U.S. Application Data

(60) Provisional application No. 63/126,207, filed on Dec. 16, 2020, provisional application No. 63/027,340, filed on May 19, 2020.

(51) Int. Cl.
*A61B 17/80* (2006.01)
*A61B 17/15* (2006.01)
(Continued)

(52) U.S. Cl.
CPC ...... *A61B 17/8061* (2013.01); *A61B 17/1775* (2016.11); *A61B 17/151* (2013.01);
(Continued)

(58) Field of Classification Search
CPC ............ A61B 17/8061; A61B 17/1775; A61B 17/151; A61B 17/8866; A61B 17/66;
(Continued)

(56) References Cited

U.S. PATENT DOCUMENTS 3,664,022 A 5/1972 Small
4,069,824 A 1/1978 Weinstock
(Continued)

FOREIGN PATENT DOCUMENTS

AU 2009227957 B2 7/2014
CA 2491824 A1 9/2005
(Continued)

OTHER PUBLICATIONS

Arthrex. (2018). Dorsal Midfoot Fusion Plates Surgical Techniques. https://www.arthrex.com/resources/LT1-00125-EN/dorsal-midfoot-fusion-plates ?referringteam=foot_and_ankle. (Year: 2018).*
(Continued)

*Primary Examiner* — Marcela I. Shirsat
(74) *Attorney, Agent, or Firm* — Fredrikson & Byron, P.A.

(57) ABSTRACT

A metatarsus adductus technique may involve cutting an end of one or both of a second metatarsal and an intermediate cuneiform to create a wedge-shaped opening between the end of the second metatarsal and the intermediate cuneiform. The method may further involve cutting an end of one or both of a third metatarsal and a lateral cuneiform to also create a wedge-shaped opening between the end of the third metatarsal and the lateral cuneiform. The second metatarsal and the third metatarsal can then be moved in a transverse plane to close a metatarsus adductus angle. Movement of the second and third metatarsal may close the wedge-shaped openings forming during bone cutting. With the second and third metatarsals appropriately realigned, the clinician can
(Continued)

fixate the moved position of the second metatarsal and the third metatarsal.

57 Claims, 40 Drawing Sheets

(51) Int. Cl.
*A61B 17/16* (2006.01)
*A61B 17/17* (2006.01)
*A61B 17/56* (2006.01)
*A61B 17/64* (2006.01)

(52) U.S. Cl.
CPC ......... *A61B 17/152* (2013.01); *A61B 17/1682* (2013.01); *A61B 17/1728* (2013.01); *A61B 17/1739* (2013.01); *A61B 2017/564* (2013.01); *A61B 2017/565* (2013.01); *A61B 17/6425* (2013.01)

(58) Field of Classification Search
CPC . A61B 17/848; A61B 17/152; A61B 17/1728; A61B 17/1739; A61B 17/6425; A61B 17/7291; A61B 17/8004; A61B 17/1682; A61B 17/025; A61B 2017/564; A61B 2017/565; A61B 2017/90; A61B 2017/681; A61F 2/4202
USPC ........................................................ 606/282
See application file for complete search history.

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 6,964,645 B1 | 11/2005 | Smits |
| 7,018,383 B2 | 3/2006 | McGuire |
| 7,033,361 B2 | 4/2006 | Collazo |
| 7,097,647 B2 | 8/2006 | Segler et al. |
| 7,112,204 B2 | 9/2006 | Justin et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |

(56) References Cited

U.S. PATENT DOCUMENTS

| | | |
|---|---|---|
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,518,045 B2 | 8/2013 | Szanto |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,522,023 B2 | 11/2016 | Haddad et al. |
| 9,592,084 B2 | 3/2017 | Grant |
| 9,750,538 B2 | 9/2017 | Soffiatti et al. |
| 9,785,747 B2 | 10/2017 | Geebelen |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,779,867 B2 | 9/2020 | Penzimer et al. |
| 10,939,939 B1 | 3/2021 | Gil et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde, Jr. |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |

(56) References Cited

U.S. PATENT DOCUMENTS

| | | |
|---|---|---|
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 * | 9/2014 | Dacosta ............... A61F 2/4644 623/21.19 |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0230843 A1 | 8/2015 | Palmer et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2017/0290614 A1 | 10/2017 | Weiner et al. |
| 2018/0021145 A1 | 1/2018 | Seavey et al. |
| 2018/0132868 A1 | 5/2018 | Dacosta et al. |
| 2018/0235765 A1 | 8/2018 | Welker et al. |
| 2018/0344334 A1 | 12/2018 | Kim et al. |
| 2019/0099189 A1 | 4/2019 | Fallin et al. |
| 2020/0015856 A1 | 1/2020 | Treace et al. |
| 2021/0282823 A1 * | 9/2021 | Day ............... A61B 17/8866 |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |

(56) References Cited

FOREIGN PATENT DOCUMENTS

| | | |
|---|---|---|
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | S635739 A | 1/1988 |
| JP | 2004174265 A | 6/2004 |
| JP | 2006158972 A | 6/2006 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Wienke et al., "Bone Stimulation For Nonunions: What the Evidence Reveals," Podiatry Today, vol. 24, No. 9, Sep. 2011, pp. 52-57.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Dayton et al., "A User-Friendly Method of Pin Site Management for External Fixators," Foot and Ankle Specialist, Sep. 16, 2011, 4 pages.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Dayton et al., "Principles of Management of Growth Plate Fractures in the Foot and Ankle," Clinics in Podiatric Medicine and Surgery, Pediatric Foot Deformities, Oct. 2013, 17 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Catanese et al., "Measuring Sesamoid Position in Hallux Valgus: When Is the Sesamoid Axial View Necessary," Foot and Ankle Specialist, 2014, 3 pages.

Dayton et al., "Comparison of Complications for Internal and External Fixation for Charcot Reconstruction: A Systematic Review," The Journal of Foot and Ankle Surgery, Article in Press, 2015, 4 pages.

(56) References Cited

OTHER PUBLICATIONS

Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.
Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities, Foot and Ankle International," vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Ray et al., "Hallux Valgus," Foot & Ankle Orthopaedics, vol. 4, No. 2, 2019, pp. 1-12.
Santrock et al., "Hallux Valgus Deformity and Treatment: A Three-Dimensional Approach: Lapiplasty," Foot & Ankle Clinics, vol. 23, No. 2, 2018, pp. 281-295.
Ray et al., "Multicenter Early Radiographic Outcomes of Triplanar Tarsometatarsal Arthrodesis With Early Weightbearing," Foot & Ankle International, vol. 40, No. 8, 2019, pp. 955-960.
Smith et al., "Intraoperative Multiplanar Alignment System to Guide Triplanar Correction of Hallux Valgus Deformity," Techniques in Foot & Ankle Surgery, 2017, 8 pages.
Smith et al., "Understanding Frontal Plane Correction in Hallux Valgus Repair," Clinics in Podiatric Medicine and Surgery, vol. 35, 2018, pp. 27-36.
International Patent Application No. PCT/US2021/033256, International Search Report and Written Opinion dated Sep. 7, 2021, 9 pages.
DiNapoli et al., "Metatarsal Osteotomy for the Correction of Metatarsus Adductus," Reconstructive Surgery of the Foot and Leg, 1989, pp. 242-250.
McAleer et al., "A systematic approach to the surgical correction of combined hallux valgus and metatarsus adductus deformities," The Journal of Foot & Ankle Surgery, May 21, 2021, 6 pages.
Dayton, "Tarsal-Metatarsal Joint: Primary & Revision Arthrodesis," Apr. 2014, 38 pages.
"Arthrodesis of the Tarsometatarsal Joint," Retrieved from https://musculoskeletalkey.com/arthrodesis-of-the-tarsometatarsal-joint/, posted Apr. 18, 2019, 11 pages.
Ghali et al., "The Management of Metatarsus Adductus et Supinatus," The Journal of Bone and Joint Surgery, vol. 66-B, No. 3, May 1984, pp. 376-380.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Chesser et al., "New Advances With The Tarsometatarsal Arthrodesis," Podiatry Today, vol. 30, No. 10, Sep. 27, 2017, 15 pages.
Crawford et al., "Metatarsus Adductus: Radiographic and Pathomechanical Analysis," Chapter 5, 2014, 6 pages.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.

(56) References Cited

OTHER PUBLICATIONS

Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpgloballearhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide To The Lapidus Bunionectomy," Podiatry Today, Retrieved online from <https://www.hmpgloballearningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus," The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).

(56) References Cited

OTHER PUBLICATIONS

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Coetzee et al., "The Lapidus Procedure: A Prospective Cohort Outcome Study," Foot & Ankle International, vol. 25, No. 8, Aug. 2004, pp. 526-531.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
"Futura Forefoot Implant Arthroplasty Products," Tornier, Inc., 2008, 14 pages.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"Hat-Trick Lesser Toe Repair System," Smith & Nephew, Brochure, Aug. 2014, 12 pages.
"Hat-Trick Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.

(56) References Cited

OTHER PUBLICATIONS

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a Hat-Trick with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weber et al., "A Simple System For Navigation Of Bone Alignment Osteotomies Of The Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Conti et al., "Effect of the Modified Lapidus Procedure for Hallux Valgus on Foot Width," Foot & Ankle International, Feb. 1, 2020, published online: Oct. 30, 2019, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

(56) References Cited

OTHER PUBLICATIONS

Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Dayton et al., "Comparison of Radiographic Measurements Before and After Triplane Tarsometatarsal Arthrodesis for Hallux Valgus," The Journal of Foot & Ankle Surgery, vol. 59, 2020, pp. 291-297.
Dayton et al., "Evidence-Based Bunion Surgery: A Critical Examination of Current and Emerging Concepts and Techniques," Springer International Publishing, 2017, 254 pages.
Dayton et al., "Comparison of Tibial Sesamoid Position on Anteroposterior and Axial Radiographs Before and After Triplane Tarsal Metatarsal Joint Arthrodesis," The Journal of Foot & Ankle Surgery, vol. 56, 2017, pp. 1041-1046.
Dayton et al., "Biomechanical Characteristics of Biplane Multiplanar Tension-Side Fixation for Lapidus Fusion," The Journal of Foot & Ankle Surgery, vol. 57, 2018, pp. 761-765.
Dayton et al., "Progression of Healing on Serial Radiographs Following First Ray Arthrodesis in the Foot Using a Biplanar Plating Technique Without Compression," The Journal of Foot & Ankle Surgery, 2018, 7 pages.
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
Aiyer et al., "Prevalence of Metatarsus Adductus in Patients Undergoing Hallux Valgus Surgery," Foot & Ankle International, vol. 35, No. 12, 2014, pp. 1292-1297.
Bennett et al., "Intraosseous Sliding Plate Fixation Used in Double Osteotomy Bunionectomy," Foot & Ankle International, vol. 40, No. 1, 2019, pp. 85-88.
Buda et al., "Effect of Fixation Type and Bone Graft on Tarsometatarsal Fusion," Foot & Ankle International, vol. 39, No. 12, 2018, pp. 1394-1402.
Chomej et al., "Lateralising DMMO (MIS) for simultaneous correction of a pes adductus during surgical treatment of a hallux valgus," The Foot, vol. 45, Dec. 2020, 33 pages.
Cichero et al., "Different fixation constructs and the risk of nonunion following first metatarsophalangeal joint arthrodesis," Foot and Ankle Surgery, vol. 27, 2021, pp. 789-792.
Curran et al., "Functional Capabilities After First Metatarsal Phalangeal Joint Arthrodesis Using a Locking Plate and Compression Screw Construct," The Journal of Foot & Ankle Surgery, vol. 61, No. 1, Jan./Feb. 2022, pp. 79-83.
Dalat et al., "Does arthrodesis of the first metatarsophalangeal joint correct the intermetatarsal M1M2 angle? Analysis of a continuous series of 208 arthrodeses fixed with plates," Orthopaedics & Traumatology: Surgery & Research, vol. 101, 2015, pp. 709-714.
DeHeer et al., "Procedure-Specific Hardware Removal After Evans Osteotomy," Journal of the American Podiatric Medical Association, vol. 110, No. 2, Mar./Apr. 2020, 7 pages.
Fazal et al., "First metatarsophalangeal joint arthrodesis with two orthogonal two hole plates," Acta Orthopaedica et Traumatologica Turcica, vol. 52, 2018, pp. 363-366.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fraissler et al., "Treatment of hallux valgus deformity," Efort Open Reviews, vol. 1, Aug. 2016, pp. 295-302.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Ho et al., "Hallux rigidus," Efort Open Reviews, vol. 2, Jan. 2017, pp. 13-20.
Hunt et al., "Locked Versus Nonlocked Plate Fixation For Hallux MTP Arthrodesis," Foot and Ankle International, vol. 32, No. 7, Jul. 2011, pp. 704-709.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
Kurup et al., "Midfoot arthritis—current concepts review," Journal of Clinical Orthopaedics and Trauma, vol. 11, 2020, pp. 399-405.
La Reaux et al., "Metatarsus adductus and hallux abducto valgus: their correlation," The Journal of Foot Surgery, vol. 26, No. 4, Jul. 1987, pp. 304-308, Abstract Only.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Little, "Joint Arthrodesis For Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.
Machacek Jr. et al., "Salvage of a Failed Keller Resection Arthroplasty," The Journal of Bone and Joint Surgery, vol. 86A, No. 6, Jun. 2004, pp. 1131-1138.
Marshall et al., "The identification and appraisal of assessment tools used to evaluate metatarsus adductus: a systematic review of their measurement properties," Journal of Foot and Ankle Research, vol. 11, No. 25, 2018, 10 pages.
McAleer et al., "Radiographic Outcomes Following Triplanar Correction of Combined Hallux Valgus and Metatarsus Adductus Deformities," ACFAS Scientific Conference, Poster, Feb. 2022, 1 page.
McCabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Miller et al., "Variable Angle Locking Compression Plate as Alternative Fixation for Jones Fractures: A Case Series," Kansas Journal of Medicine, vol. 12, No. 2, May 2019, pp. 28-32.
Nix et al., "Prevalence of hallux valgus in the general population: a systematic review and meta-analysis," Journal of Foot and Ankle Research, vol. 3, No. 21, 2010, 9 pages.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.

(56) References Cited

OTHER PUBLICATIONS

Shima et al., "Operative Treatment for Hallux Valgus With Moderate to Severe Metatarsus Adductus," Foot & Ankle International, vol. 40, No. 6, 2019, pp. 641-647.

Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.

Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.

Williams et al., "Metatarsus adductus: Development of a non-surgical treatment pathway," Journal of Paediatrics and Child Health, vol. 49, 2013, pp. E428-E433.

\* cited by examiner

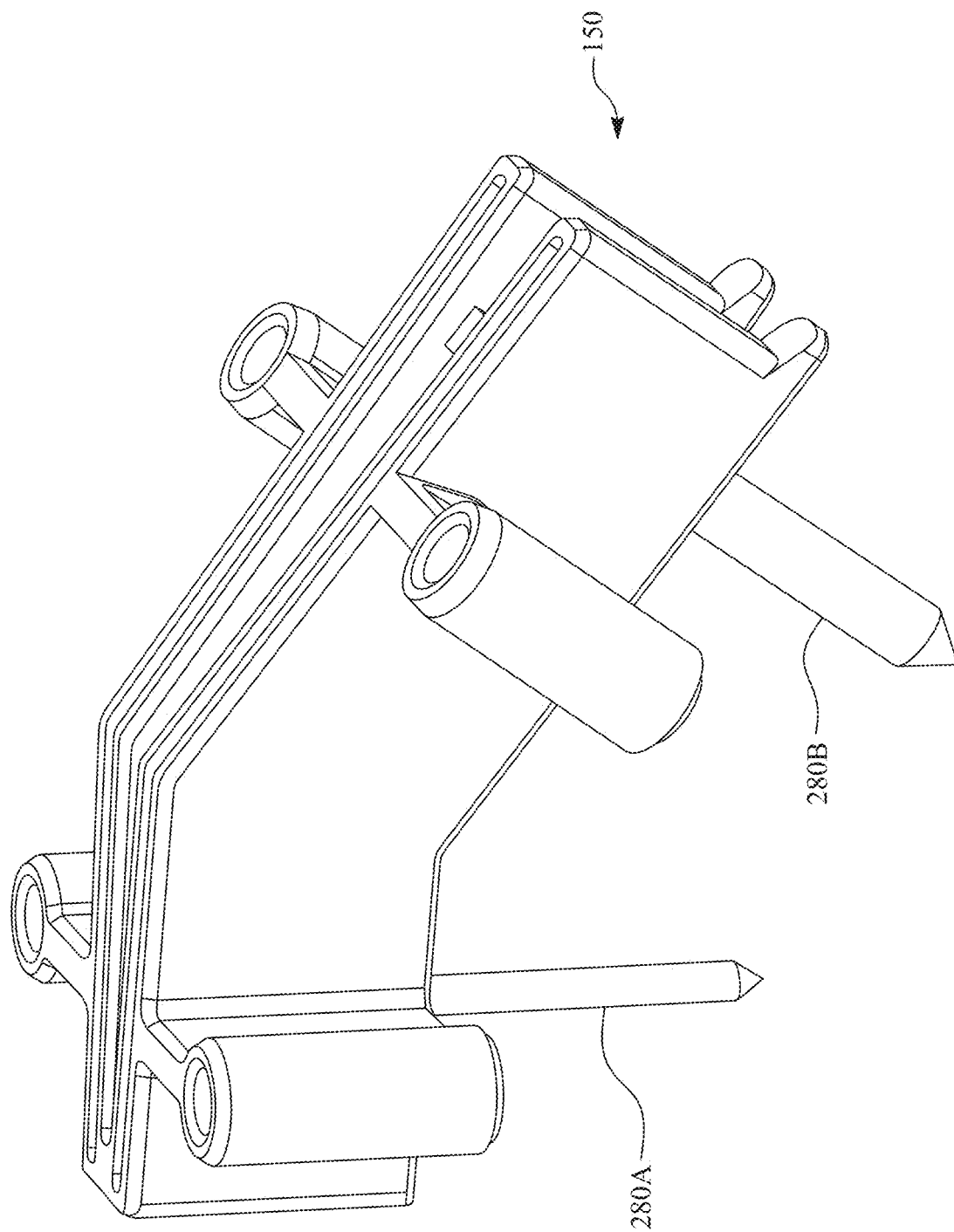

Medial corner of M2 base
And intermediate cuneiform

2nd TMT Joint

3rd TMT Joint

2nd and 3rd TMT Joint
Combined reference

Space between
M2 and M3 base
(corner)

DEVICES AND TECHNIQUES FOR TREATING METATARSUS ADDUCTUS

CROSS REFERENCE

This application claims the benefit of U.S. Provisional Patent Application No. 63/027,340, filed May 19, 2020, and U.S. Provisional Patent Application No. 63/126,207, filed Dec. 16, 2020, the entire contents of each of which are incorporated herein by reference.

TECHNICAL FIELD

This disclosure relates to devices and techniques for treating metatarsus adductus.

BACKGROUND

Metatarsus adductus (MTA) is a deformity of the foot in which the metatarsals are angulated into adduction. MTA is typically characterized by a medial deviation of the metatarsals in the transverse plane. For example, MTA is often described as a structural deformity occurring at the Lisfranc joint (tarsometatarsal joints), with the metatarsals being deviated medially with reference to the lesser tarsus.

In some patients, MTA presents with hallux valgus, also referred to as hallux abducto valgus. Hallux valgus is a complex progressive condition that is characterized by lateral deviation (valgus, abduction) of the hallux and medial deviation of the first metatarsophalangeal joint. Hallux valgus typically results in an increase in the hallux adductus angle, which is the angle between the long axes of the first metatarsal and proximal phalanx in the transverse plane.

In some cases, surgical intervention is needed to address MTA and/or hallux valgus deformities. Surgical intervention may involve realigning one or more bones of the foot, improving patient comfort and increasing patient mobility.

SUMMARY

In general, this disclosure is directed to devices and techniques for treating metatarsus adductus (MTA), either alone or in combination with treatment of hallux valgus. In some implementations, a clinician surgically accesses the second and third tarsometatarsal joints of the foot to prepare the joints for realignment and fusion. The clinician may make an incision, e.g., providing dorsolateral and dorsomedial access, to the second and third tarsometatarsal joints. With the joints exposed, the clinician may prepare the end faces of the second and third metatarsals and opposed intermediate and lateral cuneiforms, respectively. With or without the use of a cut guide, the clinician may cut an end of at least one of the bones forming the second tarsometatarsal joint and also cut an end of at least one of the bones forming the third tarsometatarsal joint. The cut may be angled relative to an end face of the bone being cut so as to define an opening between the two bones, such as a wedge expanding from a narrow end (e.g., apex) to a wider end (e.g., base). Once the bone slice (e.g., wedge) is removed from the joint space, a gap (e.g., wedge-shaped gap) may exist between the end of the metatarsal and opposed cuneiform. For example, the narrower portion of the wedge may be on the medial side of the joint while the wider portion of the wedge may be on the lateral side of the joint. The metatarsal can be rotated in at least the transverse plane, with or without the use of a bone positioning guide, to close the wedge-shaped gap formed by cutting and removing the bone wedge. For example, the metatarsal may be moved in the transverse plane, rotated in the frontal plane, and/or moved in the sagittal plane to realign the metatarsal. This can help realign the bone to correct the metatarsal adductus deformity (or other bone condition being treated).

In some implementations, the second and third tarsometatarsal joints are prepared and the second and third metatarsals independently moved from each other in one or more planes, such as the transverse plane. In other implementations, the second and third tarsometatarsal joints can be prepared and the second and third metatarsals move together to address the angular misalignment of the metatarsals. For example, when accessing and preparing the second and third tarsometatarsal joints, the plantar tarsometatarsal ligaments and the ligaments between the second and third metatarsals may be preserved (e.g., remain uncut or unbroken). This can maintain the connective tissue between the second and third metatarsals, allowing the second and third metatarsals to be manipulated as an interconnected block or group during angular realignment.

For instance, in one implementation, the clinician may access the second and third tarsometatarsal joints and then prepare the ends of the second and third metatarsals as well as the ends of the intermediate and lateral cuneiforms. The clinician may cut an end of at least one of the second metatarsal and the intermediate cuneiform, e.g., to define a wedge-shaped opening between two bone faces. The clinician may also cut an end of at least one of the third metatarsal and the lateral cuneiform, e.g., to define a wedge-shaped opening between two bone faces. The clinician can then move the second and third metatarsals together, e.g., by applying a force to the second metatarsal alone, applying a force to the third metatarsal alone, or by applying a force to both the second and third metatarsals. In any case, the distal ends of the second and third metatarsals can move laterally in at least the transverse plane while the proximal ends of the second and third metatarsals pivot to close the opening (e.g., wedge-shaped gap) formed during bone preparation. The Lisfranc ligament may serve as a tethering point at the base of the second metatarsal around which rotation of the second and third metatarsals occurs. In some implementations, a soft tissue release is performed between the third and fourth metatarsals to help mobilize the third metatarsal and allow reorientation.

In addition to realigning the second and third metatarsals, the fourth and fifth metatarsals may also be realigned to help correct the metatarsal adductus. The distal ends of the fourth and fifth metatarsals may naturally pivot laterally in the transverse plane upon forcible movement of the second and/or third metatarsals. For example, when the second and third metatarsals are moved individually or as an interconnected block, rotation of the metatarsals may cause natural realignment (e.g., lateral pivoting of the distal ends) of the fourth and fifth metatarsals in at least the transverse plane. The force applied to the second and third metatarsals may translate through tissue (e.g., one or more ligaments) interconnecting the second and third metatarsals with the fourth and fifth metatarsals. In different implementations, the fourth and/or fifth tarsometatarsal joints may or may not be surgically accessed and prepared for fusion (e.g., by preparing the end of the fourth and/or fifth metatarsal and/or preparing the end of the cuboid bone opposite the metatarsal for fusion). Realignment of one or more lesser metatarsals also results in realignment of a remainder of the digit, e.g., the proximal phalanx and other interconnected bones.

With one or more lesser metatarsals realigned in one or more planes (e.g., at least the transverse plane), the clinician can fixate the moved position of the one or more metatarsals. In some examples, the clinician may provisionally fixate one or more moved metatarsals before permanently fixating the moved position. For example, the clinician may insert a fixation pin through the second metatarsal into another bone such as the lateral cuneiform and/or insert a fixation pin through the third metatarsal into another bone such as the intermediate cuneiform. With or without provisional fixation, the clinician may permanently fixate a moved bone position, e.g., by applying a fixation device across the second tarsometatarsal joint and/or across the third tarsometatarsal joint.

While a surgical technique according to the disclosure may involve surgically accessing and preparing multiple lesser tarsometatarsal joints of the foot, such as the second and third tarsometatarsal joints as discussed above, in alternative implementations a technique can be performed on a single lesser tarsometatarsal joint (e.g., the second tarsometatarsal joint, the third tarsometatarsal joint, the fourth tarsometatarsal joint, and/or the fifth tarsometatarsal joint). This procedure on the single lesser tarsometatarsal joint may be performed either alone or in combination with treatment of hallux valgus on the first metatarsal. For example, a MTA deformity or other bone deformity may be corrected by operating on a single lesser tarsometatarsal joint (e.g., the second tarsometatarsal joint, the third tarsometatarsal joint) without operating on other lesser tarsometatarsal joints, again optionally with alignment correction of the first metatarsal through a procedure performed on the first tarsometatarsal joint.

For example, the surgeon may access the second tarsometatarsal joint, the third tarsometatarsal joint, or yet other lesser tarsometatarsal joint. The surgeon can prepare the end of the metatarsal (e.g., second metatarsal, third metatarsal) and/or the end of the bone on the other side of the joint (e.g., intermediate cuneiform, lateral cuneiform). In some examples, the clinician cuts the end of each of the bones separated by the tarsometatarsal joint. The clinician can then apply a force to one or more of the lesser metatarsals (e.g., the metatarsal with prepared end, an adjacent metatarsal with unprepared end). The force may move the metatarsal in one or more planes, such as the transverse plane and/or frontal plane, to realign the metatarsal. In some implementations, the force moves substantially only the lesser metatarsal being surgically accessed and operated on to realign the lesser metatarsal. In other examples, the force moves the lesser metatarsal being surgically accessed and operated on and one or more (e.g., all) other adjacent and/or lesser metatarsals to realign multiple bones in the foot.

In situations where the patient also presents with a first metatarsal angular deformity such as hallux valgus, the clinician may also perform a first metatarsal realignment. The first metatarsal realignment may be performed before or after realignment of a lesser metatarsal (second, third, fourth, and/or fifth metatarsals) or may be performed at least partially concurrent with the process of realigning the lesser metatarsal. For example, the clinician may realign the lesser metatarsals and, before or after fixating the moved position of the realigned lesser metatarsals, realign the first metatarsal in one or more planes.

To realign the first metatarsal, the clinician may perform an incision across the first tarsometatarsal joint to access the joint. With the joint exposed, the clinician may prepare the end of the first metatarsal and also prepare the opposed end of the medial cuneiform. Before or after preparing one or both bone ends, the clinician can move the first metatarsal in one or more planes. For example the clinician may pivot the distal end of the first metatarsal in the transverse plane to close an intermetatarsal angle between the first and second metatarsals. Additionally or alternatively, the clinician may rotate the first metatarsal in the frontal plane and/or adjust the angular alignment of the first metatarsal in the sagittal plane. With the first metatarsal suitably realigned, the clinician can fixate the moved position of the first metatarsal.

Independent of the specific surgical technique performed during a treatment procedure, a variety of different instruments may be provided to help facilitate bone preparation and/or realignment techniques. The instruments may be utilized as part of a metatarsal adductus treatment procedure or yet other treatment procedure (e.g., fusion of an arthritic joint, realignment of a bone other than a metatarsal). For example, a bone cutting guide may be used to help cut an end face of a metatarsal and/or cuneiform to facilitate realignment and/or fusion between bones. In general, the bone cutting guide may be sized and shaped to be positioned over one or more bones to be cut. The bone cutting guide may define at least one guide surface along which a cutting instrument can be guided to cut a bone in a plane parallel to the guide surface. For example, the bone cutting guide may define a pair of guide surfaces defining a cutting slot there between through which a cutting instrument can be inserted.

In some examples, a bone cutting guide defines a guide surface configured to be positioned on a dorsal side of a metatarsal and/or cuneiform (or cuboid) to be cut. The bone cutting guide may include a locating feature (e.g., a spacer or pin) that can be inserted in a joint space between adjacent bones and/or into a bone, respectively, to help position the guide surface over the bone to be cut. The spacer or pin may be fixedly (e.g., non-movably) connected to the guide surface or may be movable relative to the guide surface. For example, when the spacer or pin is movable relative to the guide surface, the spacer or pin may be inserted into a joint space or inserted into a bone and the structure defining the guide surface then inserted down over the spacer or pin or otherwise attached to the spacer or pin (e.g., via a clamp, pin, screw, or other attachment mechanism). In some configurations, the guide surface can rotate about the spacer or pin, for example within a restricted angular range of travel, to allow the clinician to adjust the positioning of the guide surface over the bone to be cut by rotating the guide surface about the pin or spacer. Once suitably positioned, one or more other fixation pins may optionally be used to lock the position of the cut guide relative to the bone to be cut.

A bone cutting guide configured for a surgical procedure (e.g., metatarsal adductus procedure) may have a guide surface for guiding cutting of a single bone or may be configured to guide a cutting instrument to cut multiple different bones. For example, the bone cutting guide may include at least one guide surface (e.g., at least one cutting slot) to guide a cutting instrument to cut an end of a metatarsal and at least one additional guide surface (e.g., at least one additional cutting slot) to guide a cutting instrument to cut an end of an opposed cuneiform. The guide surfaces may be angled relative to each other, e.g., with the angle opening toward the lateral side of the foot, when the cutting guide is installed on the foot. The angle between the guide surfaces may be fixed or may be adjustable. When configured with an adjustable angle, the clinician may adjust the angle between one guide surface positionable over a metatarsal to be cut in another guide surface positionable over an opposed bone (e.g., cuneiform) to be cut.

When the intermediate and lateral cuneiforms opposing the second and third metatarsals, respectively, are prepared through cutting, the cuneiforms may be cut individually or may be cut together. In one implementation, for example, a cut guide may be used that has an elongated guide surface configured to extend over both the intermediate cuneiform and the lateral cuneiform. The guide surface may be parallel to an adjacent guide surface to define a cutting slot. The cutting slot may be positionable on a dorsal side of the intermediate and lateral cuneiforms, extending from at least the medial side of the intermediate cuneiform to the lateral side of the lateral cuneiform. When so configured, a clinician may guide a cutting instrument along the guide surface (e.g., through the cutting slot) to cut both the intermediate cuneiform and the lateral cuneiform. This can result in the intermediate cuneiform and the lateral cuneiform having parallel cut end faces, which can help realignment to close the metatarsal adductus angle.

In addition to or in lieu of using a bone cutting guide, a bone preparation template may be provided that the surgeon can overlay on one or more bones to be prepared to mark locations for preforming a subsequent bone preparation step. The bone preparation template may include one or more orienting features relative to one or more underlying bones (e.g., a metatarsal, cuneiform, and/or joint line) indicating one or more locations where the bones should be cut or otherwise prepared. The surgeon may use the bone preparation template to impart indicia on one or more underlying bones where preparation should occur. The surgeon may subsequently perform guided and/or freehand bone preparation (optionally removing the bone preparation template beforehand) to prepare the one or more bones at the location marked using the bone preparation template. The surgeon may move and/or fixate one or more bones as discussed in conjunction with the use of a bone cutting guide.

In one example, a method for treating metatarsus adductus is described. The method includes cutting an end of at least one of a second metatarsal and an intermediate cuneiform to create a wedge-shaped opening between the end of the second metatarsal and the intermediate cuneiform. The method also involves preparing an end of the other of the second metatarsal and intermediate cuneiform. The method further includes cutting an end of at least one of a third metatarsal and a lateral cuneiform to create a wedge-shaped opening between the end of the third metatarsal and the lateral cuneiform. The method also involves moving the second metatarsal and the third metatarsal in a transverse plane to close a metatarsus adductus angle. The method also specifies fixating a moved position of the second metatarsal and the third metatarsal.

In another example, a method for treating metatarsus adductus is described. The method includes positioning a cuneiform-side guide surface of a cutting guide over a dorsal side of an intermediate cuneiform and over a dorsal side of a lateral cuneiform and positioning a metatarsal-side guide surface of the cutting guide over a dorsal side of a second metatarsal facing the intermediate cuneiform and over a dorsal side of a third metatarsal facing the lateral cuneiform. The method involves using the cuneiform-side guide surface to advance a cutting tool in a plane parallel to the cuneiform-side guide surface to remove a portion of the intermediate cuneiform and to remove a portion of the lateral cuneiform and using the metatarsal-side guide surface to advance the cutting tool in a plane parallel to the metatarsal-side guide surface to remove a portion of the second metatarsal and to remove a portion of the third metatarsal. The method includes moving the second metatarsal and the third metatarsal in a transverse plane to close a metatarsus adductus angle and fixating the moved position of the second metatarsal and the third metatarsal.

In another example, a bone cutting guide for use in a metatarsus adductus procedure is described. The bone cutting guide may include a cuneiform-side guide surface configured to be positioned over a dorsal side of both an intermediate cuneiform and a lateral cuneiform of a foot with the cuneiform-side guide surface being configured to guide a cutting instrument to cut the intermediate cuneiform and the lateral cuneiform. The bone cutting guide may also included a metatarsal-side guide surface configured to be positioned over a dorsal side of both a second metatarsal and a third metatarsal of the foot with the metatarsal-side guide surface being configured to guide the cutting instrument to cut the second metatarsal and the third metatarsal. According to the example, the cuneiform-side guide surface and the metatarsal-side guide surface are each spaced from each other by a distance configured to cross a second metatarsal joint between the intermediate cuneiform and the second metatarsal and a third metatarsal joint between the lateral cuneiform and the third metatarsal.

In some aspects of the example, the cuneiform-side guide surface includes a continuous cuneiform-side guide surface configured to extend from a medial-most side of the intermediate cuneiform to a lateral-most side of the lateral cuneiform. In some aspects of the example, the metatarsal-side guide surface includes a continuous metatarsal-side guide surface configured to extend from a medial-most side of the second metatarsal to a lateral-most side of the third metatarsal. In some aspects of the example, the metatarsal-side guide surface includes a first cuneiform-side guide surface configured to extend across the second metatarsal and a second cuneiform-side guide surface configured to extend across the third metatarsal.

In some aspects of the example, the cuneiform-side guide surface defines a first cuneiform-side guide surface and further includes a second cuneiform-side guide surface parallel to the first cuneiform-side guide surface to define a cuneiform-side cutting slot therebetween. Additionally, the metatarsal-side guide surface defines a first metatarsal-side guide surface and further includes a second metatarsal-side guide surface parallel to the first metatarsal-side guide surface to define a metatarsal-side cutting slot therebetween.

In some aspects of the example, an angle between the cuneiform-side guide surface and the metatarsal-side guide surface is fixed. In other aspects of the example, the angle between the cuneiform-side guide surface and the metatarsal-side guide surface is adjustable. In some aspects of this example, the bone cutting guide further includes a lock configured to lock the adjustable angle. In some aspects of the example, an angle between the cuneiform-side guide surface and the metatarsal-side guide surface is within a range from 1 degree to 40 degrees, such as from 5 degrees to 20 degrees.

In some aspects of the example, the bone cutting guide further includes at least one locating feature associated with the bone cutting guide, where the at least one locating feature is configured to be inserted into at least one of a bone and a joint between adjacent bones to position the bone cutting guide. In some aspects of the example, the locating feature includes a spacer configured to be positioned at least partially within both the second metatarsal joint and the third metatarsal joint and bridging between the second metatarsal joint and the third metatarsal. In some aspects of the example, the spacer tapers in a dorsal to plantar direction along its length.

In some aspects of the example, the bone cutting guide further includes at least one fixation hole configured to receive a fixation pin for pinning the bone cutting guide to an underlying bone, the at least one fixation hole being adjustable in at least one dimension. In some aspects of the example, the fixation hole is adjustable along a length of the bone cutting guide.

In another example, a bone cutting guide is described that includes a cuneiform-side guide surface configured to be positioned over at least one cuneiform of a foot with the cuneiform-side guide surface being configured to guide a cutting instrument to cut the at least one of cuneiform. The bone cutting guide also includes a metatarsal-side guide surface configured to be positioned over at least one metatarsal with the metatarsal-side guide surface being configured to guide the cutting instrument to cut the at least one metatarsal. The example bone cutting guide also includes at least one fixation hole configured to receive a fixation pin for pinning the bone cutting guide to an underlying bone that is adjustable in at least one dimension. In some aspects of the example, the fixation hole is adjustable along a length of the bone cutting guide. In some aspects of the example, the fixation hole is rotationally adjustable relative to bone cutting guide.

The details of one or more examples are set forth in the accompanying drawings and the description below. Other features, objects, and advantages will be apparent from the description and drawings, and from the claims.

BRIEF DESCRIPTION OF DRAWINGS

FIG. 22 is a perspective view of an example cut guide having two associated locating features.

DETAILED DESCRIPTION

Figure 1B:
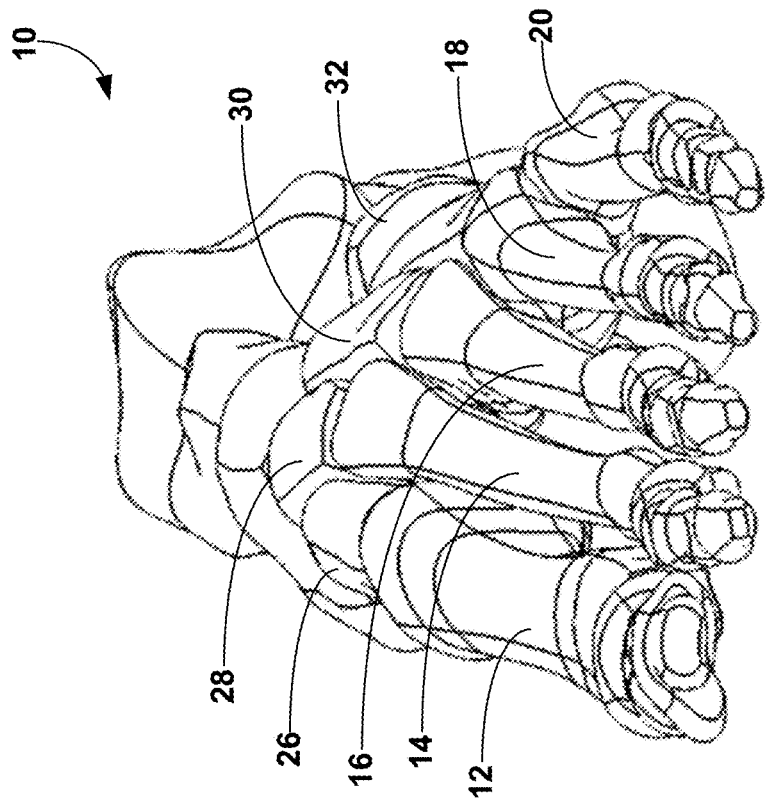
FIGS. 1A and 1B are top and front views, respectively, of a foot showing normal metatarsal alignment positions.

In general, the present disclosure is directed to devices and techniques for preparing one or more tarsometatarsal joints ("TMT joint") for fusion and realigning one or more metatarsals separated from an opposed bone by the tarsometatarsal joint. While a technique according to disclosure can be performed on any TMT joint, in some implementations, a surgical technique is performed on at least the second TMT joint and the third TMT joint. During the procedure, the clinician may cut an end of one or both of the second metatarsal and opposed intermediate cuneiform. Additionally or alternatively, the clinician may cut an end of one or both of the third metatarsal and opposed lateral cuneiform. In some examples the clinician advances a cutting instrument along a path (e.g., a linear path and/or a curved path) to cut one metatarsal end followed by another metatarsal end and/or to cut one cuneiform end followed by another cuneiform end. In either case, a bone portion may be removed from the TMT joint space, such as between both the second TMT joint space and the third TMT joint space. The bone portion and/or space from which the bone portion is removed may be shaped to facilitate subsequent repositioning of the metatarsal relative to the opposed cuneiform, e.g., by moving the metatarsal to partially or fully close the space created upon removal of the bone portion.

Independent of how one or more TMT joints are prepared, the clinician can apply a force to one or more metatarsals, such as the second and/or third metatarsals, to rotate the one or more metatarsals in at least one plane (e.g., one or more of the transverse plane, frontal plane, and/or sagittal plane). When repositioning both the second and third metatarsals, the second and third metatarsals may or may not remain interconnected through ligamentous attachments, such as the plantar ligaments and/or second-to-third intermetatarsal ligaments. When remaining interconnected, the second and third metatarsals may be pivoted together as a block (e.g., in at least one plane, such as the transverse plane). For example, the second and third metatarsals may pivot generally about a medial aspect (e.g., side) of the second TMT joint in the transverse plane, closing a larger opening on the lateral side of the joint. In some implementations, the second and/or third metatarsals may be pivoted in at least the transverse plane with the second metatarsal base being attached to the Lisfranc ligament to serve as a pivot point about which the bone block can rotate. The clinician can pivot the second and third metatarsals by hand and/or with the aid of a bone positioner that engages with at least one of the second and third metatarsals and a bone other than that with which the bone positioner is engaged.

The fourth and fifth metatarsals may also be pivot in one or more planes (e.g., at least the transverse plane), such as concurrent with the second and/or third metatarsals being pivoted in one or more planes. The fourth and fifth metatarsals may realign without accessing or preparing the fourth or fifth TMT joints. That being said, in some examples, the fourth and/or fifth metatarsals may be surgically accessed and prepared by prepared an end of the fourth metatarsal and/or opposed cuboid bone and/or an end of the fifth metatarsal and/or opposed cuboid bone. After suitably realigning one or more of the second, third, fourth and/or fifth metatarsals, the moved position of the one or more metatarsals may be fixated. In some examples, a provisional fixation step is performed in which one or more temporary fixation pins are deployed to hold the moved position of one or more metatarsals (e.g., by inserting the fixation pin through one or more moved metatarsal and into one or more adjacent bones). A permanent fixation device can be used to hold a moved position of a bone for subsequent fusion. Example permanent fixation devices include, but are not limited to, pins (e.g., intramedullary nail, K-wire, Steinmann pin), plates, screws, staples, and combinations.

Before, after, or concurrent with preparing and moving one or more lesser metatarsals (e.g., one or more of the second, third, fourth, and/or fifth metatarsals), the clinician may prepare and move the first metatarsal. The clinician may prepare the end of the first metatarsal and also prepare the opposed end of the medial cuneiform. Before or after preparing one or both bone ends, the clinician can move the first metatarsal in one or more planes. For example the clinician may pivot the distal end of the first metatarsal in the transverse plane to close an intermetatarsal angle between the first and second metatarsals. Additionally or alternatively, the clinician may rotate the first metatarsal in the frontal plane and/or adjust the angular alignment of the first metatarsal in the sagittal plane. With the first metatarsal suitably realigned, the clinician can fixate the moved position of the first metatarsal. Details on example first metatarsal realignment instruments and techniques that can be used in conjunction with the present disclosure are described in U.S. Pat. No. 9,622,805, issued Apr. 18, 2017 and entitled "BONE POSITIONING AND PREPARING GUIDE SYSTEMS AND METHODS," U.S. Pat. No. 10,245,088, issued Apr. 2, 2019 and entitled "BONE PLATING SYSTEM AND METHOD," US Patent Publication No. 2020/0015856, published Jan. 16, 2020 and entitled "COMPRESSOR-DISTRACTOR FOR ANGULARLY REALIGNING BONE PORTIONS," and US Patent Publication No. 2020/0015870, published Jan. 16, 2020 and entitled "MULTI-DIAMETER BONE PIN FOR INSTALLING AND ALIGNING BONE FIXATION PLATE WHILE MINIMIZING BONE DAMAGE." The entire contents of each of these patent documents are incorporated herein by reference.

Preparation and fusion of one or more TMT joints may be performed according to the disclosure for a variety of clinical reasons and indications. Preparation and fusion of a TMT joint may be performed to treat metatarsus adductus, hallux valgus, and/or other bone and/or joint conditions.

Metatarsus adductus is a deformity of the foot characterized by a transverse plane deformity where the metatarsals are adducted at the Lisfranc joint. The extent of a metatarsus adductus deformity can be characterized by a metatarsus adductus angle. The metatarsus adductus angle can be defined as the angle between the longitudinal axis of the second metatarsal (representing the longitudinal axis of the metatarsus) and the longitudinal axis of the lesser tarsus. The measurement of the longitudinal axis of the lesser tarsus can be characterized by a line perpendicular to the transverse axis of the lesser tarsus using the lateral joint of the fourth metatarsal with the cuboid as a reference.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux adductus angle, the angle between the long axes of the first metatarsal and proximal phalanx in the transverse plane. An increase in the hallux adductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the crista of the first metatarsal head.

While techniques and devices are described herein particularly in connection with TMT joints of the foot, the techniques and/or devices may be used on other similar bones separated by a joint in the hand or foot. For example, the techniques and devices may be performed on the carpometacarpal joints of the hand. As another example, one or more techniques and/or devices may be used on a metatarsal and/or phalanx, e.g., across a metatarsophalangeal joint. In various implementations, the devices and/or techniques can be used as part of a bone alignment, osteotomy, fusion, fracture repair, and/or other procedure where one or more bones are to be prepared and/or moved to a desired position.

Further, while the techniques and devices described herein are generally discussed in connection with preparation and fusion of the second and/or third TMT joints, the devices and techniques are not limited to these specific anatomical locations or being performed together. In various examples, devices and/or techniques of the disclosure may be utilized to prepare and promote fusion across a single TMT joint (e.g., the first TMT joint the second TMT joint, the third TMT joint, the fourth TMT joint, the fifth TMT joint) and/or any combination of TMT joints (e.g., the first and second TMT joints; the second and third TMT joints; the first and third TMT joints; the first, second, and third TMT joints; the first and fourth TMT joints; the first, second, and fourth TMT joints, etc.).

To further understand example techniques of the disclosure, the anatomy of the foot will first be described with respect to FIGS. 1-3 along with example misalignments that may occur and be corrected according to the present disclosure. As noted, a bone misalignment may be caused by metatarsus adductus, hallux valgus (bunion), and/or other condition. The condition may present with a misalignment of one or more bones in the foot.

Figure 1A:
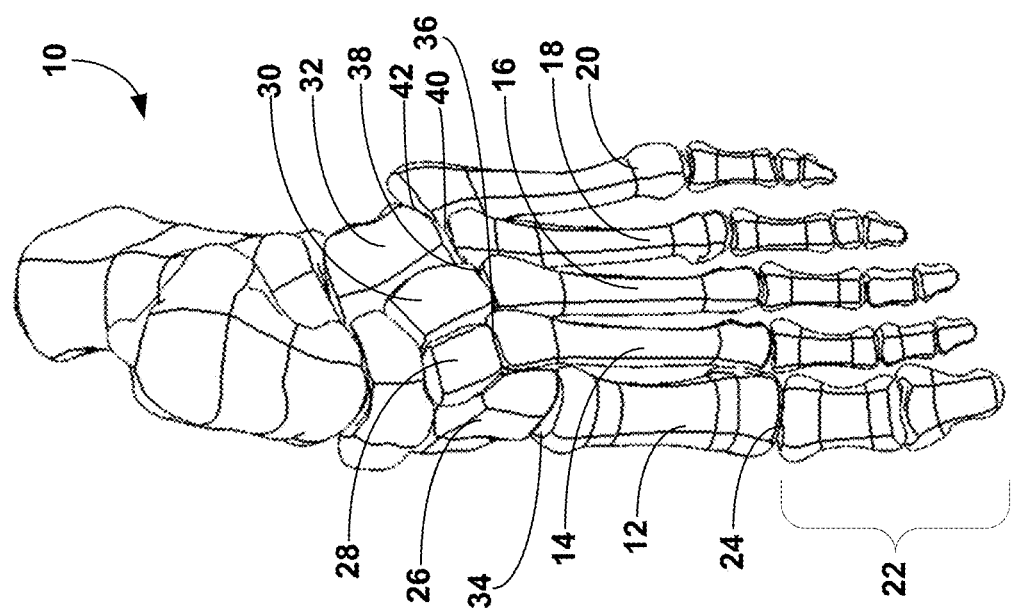

FIGS. 1A and 1B are top and front views, respectively, of a foot 10 showing normal metatarsal alignment positions. Foot 10 is composed of multiple bones including a first metatarsal 12, a second metatarsal 14, a third metatarsal 16, a fourth metatarsal 18, and a fifth metatarsal 20. First metatarsal 12 is on a medial-most side of the foot while fifth metatarsal 20 is on a lateral-most side of the foot. The metatarsals are connected distally to phalanges 22 and, more particularly, each to a respective proximal phalanx. The joint 24 between a metatarsal and a corresponding opposed proximal phalanx is referred to as a metatarsophalangeal ("MTP") joint. The first MTP joint is labeled as joint 24 in FIG. 1A, although second, third, fourth, and fifth MTP joints are also illustrated in series adjacent to the first MTP joint.

The first metatarsal 12 is connected proximally to a medial cuneiform 26, while the second metatarsal 14 is connected proximally to an intermediate cuneiform 28, and the third metatarsal 16 is connected proximally to lateral cuneiform 30. The fourth and fifth metatarsals 18, 20 are connected proximally to the cuboid bone 32. The joint between a metatarsal and opposed bone (cuneiform, cuboid) is referred to as the tarsometatarsal ("TMT") joint. FIG. 1A designates a first TMT joint 34, a second TMT joint 36, a third TMT joint 38, a fourth TMT joint 40, and a fifth TMT joint 42. The angle between adjacent metatarsals is referred to as the intermetatarsal angle ("IMA").

In the example of FIGS. 1A and 1B, foot 10 is illustrates as having generally normally aligned metatarsals. Normal metatarsal alignment may be characterized, among other attributes, by a low intermetatarsal angle (e.g., 9 degrees or less, such as 5 degrees or less) between the first metatarsal and the second metatarsal. In addition, the lesser metatarsals may be generally parallel to a longitudinal axis bisecting the foot proximally to distally.

Figure 3A:
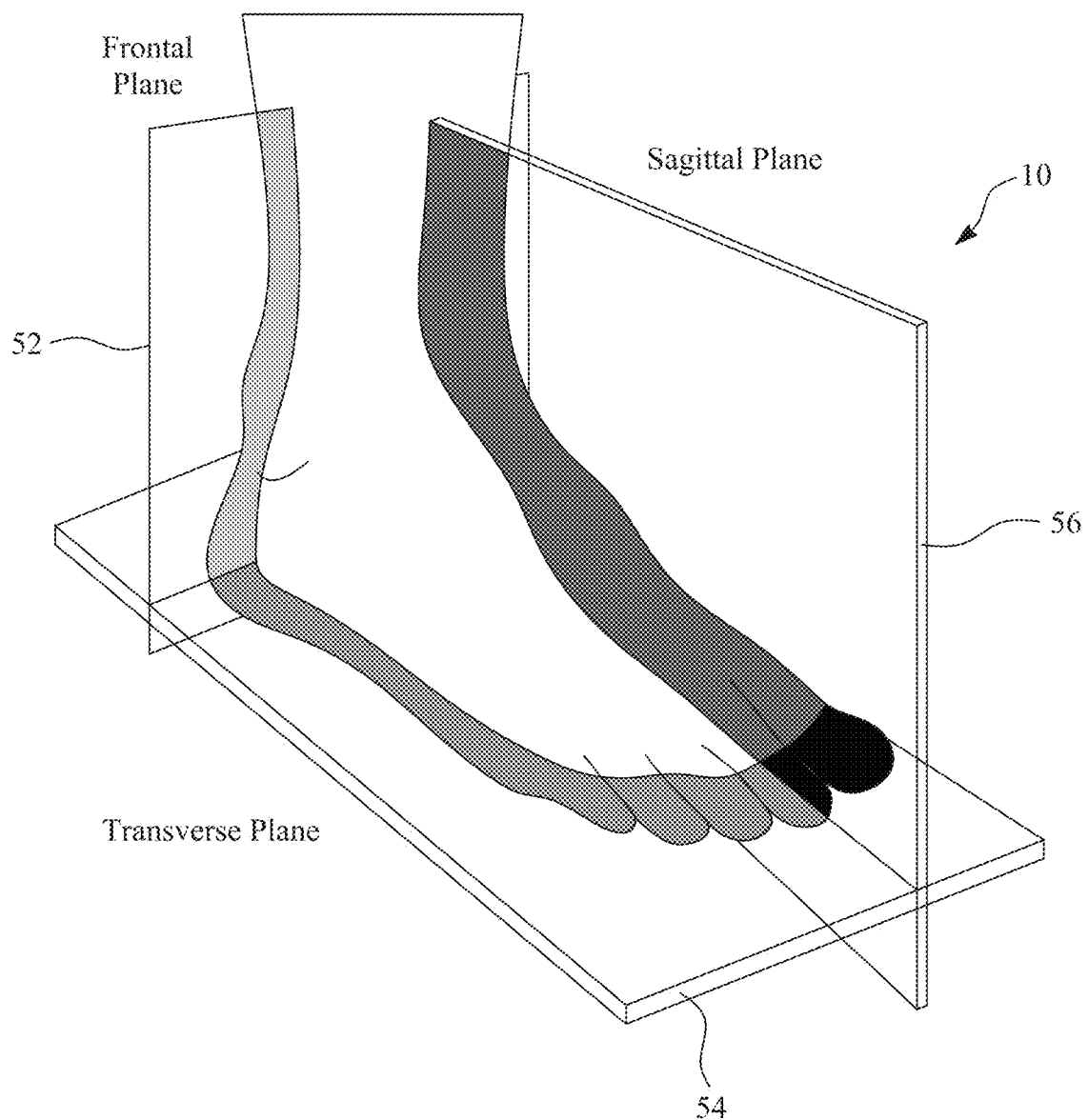
FIG. 3A illustrates the different anatomical planes of a foot.

FIG. 3A illustrates the different anatomical planes of foot 10, including frontal plane 52, transverse plane 54, and sagittal plane 56. The frontal plane 52, which is also known as the coronal plane, is generally considered any vertical plane that divides the body into anterior and posterior sections. On foot 10, the frontal plane 52 is a plane that extends vertically and is perpendicular to an axis extending proximally to distally along the length of the foot. The transverse plane 54, which is also known as the horizontal plane, axial plane, or transaxial plane, is considered any plane that divides the body into superior and inferior parts. On foot 10, the transverse plane 54 is a plane that extends horizontally and is perpendicular to an axis extending dorsally to plantarly (top to bottom) across the foot. Further, the sagittal plane 56 is a plane parallel to the sagittal suture which divides the body into right and left halves. On foot 10, the sagittal plane 56 is a plane that extends vertically and intersects an axis extending proximally to distally along the length of the foot.

Figure 2B:
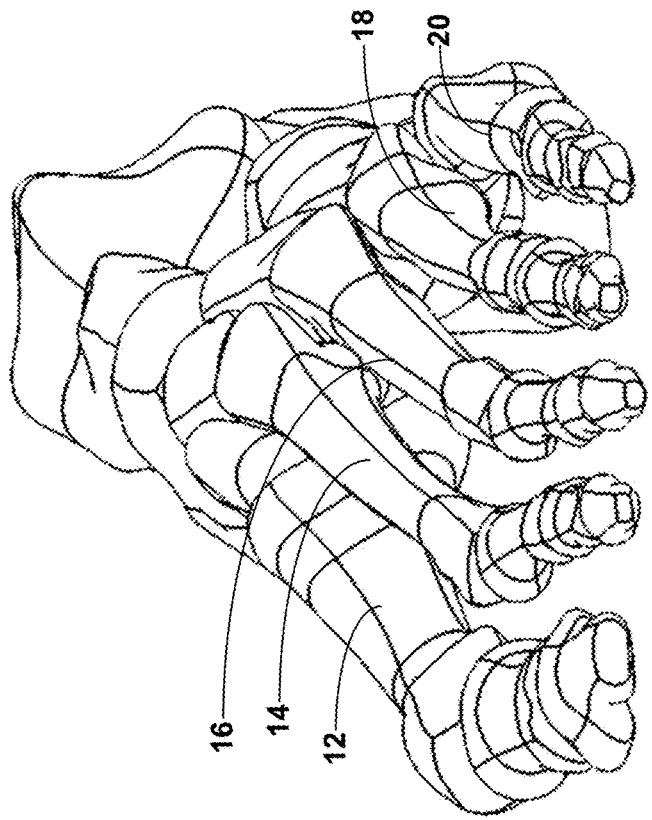
FIGS. 2A and 2B are top and front views, respectively, of a foot showing an example metatarsal adductus bone misalignment.
Figure 2A:
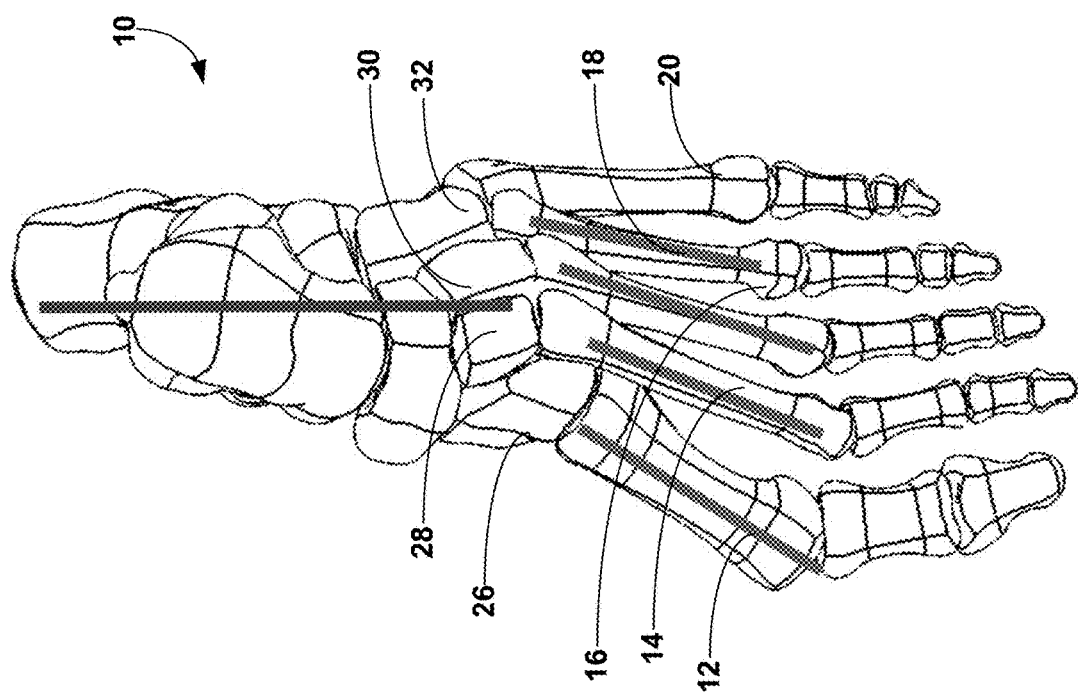
Figure 3B:
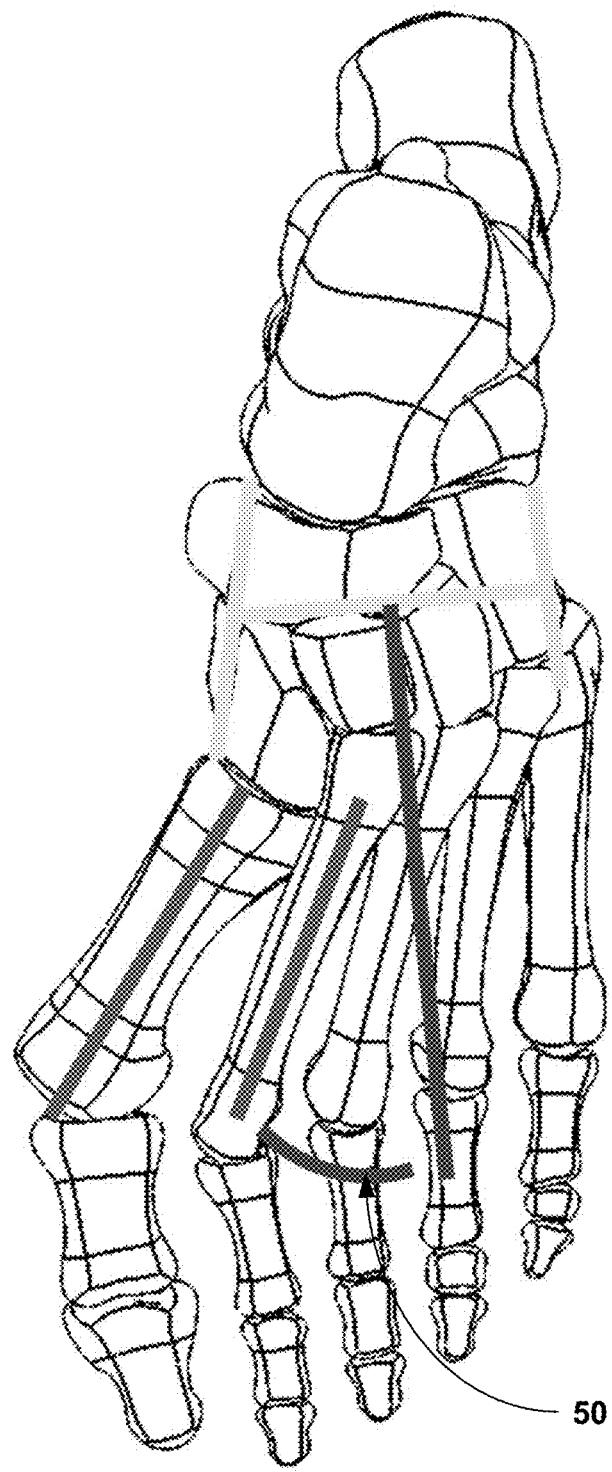
FIG. 3B illustrates the metatarsus adductus of the foot from FIGS. 2A and 2B characterized by a metatarsus adductus angle.

For patients afflicted with metatarsal adductus, at least one or more of the lesser metatarsals (the second through fifth metatarsals) may be deviated medially in the transverse plane (e.g., in addition to or in lieu of being rotated in the frontal plane and/or being deviated in the sagittal plane relative to clinically defined normal anatomical alignment for a standard patient population). FIGS. 2A and 2B are top and front views, respectively, of foot 10 showing an example metatarsal adductus bone misalignment. As shown in this example, the metatarsals are deviated medially relative to an axis bisecting the foot. This can result in an abnormal biomechanical structure benefiting from surgical intervention. FIG. 3B illustrates the metatarsus adductus of foot 10 from FIGS. 2A and 2B being characterized by a metatarsus adductus angle 50.

Figure 4:
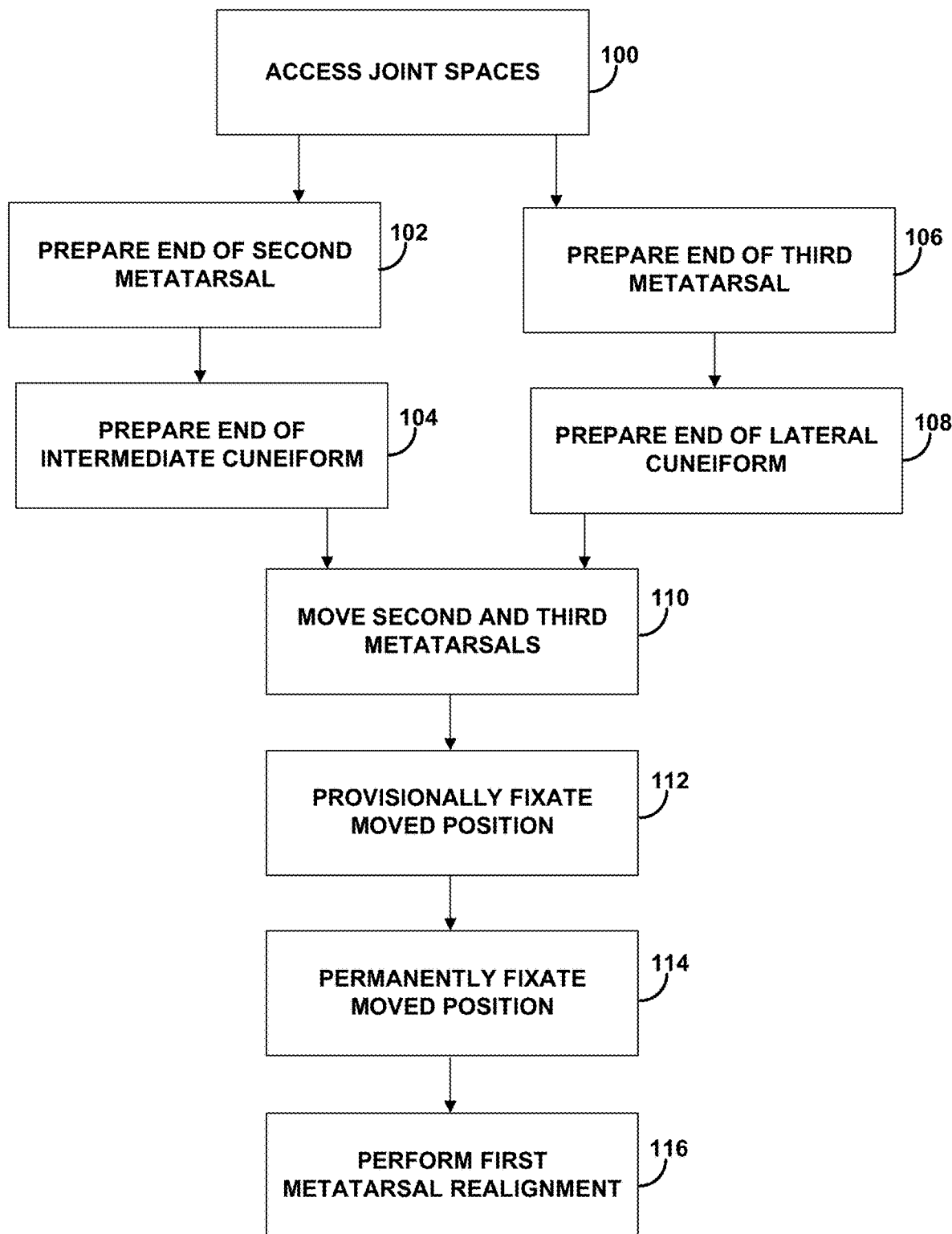
FIG. 4 is a flow diagram illustrating an example technique for preparing TMT joints for fusion and realigning multiple metatarsals to treat a metatarsus adductus deformity.

Bone positioning techniques and instruments can be useful to correct a misalignment of one or more bones, such as a metatarsal adductus and/or hallux valgus metatarsal misalignment. FIG. 4 is a flow diagram illustrating an example technique for preparing TMT joints for fusion and realigning one or more (e.g., multiple) metatarsals to treat at least a metatarsus adductus deformity. The technique will be described with respect to the bone numbering introduced with respect to FIGS. 1A and 1B, although may be performed on other bones. For purposes of discussion, the technique of FIG. 4 will be discussed with respect to different example images, although may be performed without such instrumentation or with different instrumentation, as discussed herein.

With reference to FIG. 4, the example technique includes surgically accessing at least the second TMT and third TMT joints (100). To surgically access the joints, the clinician may make one or more incisions (e.g., on a dorsal side of the foot) exposing the second and third TMT joints. The clinician may dissect through the skin, subcutaneous tissue, and fascia. The clinician may mobilize the extensor digitorum brevis muscle belly from the extensor hallucis brevis and retract the muscle. Soft tissue and/or bone overgrowth may be removed to facilitate joint visualization.

In instances where the clinician is also performing a first metatarsal correction, the clinician may also surgically access the first TMT joint. Although the clinician may make a single incision spanning the first, second, and third TMT joints, a dual incision approach can avoid unnecessary cutting and scarring. With the dual incision approach, the clinician may make one incision providing dorsal (e.g., dorsolateral and dorsomedial) access (and/or, in other examples, medial access) to the first TMT joint and a second incision providing dorsal (e.g., dorsolateral and dorsomedial) to the second and third TMT joints, resulting in an intermediate portion of skin between the first and second incisions. When making a dual incision, the surgeon may surgically access the first TMT joint before, after, or concurrent with surgically accessing the second and third TMT joints.

In practice, it may be challenging for a clinician to quickly and accurately locate the position of one or more TMT joints on the patient's foot, particularly one or more lesser TMT joints that may be offset because of a bone deformity. The clinician may utilize a joint finding guide (e.g., incision guide) to help identify the location of a TMT joint, e.g., before making an incision through the skin and/or after making an incision to help find the joint subcutaneously. As one example, the joint finding guide may be an instrument fabricated at least partially from a radiopaque material to designate the location of the TMT joint under imaging. For example, the joint finding guide may include one or more radio-identifiable marking lines that are distinguishable from a remainder of the guide under imaging. The one or more radio-identifiable marking lines can be formed from a different material than a remainder of the guide, have a different thickness than a remainder of the guide, and/or otherwise be distinguishable under imaging from the remainder of the guide. In either configuration, the clinician may align a radio-identifiable marking feature (e.g., line) with a TMT joint under imaging to designate the location for subsequently accessing a joint. The clinician may take a fluoroscopic (e.g. X-ray) image of at least a portion of foot 10 encompassing the target TMT joint prior to making an incision and/or after making the incision. The clinician can use the radio-identifiable marking on the joint finding guide to designate the location of the joint, e.g., to subsequently make an incision over the joint and/or to release the joint at the designated location.

As another example, the joint finding guide may take the form of a tool configured (e.g., sized and/or shaped) to allow the clinician to physically probe in the region of the TMT joint until the tool depresses into the TMT joint. For example, the joint finding guide may be a flat-head screw driver, rod, or other instrument. The tool may have a blunt tip and/or may be selected to minimize or prohibit bone cutting or other bone removal as the tool may contact bone while probing for the TMT joint. The clinician may probe for the joint using the tool prior to making an incision and/or after making the incision.

Thus, in various examples, the clinician may identify a TMT joint space by visual and/or tactile inspection and/or through radiographic (e.g., fluoroscopic) imaging. Independent of whether the clinician utilizes one or more joint finding guides to help locate a TMT joint, the clinician can make an incision to surgically expose the joint. With the joint exposed, the clinician may optionally release soft tissue from each accessed TMT joint (e.g., by inserting a cutting instrument in the joint) to help mobilize the joint for subsequent realignment.

With access to the TMT joint spaces, the technique of FIG. 4 involves preparing the end faces of the bones forming the second TMT joint 36 in the third TMT joint 38. In particular, the clinician can prepare the end of the second metatarsal 14 facing the second TMT joint (102), prepare the end of the third metatarsal 16 facing the third TMT joint (104), prepare the end of the intermediate cuneiform 28 facing the second TMT joint (106), and/or also prepare the end of the lateral cuneiform 30 facing the third TMT joint (108). While FIG. 4 schematically illustrates an example order in which the bones defining the second and third TMT joints can be prepared, it should be appreciated that the surgical technique is not limited to any particular order of preparation. For example, the clinician can prepare one or both cuneiforms before preparing one or more metatarsals, can prepare one or both metatarsals before preparing one or more cuneiforms, can prepare the ends of one metatarsal and one cuneiform defining one TMT joint before preparing the bone ends of the other TMT joint, or perform bone preparation in yet another order.

In general, the clinician can prepare the end of each bone forming a TMT joint so as to promote fusion of the bone ends across the TMT joint following realignment. Bone preparation may involve using a tissue removing instrument, which may also be referred to as a cutting instrument, to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand, with the aid of a cutting guide having a guide surface positionable over the portion of bone to be cut, and/or with the aid of a bone preparation template. When using a cutting guide, a cutting instrument can be inserted against the guide surface (e.g., between a slot defined between two guide surfaces) to guide the cutting instrument for bone removal. When using a bone preparation template, the bone preparation template can be used to mark or otherwise designate where on one or more bones a preparation step (e.g., cutting) should be performed. The clinician may then preform a freehand bone preparation step (e.g., cutting) at a location indicated through use of the bone preparation template.

In some examples, the clinician cuts at least one bone defining the second TMT joint (e.g., one or both of second metatarsal 14 and intermediate cuneiform 28) and also cuts at least one bone defining the third TMT joint (e.g., one or both of third metatarsal 16 and the lateral cuneiform 30). The clinician may cut both bones defining the second TMT joint or may cut only one bone defining the joint and perform a different preparation technique on the other bone. Similarly, the clinician may cut both bones defining the third TMT joint or may cut only one bone defining the joint and perform a different preparation technique on the other bone.

Where the clinician cuts at least one bone forming a TMT joint, each such cut may be parallel or non-parallel to the end of the bone being cut in one or more of the frontal, transverse, and sagittal planes. For example, the cut may be angled in the transverse plane relative to the end face of the bone and parallel to the end face of the bone in the frontal plane. As other examples, the cut may be curved, arced, spherical, zig-zag, or may define other desired cut shape to facilitate realignment and fusion of one bone relative to another bone portion. In some examples, the end faces of the two bones defining the TMT joint are each prepared by cutting an end portion of each bone to create a shaped opening between the end faces. The opening may have a shape that allows the bones to be repositioned relative to each other (e.g., partially or fully closing the opening created in the process of realignment) to facilitate realignment and subsequent fusion.

In one example, the clinician can cut the end of the bone being prepared at an angle relative to the end face in the transverse plane, creating a wedge-shaped section of bone that is released from a remainder of the bone being cut. This can create a wedge-shaped opening between the newly defined end of the bone being cut and the opposing bone across the TMT joint being prepared. The wedge-shaped opening may enlarge moving from the medial side of the TMT joint to the lateral side of the TMT joint. For example, the wedge-shaped bone portion and corresponding opening may have a generally triangular-shape. The wedge-shaped opening can provide a gap across the TMT joint that can be closed by subsequently pivoting the metatarsal in the transverse plane. Again, however, other shaped cuts can be performed on one or both bones facing the TMT joint without departing from the scope of the disclosure. Example bone cutting shapes and configurations that may be used on one or more bone ends defining a TMT joint are described in U.S. Pat. No. 10,512,470, dated Dec. 24, 2019 and titled "OSTEOTOMY PROCEDURE FOR CORRECTING BONE MISALIGNMENT" and U.S. Pat. No. 10,582,936, dated Mar. 10, 2020, and titled "DEVICES AND TECHNIQUES FOR PERFORMING AN OSTEOTOMY PROCEDURE ON A FIRST METATARSAL TO CORRECT A BONE MISALIGNMENT," the entire contents of both of which are incorporated herein by reference.

Figure 5A:
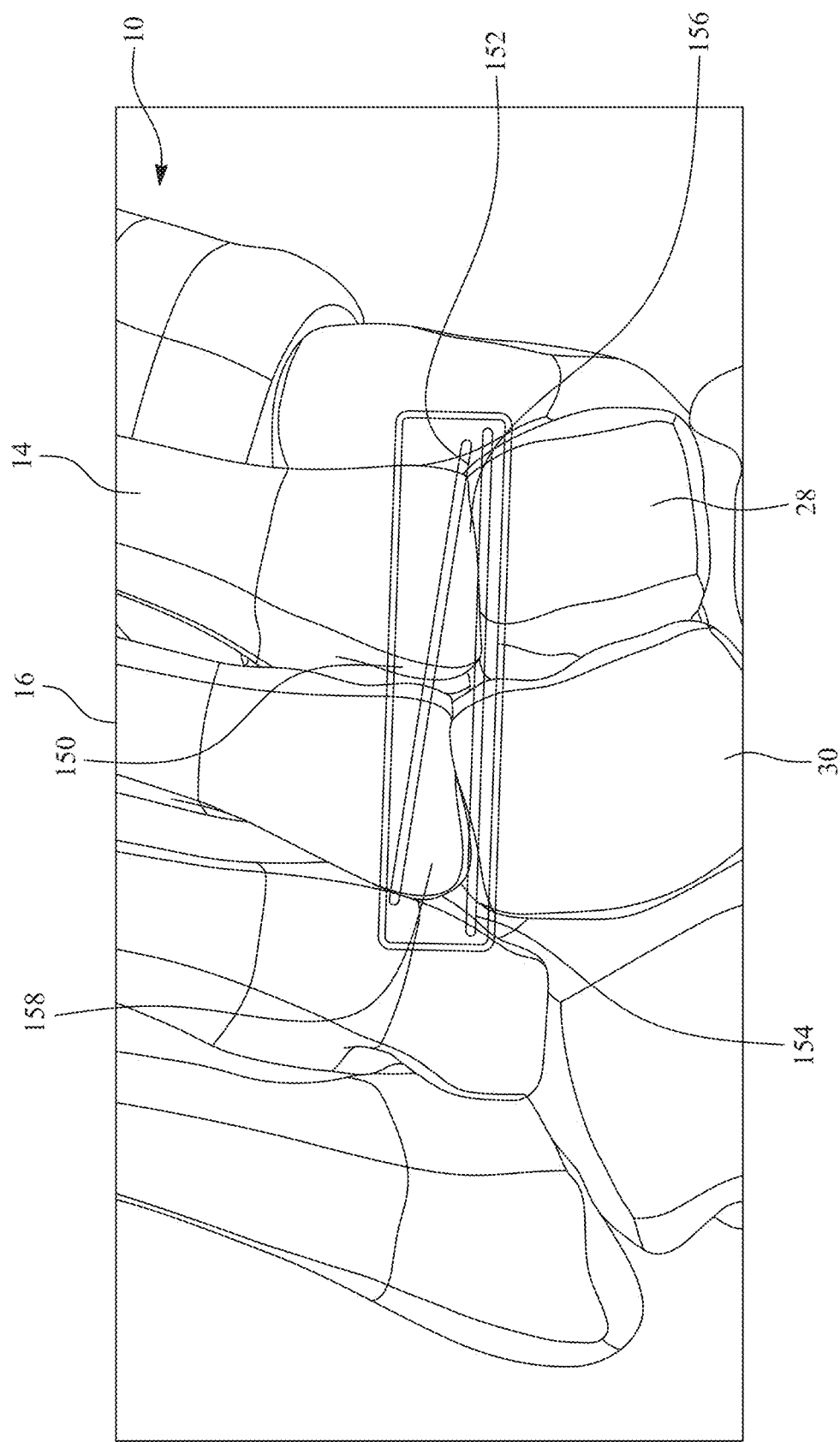
FIG. 5A is a top view of a foot showing an example cut guide positioned over the second and third TMT joints to illustrate example bone wedges that may be cut during joint preparation.

FIG. 5A is a top view of foot 10 showing an example cut guide 150 positioned over the second and third TMT joints to illustrate example bone wedges that may be cut during joint preparation. In this example, cut guide 150 is shown defining a first guide surface 152 (which is illustrated as a cutting slot) positioned over a portion of a second metatarsal 14 and a portion of a third metatarsal 16 to be cut. Cut guide 150 is also shown as defining a second guide surface 154 (which is illustrated as a cutting slot) positioned over a portion of an intermediate cuneiform 28 and a lateral cuneiform 30 to be cut. The clinician can advance a cutting instrument parallel to first guide surface 152 to cut an end of second metatarsal 14 and also to cut an end of third metatarsal 16. The clinician can also advance the cutting instrument parallel to second guide surface 154 to cut an end of intermediate cuneiform 28 and lateral cuneiform 30. In different implementations, a guide surface of cut guide 150 may be linear, curved, and/or define yet other shapes. According, the step of guiding a cutting instrument parallel to the guide surface may result in a linear cut, a curved cut, or yet other shaped cut across the bone.

In the example of FIG. 5A, first guide surface 152 is illustrated as being angled in the transverse plane across the second and third metatarsals 14, 16. The first guide surface 152 is illustrated as being angled from a medial-proximal side of second metatarsal 14 toward a lateral-distal side of third metatarsal 16. The lateral-distal side of third metatarsal 16 may still be on the proximal half of the metatarsal, albeit comparatively distal to the proximal location on the second metatarsal. By preforming an angled cut relative to the end faces of the bones being cut, a wedge-shaped bone portion may be released from the bone. In FIG. 5A, a wedge-shaped section 156 of second metatarsal 14 is released upon cutting the second metatarsal. Further, a wedge-shaped section 158 of third metatarsal 16 is released upon cutting the third metatarsal. Each wedge-shaped section of bone removed via cutting may have a narrow width (e.g., apex) on a medial side of the bone being cut and a wider width (e.g., base) on a lateral side of the bone being cut. The degree of angulation in the specific dimensions of the bone wedge formed during cutting may vary depending on the anatomy of the patient and the extent of the deformity being corrected. In either case, the bone wedges so cut can be removed from the TMT joint spaces to define a wedge-shaped opening relative to an opposed bone.

In the example of FIG. 5A, the clinician can use second guide surface 154 to guide the cutting instrument to cut an end of intermediate cuneiform 28 and lateral cuneiform 30 to promote fusion following realignment of the metatarsals. The cuts performed on the intermediate cuneiform 28 and lateral cuneiform 30 may be generally parallel to the end face of a bone being cut (e.g., in the transverse plane) or may be angled relative to an end face of the bone being cut. In still other examples, the end faces of one or both of intermediate cuneiform 28 and lateral cuneiform 30 may not be cut but may be prepared using a different technique as discussed above (e.g., fenestrated).

In some examples in which the second metatarsal 14 and the third metatarsal 16 are prepared by cutting, the metatarsals may be cut using a single continuous cut across both metatarsals. For example, the clinician may guide a cutting instrument linearly from a medial side of the second metatarsal 14 toward the lateral side of the third metatarsal 16 or from the lateral side of the third metatarsal to the medial side of the second metatarsal. In either case, the clinician may form a continuous cut line transecting the ends of the second and third metatarsals. Such a continuous cut across the bases of the second and third metatarsals may be useful to promote reliable reduction of the metatarsus adductus angle during subsequent bone realignment. In applications where the intermediate cuneiform 28 and the lateral cuneiform 30 are cut in addition to or in lieu of the ends of the metatarsals, the two cuneiforms may or may not be cut using such a continuous cut across the ends of the two metatarsals.

In other applications of the surgical technique, the ends of the second metatarsal 14 and third metatarsal 16 may be cut independently (e.g., without moving the cutting instrument in a continuous cutting line across the two metatarsals). For example, when the patient exhibits a significant step off (e.g., distal offset) between the end of the intermediate cuneiform 28 and the end of the lateral cuneiform 30, the ends of the opposed second and third metatarsals 14, 16 may be prepared independently (e.g., through two separate cuts) in lieu of forming a continuous cut across the ends of the two metatarsals. The ends of the opposed second and third metatarsals 14, 16 may be prepared independently for other reasons as well, such as to provide independent control/adjustability over the cut angles on the second and third metatarsals.

While FIG. 5A illustrates one example cutting guide 150 and one example cutting arrangement that may be used to prepare the ends of the second and third TMT joints, it should be appreciated that a technique in accordance with the disclosure is not limited to such example guide or cutting arrangements. For example, a technique according to disclosure may be performed freehand (without the use of a cutting guide) or may be performed with a cutting guide having a different configuration. In addition to or in lieu of using a cutting guide, the clinician may position a bone preparation template over one or more bone portions to be subsequently cut. The bone preparation template may be configured (e.g., sized and/or shaped) to indicate where on the underlying bone the bone should be cut or otherwise prepared. Positioning the bone preparation template on the underlying bone may mark or otherwise indicate on the bone where the bone should be prepared and/or the clinician may use the bone preparation template to mark where on the bone the bone should be prepared. The clinician may subsequently remove the bone preparation template and preform a bone preparation step (e.g., cutting) at the location marked or otherwise indicated using the template.

Further, although FIG. 5A illustrates angled cuts being performed on the ends of second metatarsal 14 and third metatarsal 16, such angled cuts are not required. In general, any one or both of the metatarsal and cuneiform bones forming the TMT joint being prepared may be cut so as to establish an opening for rotating the metatarsal in one or more planes (e.g., the transverse plane) and/or facilitating realignment of one or more bones. The other of the bones forming the TMT joint may also be prepared by cutting or may be prepared using a different bone preparation technique.

As one example, the clinician may remove a wedge-shaped section 156 of bone from the second metatarsal and remove a wedge-shaped section 158 of bone from the third metatarsal. The clinician can cut, fenestrate, and/or otherwise prepare the ends of the opposed intermediate cuneiform 28 and lateral cuneiform 30. In another example, the clinician may remove a wedge-shaped section of bone from the intermediate cuneiform 28 and/or remove a wedge-shaped section of bone from the lateral cuneiform 30. The clinician can cut, fenestrate, and/or otherwise prepare the ends of the opposed second metatarsal 14 and third metatarsal 16. In still another example, the clinician may remove a wedge-shaped section of bone from the cuneiform of one of the second and third TMT joints and remove a wedge-shaped section of bone from the metatarsal of the other of the second and third TMT joints. The end face of the opposed bone may be cut parallel to the end face of the bone, at an angle, and/or otherwise prepared (e.g., with or without cutting). For example, the clinician may remove a wedge-shaped section of both from the ends of both bones forming the TMT joint. In either case, the opening created between the ends of the bones defining the TMT joint may be defined by the cumulative amount of bone removed from both bone ends. As noted above, depending on the characteristics of the patient undergoing the surgical procedure, in yet other embodiments the clinician may not cut the end faces of the bones defining the second and third TMT joints or may perform a bone cut parallel to the end face of the bone. Further, while the foregoing examples are described as being performed by removing a wedge-shaped section of bone, a bone section having another shape can be removed, as described herein.

In instances where the clinician cuts the end face of the bone, the clinician may or may not perform one or more additional preparation steps on the end face prior to or after cutting the end face. In some examples, the clinician fenestrates the newly-formed end face of the bone after cutting the bone. The clinician may use a drill to fenestrate the end newly-formed end face of the bone being cut, which can help promote subsequent fusion of the bone following realignment. The clinician may fenestrate a bone face by making multiple openings (e.g., drill holes) in the bone face, providing multiple bleeding points in the end of the bone face. Each drill hole may be comparatively small relative to the cross-sectional area of the end face, such as less than 10% of the cross-sectional area of the end face, less than 5% of the cross-sectional area of the end face, or less than 1% of the cross-sectional area of the end face. The multiple openings can be arrayed at different locations across the end face to provide locations for promoting fusion across the end face. The number of holes formed during fenestration may vary and, in some examples, is greater than 5, such as greater than 10.

As another example of a preparation step that may be performed, the clinician may remove one or more protruding bone portions extending into and/or across the second TMT and/or third TMT joint line. The protruding bone portions may extend distally from the cuneiform into the joint space and/or proximally from the metatarsal into the joint space. For instance, as discussed in greater detail with respect to FIG. 29, certain patients may exhibit significant step off, or distal offset, between adjacent joint planes (e.g., between the plane defining the second TMT joint and the plane defining the third TMT joint). This can inhibit relative movement between the two joints for subsequent realignment and/or inhibit insertion of a cutting guide into one or both joint spaces. For these and other reasons, the clinician may remove the one or more protruding bone portions, e.g., to create a pocket or continuous joint line extending across the second TMT joint and the third TMT joint. The clinician may remove the one or more protruding bone portions using a cutting instrument either freehand and/or with the aid of a cutting guide, such as cutting guide 292 discussed in greater detail with respect to FIG. 30.

As another example, the clinician may typically visualize the location of a cutting guide and/or bone preparation template under radiographic imaging (e.g., fluoroscopy), e.g., to ensure that one or more guide planes or other guide features are appropriately positioned relative to one or more underlying bones. The clinician can adjust the position of the cutting guide or bone preparation template under imaging, e.g., until one or more guide planes or other alignment features are positioned over a desired portion or region of underlying bone to be marked, cut, and/or otherwise prepared.

Figure 5B:
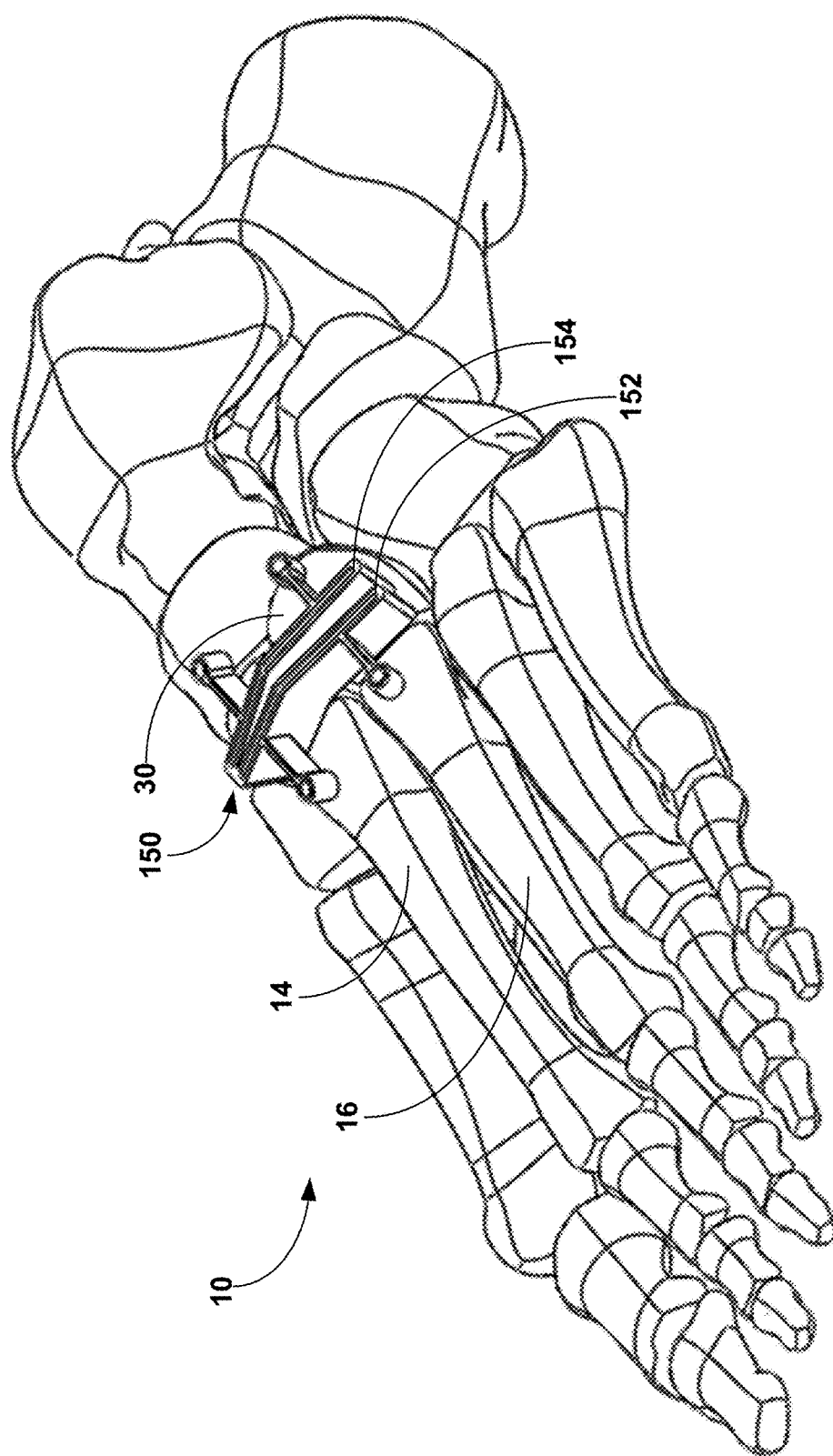
FIGS. 5B-5E illustrate example bone preparation steps that may be performed on a foot using an example cutting guide.
Figure 5C:
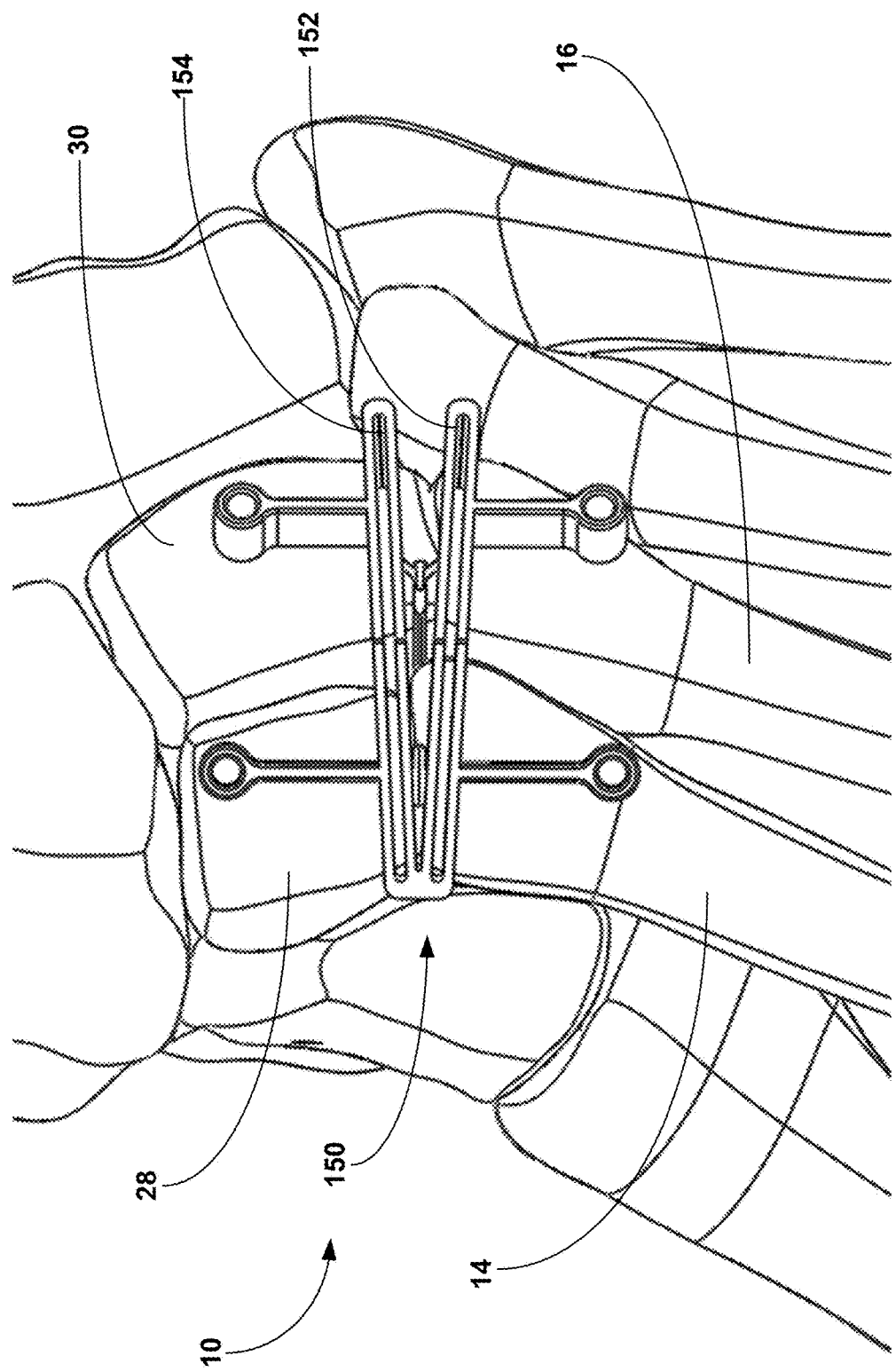

FIGS. 5B-5E illustrate example bone preparation steps that may be performed on foot 10 using an example configuration of cutting guide 150 according to a technique of the disclosure. In particular, FIGS. 5B and 5C are perspective and top (dorsal) view illustrations of foot 10 showing cut guide 150 positioned over a dorsal side of the foot. Specifically, cut guide 150 is shown with first guide surface 152 positioned over a portion of second metatarsal 14 and a portion of third metatarsal 16 to be cut, and second guide surface 154 is positioned over a portion of intermediate cuneiform 28 and lateral cuneiform 30 to be cut. In this example, cut guide 150 defines at least one fixation aperture positionable over each of second metatarsal 14, third metatarsal 16, intermediate cuneiform 28, and lateral cuneiform 30. A clinician can insert fixation pins through one or more (e.g., all) of the fixation apertures to secure the cut guide to underlying bone.

Figure 5D:
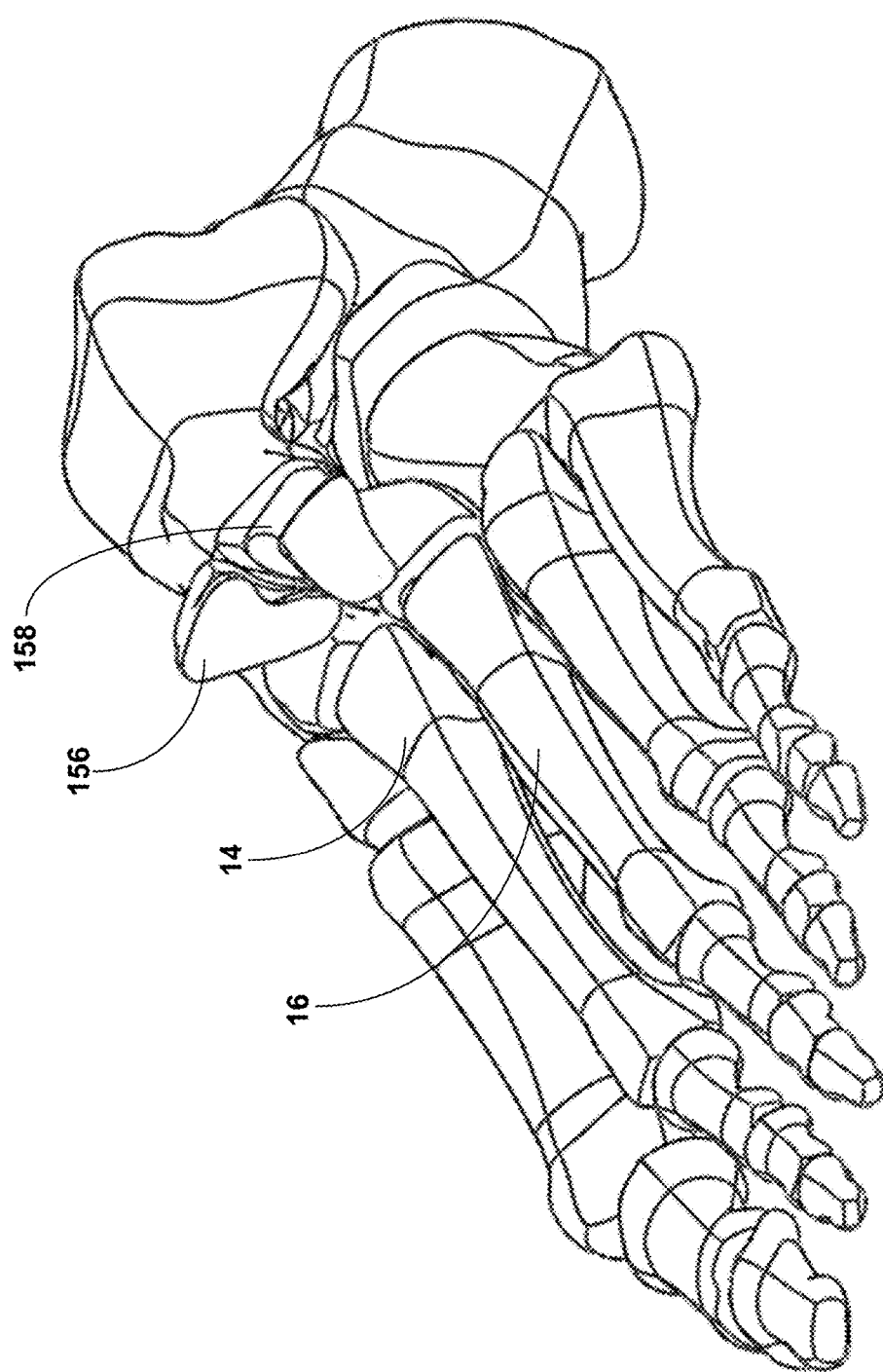
Figure 5E:
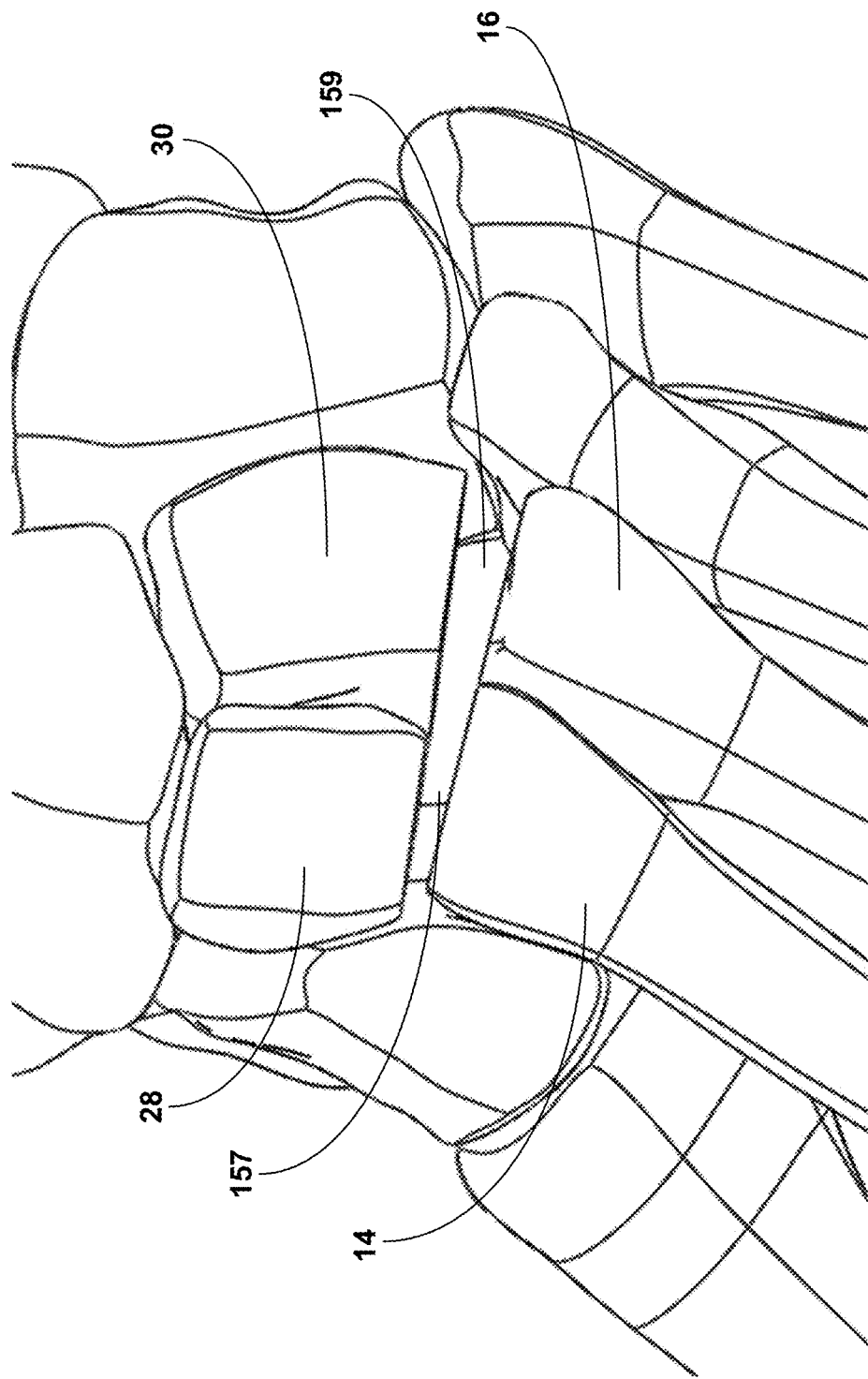

In use, the clinician can guide a cutting instrument along first guide surface 152 to cut an end of second metatarsal 14 and also to cut an end of third metatarsal 16. The clinician can also guide the cutting instrument along second guide surface 154 to cut an end of intermediate cuneiform 28 and lateral cuneiform 30. FIG. 5D is a perspective view of the foot showing example bone portions that can be removed after cutting, specifically illustrating an example wedge-shaped section 156 removed from second metatarsal 14 and an example wedge-shaped section 158 removed from third metatarsal 16. Additional bone sections may be removed from intermediate cuneiform 28 and lateral cuneiform 30. FIG. 5E illustrates an example opening 157 formed between second metatarsal 14 and intermediate cuneiform 28 upon removal of one or more bone portions and an example opening 159 formed between third metatarsal 16 and lateral cuneiform 30 upon removal of one or more bone portions.

With further reference to FIG. 4, the example technique involves moving the second metatarsal 14 and the third metatarsal 16 in at least one plane (110). While FIG. 4 schematically illustrates an example order in which the second and third metatarsals 14, 16 are moved after preparing the end faces of metatarsals 14, 16 and opposed intermediate and lateral cuneiforms 28, 30, other orders of bone preparation and movement may be performed. For example, the clinician can move the second and/or third metatarsals 14, 16 before preparing one or more metatarsals and/or one or more cuneiforms (e.g., before preparing the end faces of all of the bones). For instance, the clinician may move the second and third metatarsals 14, 16 and then prepare the end faces of metatarsals 14, 16 and opposed intermediate and lateral cuneiforms 28, 30. In these implementations, the clinician may or may not further move the second and/or third metatarsals 14, 16 after preparing the end faces of the metatarsals and cuneiforms. As another example, the clinician may prepare the end face of one or more bones (e.g., one or more metatarsals and/or cuneiforms), move one or both of second metatarsal 14 and third metatarsal 16, and then prepare the end face of one or more other bones (e.g., one or more metatarsals and/or cuneiforms).

Independent of the order of movement and bone preparation, the clinician may move the second and third metatarsals 14, 16 in one or more planes, such as the transverse plane, e.g., by pivoting the metatarsals about their proximal ends, causing a distal end of the metatarsals to move laterally in the transverse plane. In instances where a wedge-shaped opening was formed at the second and/or third TMT joints during bone preparation, lateral rotation of the distal ends of the second and third metatarsals may close the wedge-shaped opening(s) (or close another shaped opening, in instances in which a non-wedge-shaped opening was created). For example, translation of the distal ends of the second and third metatarsals 14, 16 laterally in the transverse plane may bring the ends of the second metatarsal 14 and opposed intermediate cuneiform 28 as well as the ends of the third metatarsal 16 and opposed lateral cuneiform 30 in generally parallel alignment. The clinician may move the second and/or third metatarsal in the frontal plane and/or sagittal plane in addition to or in lieu of moving one or both bones in the transverse plane. For example, the clinician may rotate one or both bones in the frontal plane and/or translate one or both bones (e.g., dorsally) in the sagittal plane.

In general, movement of second metatarsal 14 and third metatarsal 16 in the transverse plane can close the metatarsus adductus angle. The metatarsus adductus angle may be the angular measurement formed between the line bisecting the second metatarsal and the longitudinal line bisecting the lesser tarsus on a dorsoplantar radiograph. In some examples, the second and third metatarsals 14, 16 are moved until the metatarsus adductus angle for each metatarsal is 15° or less, such as 12° or less, 10° or less, 7° or less, 5° or less, or 3° or less.

The second metatarsal 14 and third metatarsal 16 may be moved individually or jointly (e.g., as a bone block). Moving the second and third metatarsals 14, 16 as a joined group may be helpful to achieve a more natural realignment of the metatarsals and correction of the metatarsus adductus deformity. To help move the second and third metatarsals 14, 16 as a joined group, the ligaments between the two metatarsals may be preserved during preparation of the second and third TMT joints. For example, the plantar TMT ligaments and ligaments between the second and third metatarsals 14, 16 may be preserved (e.g., remain uncut or unbroken) during preparation and movement of the second and third metatarsals. Preserving the ligament structure can help avoid destabilization of the second and third TMT joints during deformity reduction, which may improve the anatomical realignment of the bone structure.

Figure 6:
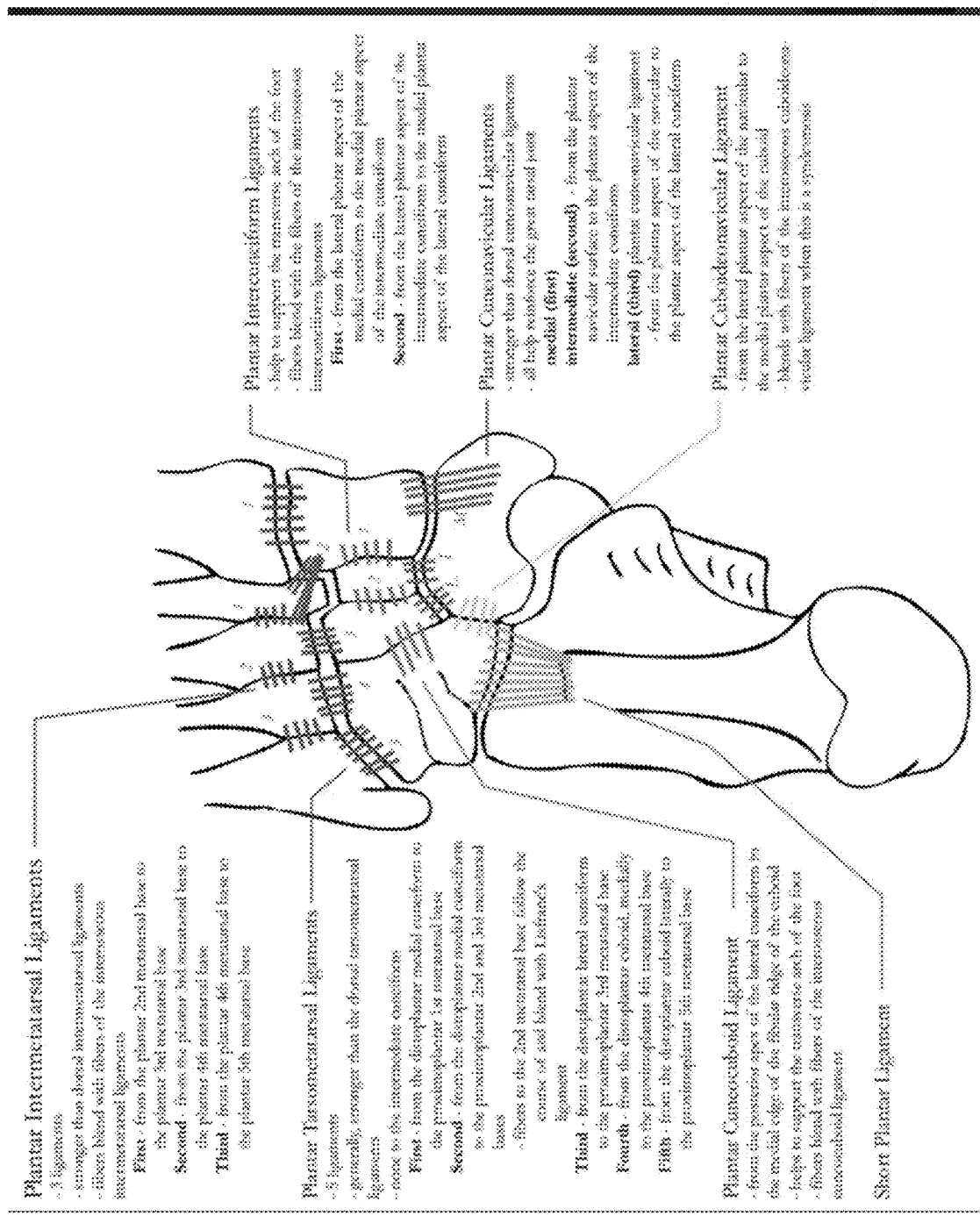
FIG. 6 is a diagram schematically illustrating the ligament structure of the foot.

FIG. 6 is a diagram schematically illustrating the ligament structure of the foot. As shown, the plantar TMT ligaments include a second plantar tarsometatarsal ligament between medial cuneiform 26 and the second and third metatarsals 14, 16. The plantar TMT ligaments also include a third plantar tarsometatarsal ligament between lateral cuneiform 30 and third metatarsal 16. A first plantar intermetatarsal ligament extends between second metatarsal 14 and third metatarsal 16. Ligamentous attachments between the second and third metatarsals, such as the second and third plantar tarsometatarsal ligaments and the first plantar intermetatarsal ligament, may be preserved during preparation and movement of the second and third metatarsals to correct the metatarsus adductus. This may allow the two metatarsals to move together as a joined bone group.

To move the second and third metatarsals 14, 16, either alone or in combination, the bones may be pivoted about their proximal base, causing the distal ends of the bones to translate laterally in the transverse plane. When moving the second and third metatarsals 14, 16 as a group, the clinician may pivot the second and third metatarsal bone block about the proximal medial portion of second metatarsal 14. The clinician may move the second and third metatarsals 14, 16 as a combined group in the transverse plane, with or without simultaneously rotating both bones in the frontal plane and/or adjusting the sagittal plane position of the bones. In some implementations, the clinician moves the second and third metatarsals 14, 16 as a group about the Lisfranc ligament while the second metatarsal remains attached to the Lisfranc ligament. Accordingly, the Lisfranc ligament may act as a hinge or pivot point about which the second and third metatarsal bone group can rotate in the transverse plane.

In other examples, the clinician may substantially independently move the second and third metatarsals 14, 16 (e.g., by applying a separate movement force to each metatarsal). For example, the clinician may apply a force to move third metatarsal 16 in one or more planes and subsequently apply a force to move the second metatarsal 14 in one or more planes (or, instead, move the second metatarsal 14 followed by the third metatarsal), such as in two or more, or all three planes. The clinician may or may not cut or otherwise release one or more ligamentous attachments interconnecting the second and third metatarsals 14, 16 to help facilitate independent repositioning of the two bones.

Independent of whether the clinician moves the second and third metatarsals 14, 16 together or independently, the intermetatarsal angle between second and third metatarsals may or may not change during metatarsus adductus correction. In other words, the intermetatarsal angle between second metatarsal 14 and third metatarsal 16 may or may not compress from a pre-corrected intermetatarsal angle to the intermetatarsal angle exhibited after correction. In some implementations, the second and third metatarsals 14, 16 are pivoted as a group within the transverse plane without substantially changing the intermetatarsal angle between the second and third metatarsals. For example, the intermetatarsal angle between the second and third metatarsals may change (e.g., reduce) less than 5°, such as less than 2°, or less than 1° from the angle exhibited before metatarsus adductus correction to the angle exhibited after the correction technique is performed.

To help facilitate movement of the second and third metatarsals in the transverse plane, the clinician may perform a soft tissue release between third metatarsal 16 and fourth metatarsal 18. The soft tissue release may mobilize the third metatarsal relative to the adjacent fourth metatarsal, allowing the joined second-third metatarsal bone block to be pivoted in the transverse plane.

In addition to moving the second metatarsal and the third metatarsal in the transverse plane, the clinician can also move fourth metatarsal 18 and fifth metatarsal 20 in one or more planes (e.g., one or more of the transverse plane, the frontal plane, and the sagittal plane), e.g., to close the metatarsus adductus angle exhibited by those lesser metatarsals. In practice, movement of second metatarsal 14 and third metatarsal 16 in one or more planes (e.g., the transverse plane) may cause the fourth and fifth metatarsals to naturally correct in same one or more planes (e.g., the transverse plane) without requiring separate surgical intervention on the fourth and fifth metatarsals 18, 20. For example, as the clinician rotates the distal end of second metatarsal 14 and third metatarsal 16, either alone or in combination, the distal ends of fourth metatarsal 18 and fifth metatarsal 20 may also move laterally. The proximal base of fourth metatarsal 18 and the proximal base of fifth metatarsal 20 may reorient relative to the cuboid bone 32, closing the metatarsus adductus angle of the fourth and fifth metatarsals. Without wishing to be bound by any particular theory, it is believed that force applied to the second and/or third metatarsal during movement may translate through the tissue and ligament structure interconnecting such metatarsal(s) to the fourth and fifth metatarsals, pulling the lesser metatarsals into realignment.

The position of fourth metatarsal 18 and fifth metatarsal 20 may correct without surgically accessing and preparing the metatarsal (in response to correction of second metatarsal 14 and/or third metatarsal 16). In other applications, however, the clinician may surgically access and prepare the bones defining fourth TMT joint 40 and/or fifth TMT joint 42 in addition to or in lieu of preparing one or more other TMT joints. For example, before or after moving the fourth metatarsal 18 and/or fifth metatarsal 20 in one or more planes (e.g., separate from or in combination with movement of the second metatarsal 14 and/or third metatarsal 16), the clinician can surgically access and prepare the bones defining fourth TMT joint 40 and/or fifth TMT joint 42. The clinician may decide whether to access and prepare the bones defining fourth TMT joint 40 and/or fifth TMT joint 42 depending, for example, on the nature of the deformity being corrected and the perceived need prepare the joints for bone realignment and/or fusion The clinician may prepare the end of fourth and/or fifth metatarsal 18, 20 and/or prepare the end of cuboid bone 32 opposite the end of the fourth and/or fifth metatarsal to facilitate realignment and/or fusion. The clinician can prepare the one or more bone ends using any of the bone preparation techniques discussed herein. In various examples, the clinician may independently prepare the ends of fourth and fifth metatarsals 18, 20 or may prepare the ends of the metatarsals together (e.g., such as positioning a single, continuous cutting guide plane over both ends for making a continuous cut, as discussed with respect to preparation of second metatarsal 14 and third metatarsal 16). Additionally or alternatively, the clinician may prepare the portions of the end face of cuboid bone 32 facing fourth and/or fifth metatarsal 18, 20 together or through separate preparation steps.

In instances where the clinician accesses and prepares the bones defining fourth TMT joint 40 and/or fifth TMT joint 42, one or both of the fourth metatarsal 18 and fifth metatarsal 20 may be realigned in one or more planes in response to a force applied to the second and/or third metatarsal 14, 16 (e.g., by translating the force through the tissue and ligament structure interconnecting the metatarsals). Additionally or alternatively, the clinician may apply a force to the fourth metatarsal 18 and/or fifth metatarsal 20 to move one or both metatarsal in one or more planes, such as two or more, or all three planes. The fourth and fifth metatarsals 18, 20 may be moved as joined bone block (e.g., either a bone block also connected to the bone block of the second and third metatarsal 14, 16 or separate therefrom) and/or may be moved substantially independently from each other (e.g., by applying a separate movement force to each metatarsal). Further, the clinician may apply a force to move only one of the fourth or fifth metatarsals.

With typical metatarsus adductus deformities, the metatarsals may exhibit a substantially uniplanar misalignment in the transverse plane (although may be misaligned in the frontal plane and/or sagittal plane). For this reason, the example technique of FIG. 4 has generally been described as correcting the second and third metatarsals 14, 16 (and, optionally, fourth and fifth metatarsals 18, 20) in the transverse plane. The clinician may move the metatarsals in only the transverse plane to correct the generally uniplanar misalignment. Alternatively, the clinician may move one or more of the metatarsals being realigned (e.g., multiple or all of the metatarsals been realigned) in more than one plane. For example, in addition to or in lieu of realigning the metatarsal(s) in the transverse plane, the clinician may adjust the rotational angle of the metatarsal(s) in the frontal plane and/or adjust the angle of the metatarsal(s) in the sagittal plane.

Where the clinician performs a multi-planar realignment, the clinician may move one or more metatarsals in multiple planes simultaneously through a single movement, e.g., by moving the metatarsal in an arc or other movement pathway to adjust the position of the metatarsal in multiple planes. The clinician may optionally perform further fine adjustment of the moved position of the one or more metatarsals, e.g., with the aid of a bone positioning device and/or by grasping the metatarsal by hand (e.g., with the aid of a pin inserted into the metatarsal) to finalize the position of the metatarsal prior to fixation.

In other examples, the clinician may perform different movement steps to move the one or more metatarsals in different planes. For example, the clinician may initially move the one or more metatarsals in one or two planes (e.g., transverse plane, frontal plane, sagittal plane) then move the one or more metatarsals in one or two other planes (e.g., the other of the transverse plane, frontal plane, sagittal plane), optionally followed by movement of the one or more metatarsals in a third plane. In other words, the clinician may perform different actions to move the one or more metatarsals in different planes. Each movement step may be performed with the aid of a bone positioning device (which may be the same or different device for different movement steps) and/or by grasping the metatarsal by hand (e.g., with the aid of a pin inserted into the metatarsal).

In some examples, the clinician may move one or more of the metatarsals being realigned (e.g., second metatarsal 14 and/or third metatarsal 16) proximally in the transverse plane toward the opposed bone in addition to or in lieu of moving the metatarsal(s) laterally. For example, the clinician may simultaneously move the metatarsal being realigned (e.g., second metatarsal 14 and/or third metatarsal 16) laterally and proximally in an arc (e.g., parabola) to establish a moved position of one or both metatarsals.

The clinician can move the one or more metatarsals being realigned (e.g., second metatarsal 14 and/or third metatarsal 16) by hand and/or with the aid of one or more instruments. For example, the clinician can grasp the second and/or third metatarsal and advance the distal end of the metatarsal laterally to reduce the metatarsus adductus angle. The clinician may insert one or more pins into the metatarsal being moved (e.g., second and/or third metatarsal) to provide a joystick or structure that can be grasped to manipulate movement of the bones. Additionally or alternatively, the clinician may utilize a tenaculum or tong to grasp one or both of the second and third metatarsals to facilitate realignment.

In some examples, the clinician may use a bone positioning guide (also referred to as a bone positioning device) to help apply a force to a metatarsal (e.g., second metatarsal 14 and/or third metatarsal 16) to facilitate realignment. The bone positioning guide may include one end that engages with (e.g., contacts, with or without being provisionally fixated to) the metatarsal to which the force is being applied and another end that engages with (e.g., contacts, with or without being provisionally fixated to) a different bone. For example, the bone positioning guide may have one end that engages with second metatarsal 14 and/or third metatarsal 16 and another end that engages with a bone other than the second and/or third metatarsals (e.g., a lesser metatarsal, a cuneiform, the cuboid bone). The bone positioning guide may have a mechanism that urges the two ends towards each other to reduce the metatarsus adductus angle. Example bone positioning guide engagement mechanisms that can function to move the two ends of the guide toward each other include a screw or threaded rod, a ratchet, a rack and pinion, and/or yet other features that translates a force applied by the clinician move the two ends of the bone positioning guide toward each other. Details on an example bone positioning guide that may be used are described in U.S. Pat. No. 9,936,994, issued Apr. 10, 2018, and titled "BONE POSITIONING GUIDE," the entire contents of which are incorporated herein by reference.

Figure 7A:
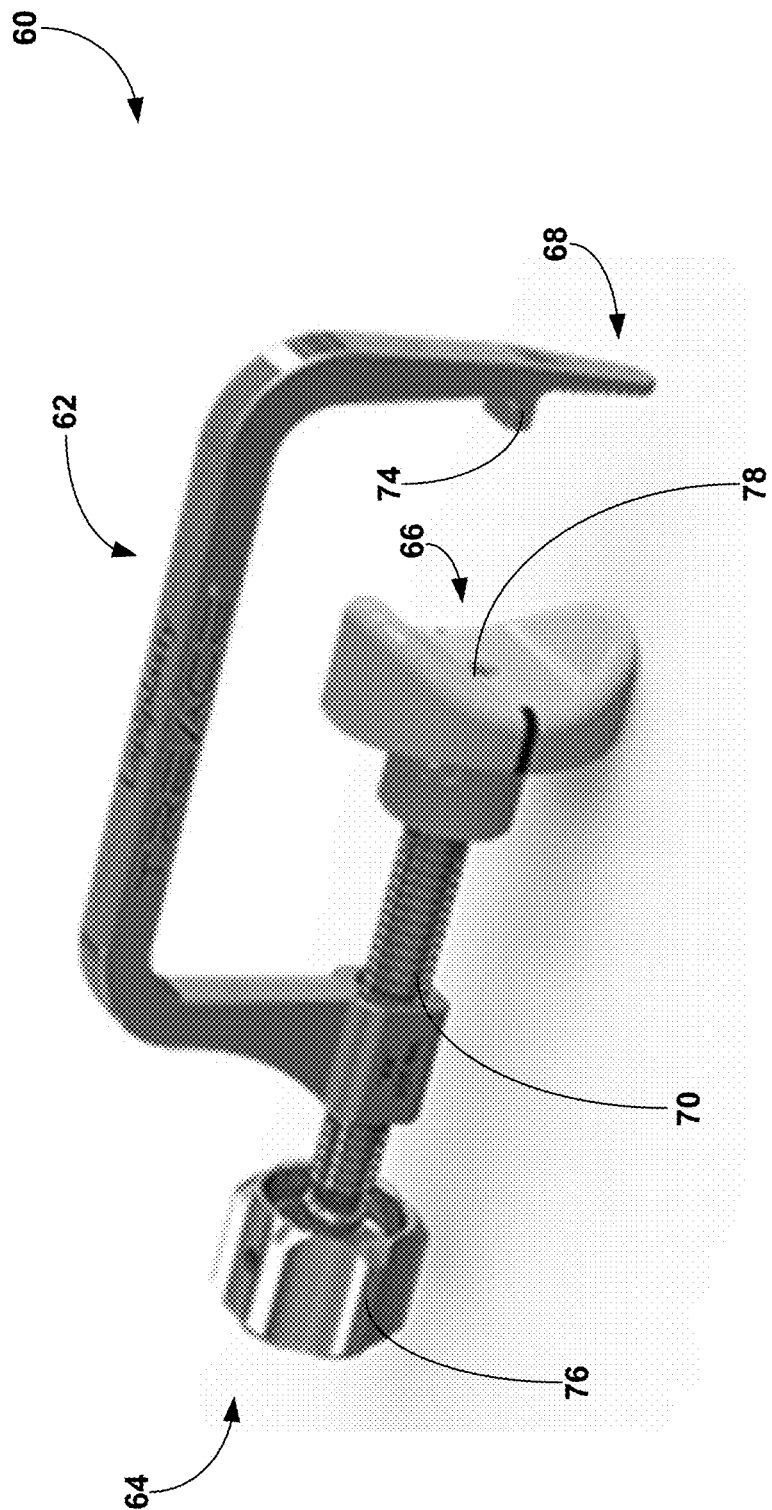
FIG. 7A is a side perspective view of an example bone positioner that can be used to move a metatarsal relative to an adjacent bone.

FIG. 7A is a side perspective view of an example bone positioner 60 (also referred to as a bone positioning device) that can be used to move a metatarsal relative to an adjacent bone. In some implementations, the bone positioning device includes a metatarsal engagement member, a tip, and a mechanism to move the metatarsal engagement member and the tip relative to each other in one or more planes. For example, the mechanism may move the metatarsal engagement member and the tip towards each other (e.g. moving the metatarsal engagement member towards the tip, moving the tip towards the metatarsal engagement member, or moving both simultaneously). The bone positioning device may also include an actuator to actuate the mechanism. When the mechanism engaged, it can cause a metatarsal engaged with the metatarsal engagement member to move to correct an alignment in at least one plane with respect to a second bone in contact with the tip.

In the embodiment of FIG. 7A, bone positioning device 60 includes a main body member 62, a shaft 64, a metatarsal engagement member 66 connected to the shaft, and a tip 68 is connected to the main body member. In general, main body member 62 can be sized and shaped to clear anatomy or other instrumentation (e.g., pins and guides) while positioned on a patient. In the embodiment of FIG. 7A, the main body member 62 is generally C-shaped. Although bone positioning device 60 is illustrated as being formed of two components, main body member 62 and shaft 64, the guide can be fabricated from more components (e.g., three, four, or more) that are joined together to form the guide.

A shaft 64 can be movably connected to the main body member 62. In some embodiments, the shaft 64 includes threads 70 that engage with the main body member 62 such that rotation of the shaft translates the shaft with respect to the main body member. In other embodiments, the shaft can slide within the main body member and can be secured thereto at a desired location with a set screw. In yet other embodiments, the shaft can be moved with respect to the main body by a ratchet mechanism or yet other mechanism that rotates and/or linearly translates metatarsal engagement member 66 relative to tip 68. In the embodiment shown, the shaft moves along an axis that intersects the tip. In other embodiments, the shaft and/or metatarsal engagement member is offset from the tip.

In general, metatarsal engagement member 66 may be configured (e.g., sized and/or shaped) to be positioned in contact, directly or indirectly, with a metatarsal to be repositioned. For example, depending on the size and/or shape of metatarsal engagement member 66, the metatarsal engagement member may be positioned subcutaneously in contact with a metatarsal bone to be realigned or may be positioned in contact with an external surface of the skin overlying the metatarsal bone to be realigned. For instance, in either configuration, metatarsal engagement member 66 may be positioned on a medial side of a metatarsal to be realigned (e.g., medial side of second metatarsal 14, third metatarsal 16, fourth metatarsal 18, fifth metatarsal 20) and tip 68 positioned in contact with another bone (e.g., with or without being provisionally fixated thereto), such as a laterally-located bone.

Metatarsal engagement member 66 may define a concave shape to generally conform and/or wrap partially around the underling cylindrical bone. The concave shape may include define a continuous radius of curvature, a V-shape, a planer region between outwardly extending sidewalls, and/or other shape having a concavity. In still other examples, metatarsal engagement member 66 may be planar.

Tip 68 can be useful for contacting a bone, such as a bone different than the bone being moved by bone positioning device 60. For example, if metatarsal engagement member 66 is positioned over a medial side of one metatarsal, the tip can be positioned over with a lateral side of a different metatarsal (e.g., the third, fourth, or fifth metatarsal), either directly in contact with the bone or over a lateral side of skin covering such metatarsal. In different configurations, tip 68 may be straight or may be tapered to facilitate percutaneous insertion and contact with bone. The tip can also include a textured surface, such as serrated, roughened, cross-hatched, knurled, etc., to reduce slippage between the tip and bone. In the embodiment shown, tip 68 further includes a depth stop 74. Depth stop 74 can limit a depth of insertion into an intermetatarsal space (e.g., by contacting a dorsal surface of the metatarsal against which tip 68 is intended to be positioned).

As shown in FIG. 7A, bone positioning device 60 can also include an actuator (e.g., a knob or a handle) 76 to actuate the mechanism, in this embodiment associated with the shaft. In the embodiment shown, the actuator can be useful for allowing a user to rotate the shaft with respect to the main body member 62. Actuator 76, shaft 64, and/or metatarsal engagement member 66 may include a cannulation 78 extending therethrough to allow the placement of a fixation wire (e.g., K-wire) through these components and into or through a bone engaged with the metatarsal engagement member. For example, a fixation wire can be placed into the bone engaged with metatarsal engagement member 66 to fix the position of the metatarsal engagement member with respect to the bone. In another example, the fixation wire can be placed through the bone in contact with the metatarsal engagement member and into an adjacent bone to maintain a bone position of the bone in contact with the metatarsal engagement member and the adjacent bone. Although shaft 64 and actuator 76 are illustrated as projecting away from a side of main body member 62, one or both features may be positioned at a different location (e.g., extending dorsally above main body member 62 through a mechanical linkage) to facilitate positioning of bone positioning guide 60 (e.g., particularly metatarsal engagement member 66) in an intermetatarsal space.

Embodiments of any instrument described herein (e.g., cutting guide, bone preparation template, bone positioning device) may include or be fabricated from any suitable materials (e.g., metal, plastic). In certain embodiments, an instrument such as a bone positioning device is fabricated at least partially from a radiolucent material such that it is relatively penetrable by X-rays and other forms of radiation, such as thermoplastics and carbon-fiber materials. Such materials are useful for not obstructing visualization of bones using an imaging device when the instrument is positioned on bones.

Another type of bone positioning guide that may be used to move a metatarsal in one or more planes, such as used to move second metatarsal 14 and third metatarsal 16 in at least the transverse plane, is a compressor instrument. For example, when an opening (e.g., wedge-shaped opening) is created at the second and third TMT joints during preparation of the bone ends, a compressor may be attached to the second and/or third metatarsal and another bone, such as the intermediate cuneiform and/or lateral cuneiform, respectively. The compressor may apply a distal-to-proximal force across the second and/or third TMT joints, causing the wedge-shaped opening created across the joint to close. As the wedge-shaped opening closes, the distal end of second metatarsal 14 and/or third metatarsal 16 can pivot in the transverse plane. When used, the compressor may also compress the ends of the bone faces together, e.g., by compressing intermediate cuneiform 28 and second metatarsal 14 together and/or compressing lateral cuneiform 30 and third metatarsal 16 together, to facilitate subsequent fusion.

Figure 7B:
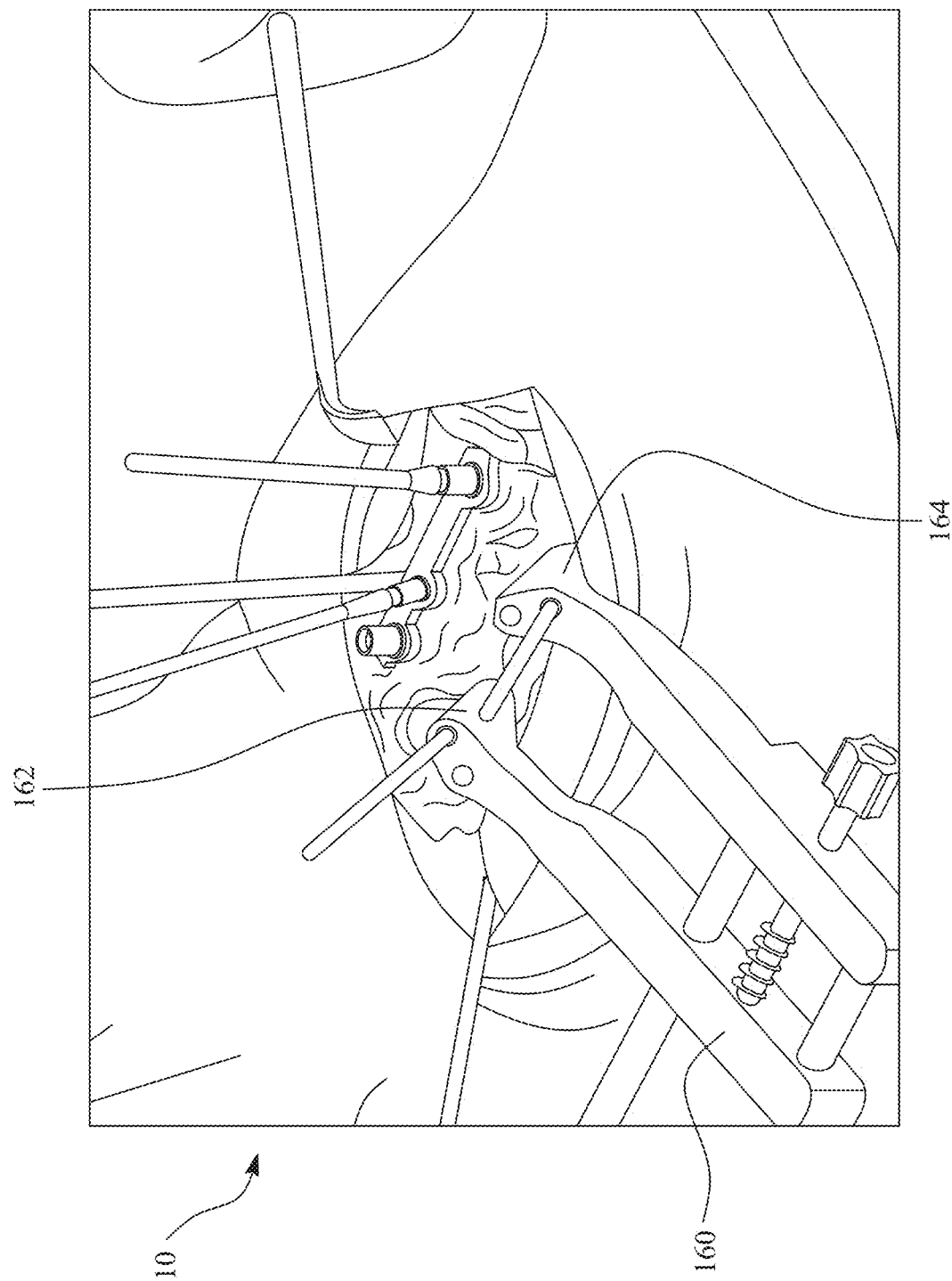
FIG. 7B is an illustration of an example compressor engaged with a foot to facilitate movement of the second and third metatarsals.

FIG. 7B is an illustration of an example compressor instrument 160 engaged with foot 10 to facilitate movement of the second and third metatarsals. In this example, compressor instrument 160 has a first end 162 engaged with the second metatarsal and a second end 164 engaged with the intermediate cuneiform. In particular, in the illustrated arrangement, first and second ends 162, 164 of compressor instrument 160 are illustrated as being pinned to the bones. Compressor instrument 160 can be actuated by the clinician to move the first and second ends 162, 164 of the compressor towards each other. This can cause the ends of the second metatarsal and intermediate cuneiform to which the compressor is attached to draw towards each other, closing a wedge-shaped opening in the TMT joint space and causing a distal end of the second metatarsal to translate laterally. The force applied across the second TMT joint as illustrated in FIG. 7 can also close a wedge-shaped opening in the third TMT joint, and may move the second and third metatarsals as a bone group. In turn, this can cause the fourth and fifth metatarsals to also move in at least the transverse plane, reducing their metatarsus adductus angle.

Additional details on example compressor structures that may be used in accordance with the disclosure are described in US Patent Publication No. 2020/0015856, filed Jul. 11, 2019, and titled "COMPRESSOR-DISTRACTOR FOR ANGULARLY REALIGNING BONE PORTIONS," the entire contents of which are incorporated herein by reference. Further, while the example compressor instrument 160 in FIG. 7B is illustrated as being attached across the second TMT joint, the compressor may additionally or alternatively be attached across the third TMT joint (e.g., with first end 162 attached to third metatarsal 16 and second end 164 attached to lateral cuneiform 30) or yet other set of bones (e.g., across the fourth TMT joint 40, across the fifth TMT joint 42).

With additional reference to FIG. 4, the example technique is illustrated as including a step of provisionally fixating the moved position of the second metatarsal and the third metatarsal (112). For example, after moving the second metatarsal and third metatarsal into a desired realigned position in one or more planes, such as the transverse plane (which may also involve moving the fourth metatarsal and fifth metatarsal), the clinician may optionally provisionally fixate the moved position. Provisional fixation can hold the moved position of one or more bones to facilitate subsequent surgical steps, such as application of one or more permanent fixation devices and/or the performance of additional surgical steps (e.g., first metatarsal realignment).

To provisionally fixate the moved position of the one or more bones, the clinician may insert one or more pins into and/or through a moved bone and into an adjacent bone. For example, the clinician may insert a pin through the second metatarsal and into an adjacent bone (e.g., a cuneiform) and/or insert a pin through the third metatarsal and into an adjacent bone. The pin may be in the form of a rod and/or a wire (K-wire), and may or may not be configured to apply compression across a joint between the bones in which the pin is inserted, e.g., by having an enlarged region of the pin that presses against the outer surface of the bone through which the tip of the pin is inserted, thereby applying compression.

Figure 8A:
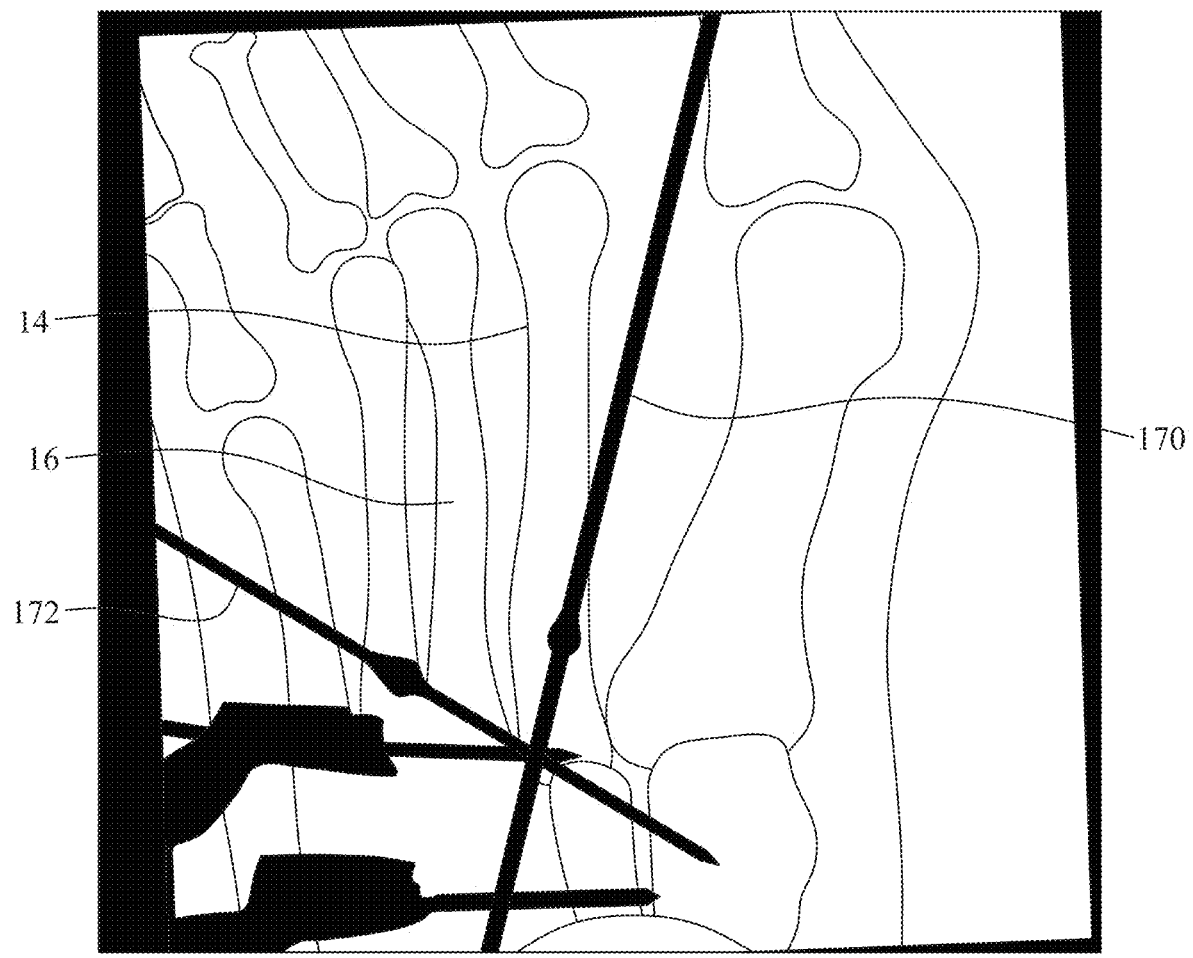
FIG. 8A is a dorsal view of an example radiographic image illustrating an example provisional fixation pin arrangement.

FIG. 8A is a dorsal view of an example radiographic image illustrating an example provisional fixation pin arrangement. In this example, a first fixation pin 170 is inserted into and through the distal base of second metatarsal 14 and into the lateral cuneiform. A second fixation pin 172 is inserted into and through the distal base of third metatarsal 16 and into the intermediate cuneiform.

Figure 8B:
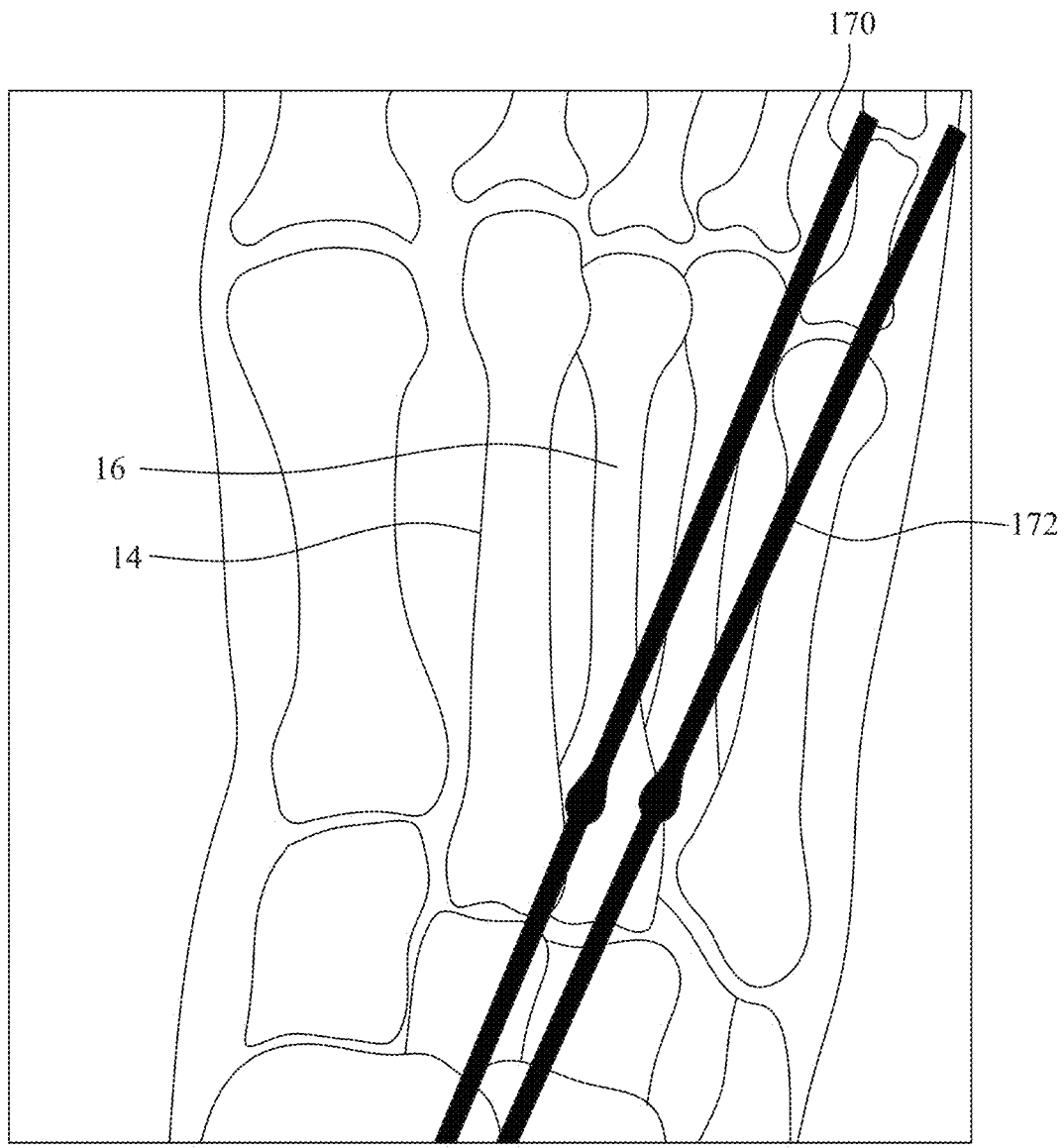
FIG. 8B is a dorsal view of an example radiographic image illustrating another example provisional fixation pin arrangement.

In the illustrated configuration, the first and second pins 170, 172 are shown as crossing, with the shaft of first fixation pin 170 extending in a proximal medial to distal lateral orientation and the shaft of second fixation pin 172 extending in a proximal lateral to distal medial orientation. In other cases, first and second pins 170, 172 may not cross but may instead be orientated in parallel, such as with the shafts of both pins extending in a distal medial to proximal lateral orientation. FIG. 8B is a dorsal view of another example radiographic image illustrating a provisional fixation pin arrangement in which first and second pins 170, 172 are both positioned extending in a proximal medial to distal lateral orientation.

The clinician may use a different number, configuration, and/or positioning of fixation pins. For example, depending on the number of TMT joints being prepared, the clinician may insert a provisional fixation pin through the end of one or more of second metatarsal 14, third metatarsal 16, fourth metatarsal 18, and/or fifth metatarsal 20, with the pin extending into and/or through the end of the metatarsal and also into another bone, such as an opposed cuneiform and/or cuboid bone. Additionally or alternatively, the clinician may insert a provisional fixation pin through a side of one metatarsal being fixated (e.g., a medial side, lateral side) into an adjacent metatarsal).

Independent of whether the clinician deploys a provisional fixation device, the clinician may apply one or more permanent fixation devices to facilitate fusion of the second and third TMT joints following reduction of the metatarsus adduction angle (step 114 in FIG. 4). The one or more fixation devices can extend across the second and/or third TMT joints to secure and hold opposed bone ends together for fusion (and/or other TMT joint in instances in which a different TMT joint is prepared for fusion). For example, the clinician may apply a first fixation device across the second TMT joint and apply a second fixation device across the third TMT joint.

A bone fixation device may be any feature or combination of features that holds two bone portions in fixed relationship to each other to facilitate fusion of the bone portions during subsequent healing. Any one or more bone fixation devices that can be used include, but are not limited to, a bone screw (e.g., a compressing bone screw), a bone plate, a bone staple, an external fixator, an intramedullary implant, and/or combinations thereof. Depending on the type of bone fixation device selected, the bone fixation device may be attached to external surfaces of the bone portions being fixated or may be installed as an intramedullary device internal to the bone portions.

In one example, the clinician may install a first bone plate across the second TMT joint. The first bone plate can be secured on one side to second metatarsal 14, bridge the second TMT joint, and be secured on an opposite side to intermediate cuneiform 28. The clinician may install a second bone plate across the third TMT joint. The second bone plate can be secured on one side to third metatarsal 16, bridge the third TMT joint, and be secured on an opposite side to lateral cuneiform 30. Additionally or alternatively, the clinician may apply a U-shaped plate or other shaped plate bridging both the second and third TMT joint (e.g., with the U-shaped plate attached to the intermediate and lateral cuneiforms on the base of the U-shape and the legs of the U-shape being attached to the metatarsals). Independent of the number of plates used, each bone plate may be secured to an underlying bone using one or more screws, staples, and/or other securing mechanisms. When using a bone plate, each bone plate may be linear or may have a non-linear shape, such as a Y-shape, an L-shape, a T-shape, a U-shape, and/or other shape profile. It should be appreciated that, in this document, when terms "first" and "second" are used to modify a noun, such use is simply intended distinguish one item from another and is not intended to require a sequential order of preforming a procedure step unless specifically stated.

As briefly discussed above, a metatarsus adduction deformity may present with a hallux valgus misalignment in some patients. Accordingly, a clinician performing a metatarsus adduction correction procedure may also perform a hallux valgus correction on the patient undergoing treatment. In the example FIG. 4, the example technique is illustrated as including a first metatarsal realignment step (116). Although the technique of FIG. 4 illustrates the first metatarsal realignment being performed after reduction and permanent fixation of the second and third TMT joints, a different surgical order may be performed. For example, the first metatarsal may be realigned prior to moving a lesser metatarsal (e.g., the second and third metatarsals), or may be realigned after moving the lesser metatarsal (e.g., the second and third metatarsals) but prior to permanently fixating the lesser TMT joint(s).

While the order of the surgical procedure may vary, in some applications, it is useful to correct the alignment of one or more lesser metatarsals (e.g., second and/or third metatarsals) prior to correcting the alignment of the first metatarsal. By initially correcting the position of the lesser metatarsal, such as the second and third metatarsals (and, in some examples, also correcting the position of the fourth and fifth metatarsals), the clinician may be able to better anatomically realign the first metatarsal relative to the aligned lesser metatarsals. Correction of the alignment of one or more of the lesser metatarsals may change the extent of misalignment of the first metatarsal, which can then be further corrected during a subsequent first metatarsal realignment step.

To correct the alignment of first metatarsal 12, the clinician may surgically access the first TMT joint as discussed above. Once accessed the clinician may prepare an end of first metatarsal 12 and an opposed end of medial cuneiform 26. The clinician may prepare the ends of the bones with or without cutting, as discussed above with respect to preparation of the ends of second metatarsal 14 and third metatarsal 16 (e.g., using any preparation technique discussed herein). In instances in which the clinician prepares one or more bone ends using a cutting instrument, the clinician may or may not utilize a cut guide to guide controlled cutting of the bone ends and/or a bone preparation template to indicate where bone preparation should be performed.

Either before or after preparing one or both ends of first metatarsal 12 and medial cuneiform 26, the clinician may move first metatarsal 12 in at least one plane (e.g., the transverse plane, the frontal plane) to close an intermetatarsal angle between the first metatarsal and second metatarsal 14. In some examples, the clinician moves the first metatarsal in multiple planes, such as the transverse plane and/or frontal plane and/or sagittal plane. The clinician may or may not utilize a bone positioning guide to facilitate movement of the first metatarsal relative to the second metatarsal and/or medial cuneiform. With the first metatarsal moved to a desired position, the clinician can optionally provisionally fixate the moved position of the first metatarsal and then permanently fixate the moved position using one or more bone fixation devices, such as those described above. Additional details on example first metatarsal realignment instruments and techniques that can be used are described in U.S. Pat. No. 9,622,805, issued Apr. 18, 2017 and entitled "BONE POSITIONING AND PREPARING GUIDE SYSTEMS AND METHODS."

Figure 9B:
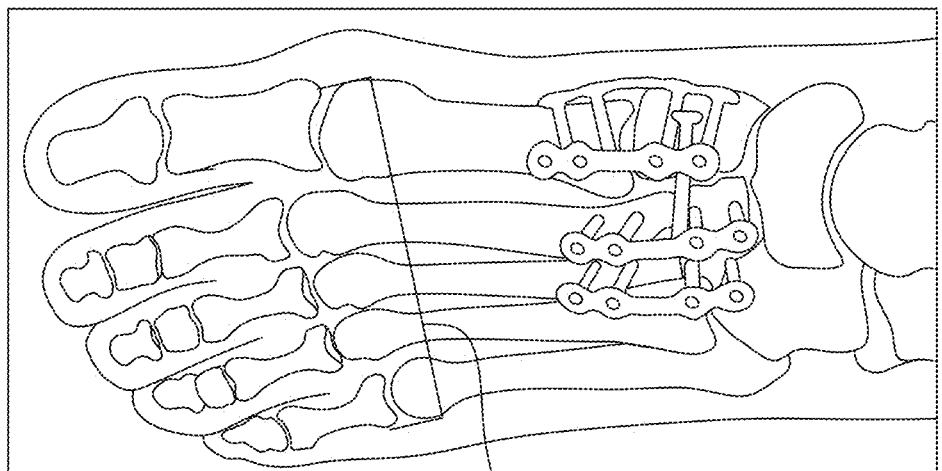
FIGS. 9A and 9B are dorsal radiographic images of an example foot before and after a treatment procedure, respectively, performed following a surgical technique discussed with respect to FIG. 4.
Figure 9A:
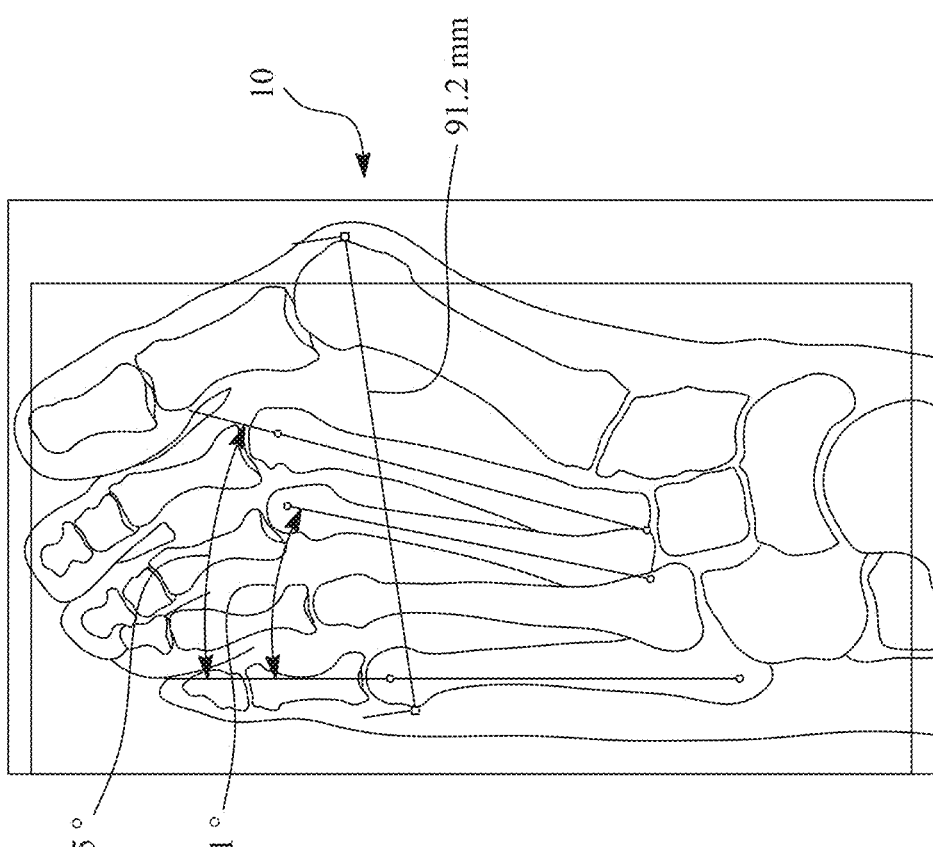

FIGS. 9A and 9B are dorsal radiographic images of an example foot 10 before and after a treatment procedure, respectively, performed following an example surgical technique discussed above with respect to FIG. 4. FIG. 9A illustrates foot 10 with metatarsus adductus and hallux valgus deformities. FIG. 9B illustrates foot 10 after realignment of the second and third metatarsals in at least the transverse plane and multiplanar correction of the first metatarsal in all three planes. FIG. 9B illustrates three bone plates applied across the first, second, and third TMT joints to facilitate fusion across the three joints.

While the technique of FIG. 4 has generally been described with reference to preparation of second TMT joint 36 and third TMT joint 38 and movement of both second metatarsal 14 and third metatarsal 16 (optionally in combination with movement of fourth metatarsal 18 and fifth metatarsal 20), the techniques and/or devices may be performed on single TMT joints and/or different TMT joints without departing from the scope of the disclosure. For example, the technique of FIG. 4 may be performed on a single lesser TMT joint, such as only the second TMT joint 36, only the third TMT joint 38, only the fourth TMT joint 40, or only the fifth TMT joint 42, in each case optionally in combination with preparation of the first TMT joint 34 and realignment of the first metatarsal. Other combinations of joint preparation are also possible.

In applications where the clinician prepares only a single lesser TMT joint for fusion (again, optionally as part of a procedure that also prepares the first TMT joint), the clinician may move the lesser metatarsal associated with that TMT joint in one or more planes, e.g., using devices and/or techniques discussed herein. Repositioning of the metatarsal associated with the lesser TMT joint being prepared may or may not also move one or more adjacent metatarsals to the lesser metatarsal being moved through ligamentous tissue. For example, if the clinician prepares second TMT joint 36 and moves second metatarsal 14, the repositioning of the second metatarsal may cause realignment of third metatarsal 16, fourth metatarsal 18, and/or fifth metatarsal 20.

As discussed above, a bone realignment technique according to the disclosure may involve cutting an end of a cuneiform and/or an end of an opposed metatarsal. In such applications, the clinician may perform the cuts freehand or with the aid of one or more cut guides (also referred to herein interchangeably as a cutting guide). The use of a cut guide may facilitate more accurate and repeatable cuts patient-to-patient, promoting more consistent clinical outcomes across a range of patients an anatomical deformities. When a cut guide is used, the cut guide may generally define at least one guide surface positionable over a side of the bone to be cut, such as a dorsal side. The clinician can place a cutting instrument adjacent to, and optionally in contact with, the guide surface and translate the cutting instrument relative to the guide surface to perform a cut in a plane parallel to the guide surface. For example, the clinician may place the cutting instrument in contact with the guide surface and then translate the cutting instrument relative to the guide surface, e.g., plantarly into a bone and/or in a medial or lateral direction. The guide surface may bound movement of the cutting instrument to a desired direction of cutting.

Figure 10:
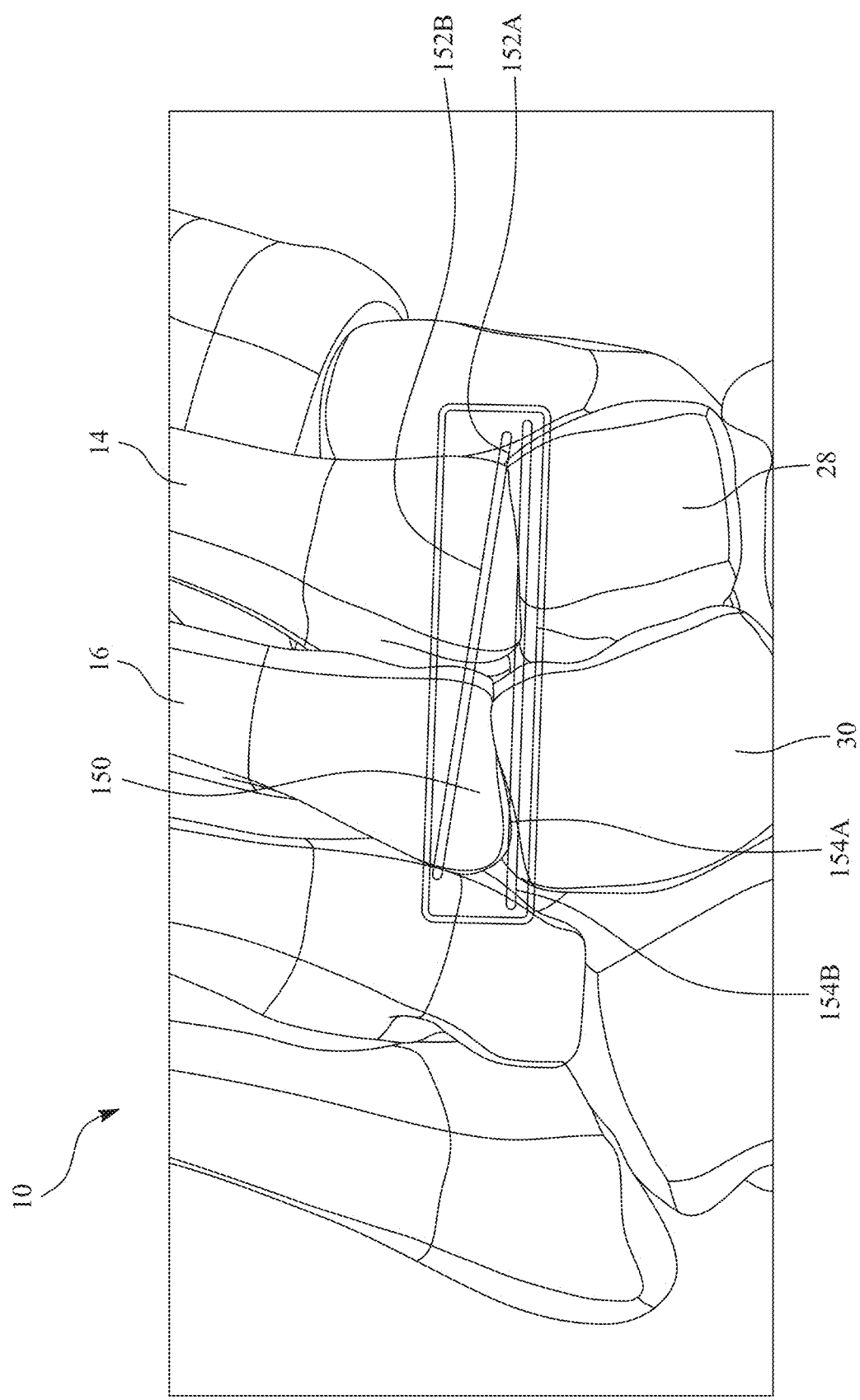
FIG. 10 is a top view of a foot showing the example cut guide introduced with respect to FIG. 5A.

FIG. 10 is a top view of foot 10 showing the example cut guide 150 introduced with respect to FIG. 5A above. Cut guide 150 includes at least one guide surface positionable over a dorsal side of a bone to be cut. For example, cut guide 150 includes a guide surface 152A positionable over a dorsal side of second metatarsal 14 and third metatarsal 16. Guide surface 152A can extend straight (e.g., parallel) or an angle in a dorsal to plantar direction (in other words, in the sagittal plane) and can guide the cutting tool in a direction defined by the guide surface. In use, the clinician can place a cutting tool in abutting relationship with guide surface 152A and advance the cutting tool relative to the guide surface to remove an end of the metatarsal being cut (e.g., second metatarsal 14 and/or third metatarsal 16).

In some examples, cut guide 150 defines a single guide surface. In other examples, cut guide 150 may include multiple guide surfaces, for example spaced apart from each other to define a cutting slot between the guide surfaces. In the illustrated example, cut guide 150 is shown having first metatarsal-side guide surface 152A and a second metatarsal-side guide surface 152B parallel to the first guide surface to define a cutting slot between the two guide surfaces. A clinician can insert a cutting tool, such as a saw blade, in the cutting slot to guide removal of a portion of the end of second metatarsal 14 and a portion of the end of third metatarsal 16.

As discussed above with respect to FIG. 4, a clinician may independently prepare one or more lesser metatarsals (e.g., second metatarsal 14 and third metatarsal 16) and/or may prepare the ends of one or more lesser metatarsals together, e.g., by making a continuous cut transecting two metatarsals. In applications where the clinician desires to make a continuous cut transecting the two metatarsals, cut guide 150 may be configured with a guide surface 152A (or pair of guide surfaces 152A, 152B as illustrated) extending across multiple metatarsals, such as both second metatarsal 14 and third metatarsal 16. For example, the guide surface may define a continuous guide surface extending from a medial-most side of the second metatarsal 14 to a lateral-most side of third metatarsal 16. This can allow the clinician to utilize the guide surface to cut through an entirety of the second and third metatarsals in the medial to lateral direction. When so configured, the guide surface (e.g., cutting slot) may be sized to terminate at the medial-most side of the second metatarsal 14 and/or the lateral-most side of third metatarsal 16 or may extend past such boundary locations. Oversizing the guide surface may allow cut guide 150 to be used on broader patient population set. However, oversizing the guide surface may require closer clinician attention when making one or more cuts utilizing the guide surface.

Figure 11:
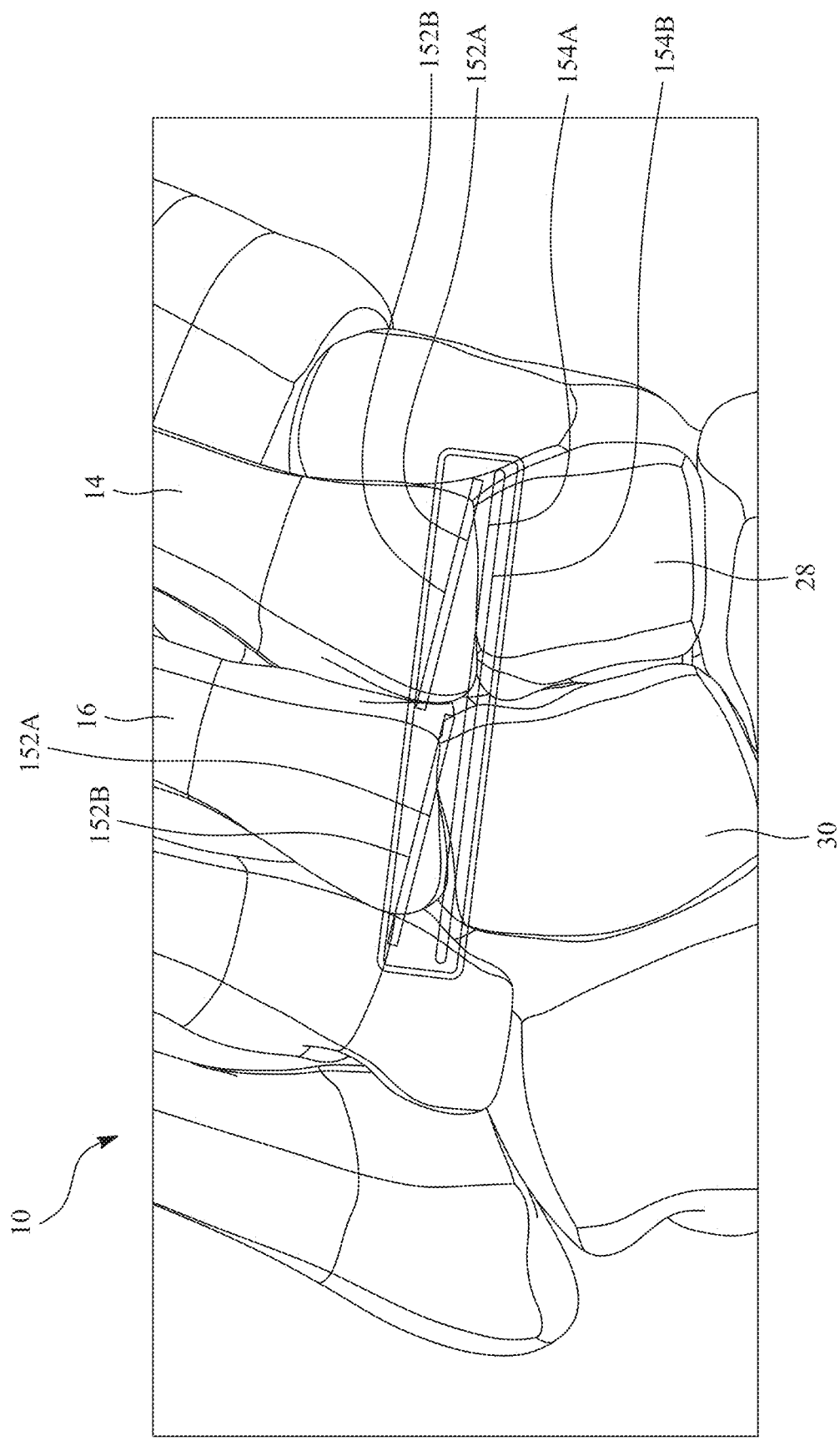
FIG. 11 is a top view of a foot showing another example configuration of a cut guide.

FIG. 11 is a top view of foot 10 showing another example configuration of cut guide 150 in which the cut guide is not configured with a continuous guide surface extending across multiple metatarsals (e.g., second metatarsal 14 and third metatarsal 16) but instead has a discontinuous guide surface, or two guide surfaces, separately positionable over each of the metatarsals. When so configured, cut guide 150 may have a guide surface region positionable over each of two lesser metatarsals (e.g. second metatarsal 14 and third metatarsal 16) but a discontinuity or break between the guide surface regions that prevents a continuous cut from being made that transects both metatarsals. One guide surface may extend from a medial to a lateral side of one lesser metatarsal (e.g., second metatarsal 14), while another guide surface may extend from a medial to a lateral side of another lesser metatarsal (e.g., third metatarsal 16). A parallel and offset guide surface 152B may be provided to define a cutting slot, e.g., a cut slot over the second metatarsal and/or third metatarsal.

With further reference to FIGS. 10 and 11, cut guide 150 is illustrated as also having a guide surface 154A positionable over a dorsal side of intermediate cuneiform 28 and lateral cuneiform 30. Guide surface 154A can extend straight (e.g., parallel) or an angle in a dorsal to plantar direction (in the sagittal plane) and can guide the cutting tool in a plane parallel to the guide surface. In use, the clinician can place a cutting tool in abutting relationship with guide surface 154A and advance the cutting tool relative to the guide surface to remove an end of an opposed cuneiform/cuboid bone, such as intermediate cuneiform 28 and lateral cuneiform 30.

As with the metatarsal-side guide surface 152A, the cuneiform-side guide surface 154A may define a single guide surface or may include multiple guide surfaces, for example spaced apart from each other to define a cutting slot between the guide surfaces. In the illustrated example, cut guide 150 is shown having first cuneiform-side guide surface 154A and a second cuneiform-side guide surface 154B parallel to the first guide surface to define a cutting slot between the two guide surfaces. A clinician can insert a cutting tool, such as a saw blade, in the cutting slot to guide removal of a portion of the end of intermediate cuneiform 28 and lateral cuneiform 30.

In some examples, the cuneiform-side guide surface 154A (or pair of guide surfaces 154A, 154B as illustrated) extends across both intermediate cuneiform 28 and lateral cuneiform 30. For example, the guide surface may define a continuous guide surface extending from a medial-most side of intermediate cuneiform 28 to a lateral-most side of lateral cuneiform 30. This can allow the clinician to utilize the guide surface to perform a continuous cut to cut an end portion of both the intermediate cuneiform and the lateral cuneiform. When so configured, the guide surface (e.g., cutting slot) may be sized to terminate at the medial-most side of intermediate cuneiform 28 and the lateral-most side of lateral cuneiform 30 or may extend past such boundary locations to be oversized.

In other examples, the cut guide is not configured with a continuous guide surface extending across intermediate cuneiform 28 and lateral cuneiform 30 but instead has a discontinuous guide surface, or two guide surfaces, separately positionable over each of the cuneiform and/or cuboid bones. When so configured, cut guide 150 may have a guide surface region positionable over each of multiple bones, such as intermediate cuneiforms 28 and lateral cuneiform 30, but a discontinuity or break between the guide surface regions that prevents a continuous cut from being made that transects both cuneiforms. One guide surface may extend from a medial to a lateral side of intermediate cuneiform 28, while another guide surface may extend from a medial to a lateral side of lateral cuneiform 30. A parallel and offset guide surface 154B may be provided to define a cutting slot, e.g., a cut slot over the intermediate cuneiform and/or lateral cuneiform.

While cut guide 150 is illustrated as having both a metatarsal-side guide surface 152A and a cuneiform-side guide surface 154A, in alternative implementations, the cut guide may be configured with a guide surface for only cutting one or more metatarsals and/or one or more cuneiform/cuboid bones. One or more separate cut guides may be utilized to cut the other of the metatarsal(s) or cuneiform(s). Alternatively, the clinician may perform cutting freehand or may perform a bone preparation step that does not involve cutting the bone(s).

Figure 12A:
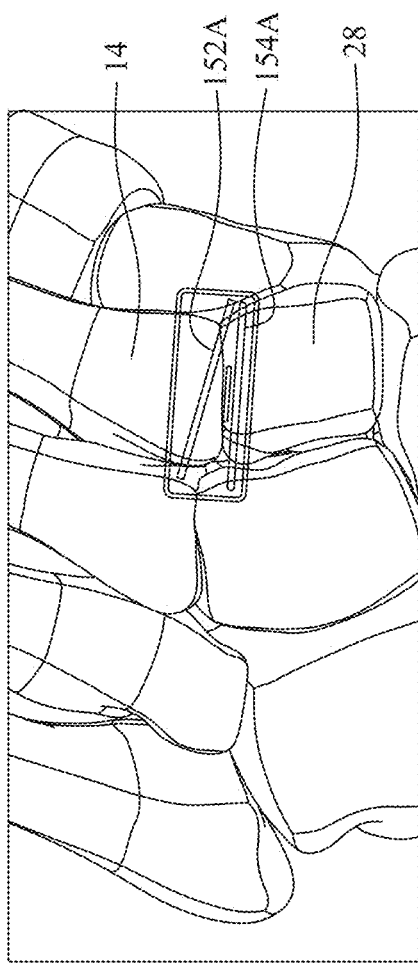
FIGS. 12A and 12B are top views of a foot showing another example configuration of a cut guide.
Figure 12B:
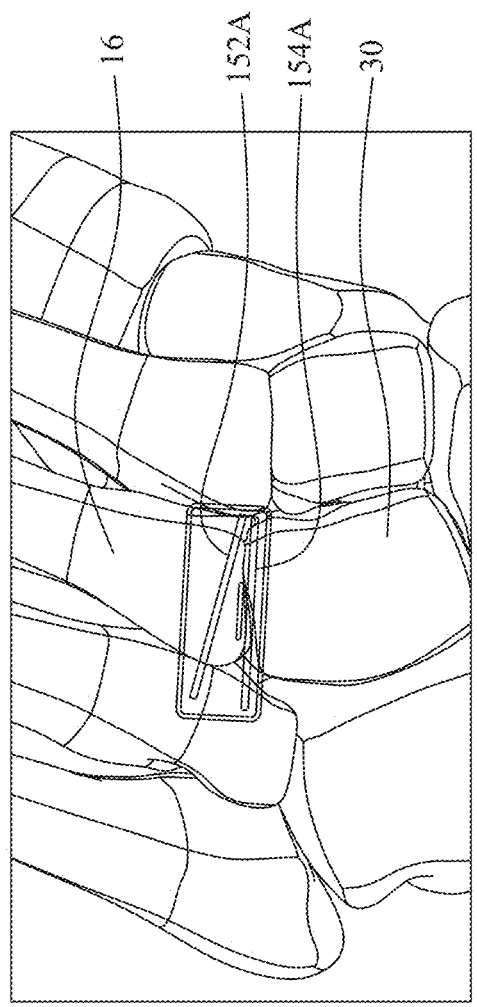

As still another example, cut guide may be configured to be positioned across a single TMT joint to cut a single metatarsal and/or cuneiform instead of being configured to be positioned across multiple metatarsals and/or cuneiforms. FIGS. 12A and 12B are top views of foot 10 showing an alternative configuration of cut guide 150 where the cut guide is configured (e.g., sized and/or shaped) to be positioned across the second TMT joint and the third TMT joint, respectively. A cut guide configured to be positioned across another lesser TMT joint (the fourth TMT joint, fifth TMT joint) can also be provided.

As shown in FIG. 12A, cut guide 150 has a metatarsal-side guide surface 152A (which is illustrated as a cutting slot) extending from a medial-most side of second metatarsal 14 to a lateral-most side of the metatarsal. The cut guide also has a cuneiform-side guide surface 154A (which is also illustrated as a cutting slot) extending from a medial-most side of intermediate cuneiform 28 to a lateral-most side of the cuneiform.

With reference to FIG. 12B, cut guide 150 is illustrated with a metatarsal-side guide surface 152A (which is illustrated as a cutting slot) extending from a medial-most side of third metatarsal 16 to a lateral-most side of the metatarsal. The cut guide also has a cuneiform-side guide surface 154A (which is also illustrated as a cutting slot) extending from a medial-most side of lateral cuneiform 30 to a lateral-most side of the cuneiform.

Cut guide 150 in FIGS. 12A and 12B may be the same cut guide that is moved between the second TMT joint to the third TMT joint. Alternatively, the clinician may have two identical cut guides 150 that are utilized on the different TMT joints. In still further applications, two different cut guides 150 may be provided that are configured differently for the second TMT joint in the third TMT joint, respectively. The cut guides may be configured differently by having different sizes and/or shapes, such as different angular orientations of guide surfaces.

In configurations where cut guide 150 has both a metatarsal-side guide surface and an opposed bone-side guide surface (e.g., cuneiform-side guide surface), the guide surfaces may be parallel to each other, angled relative to each other (e.g., to define a wedge-shaped region), or otherwise oriented relative to each other to achieve desired cut patterns. When using an angled guide surface arrangement, the relative angle between the two guide surfaces can define the size and shape of bone wedge removed utilizing cut guide 150. In some examples, the angle between the metatarsal-side guide surface and the cuneiform-side guide surface is fixed. In other words, the angle between the metatarsal-side guide surface and the cuneiform-side guide surface is set during the design and manufacturing of the cut guide and cannot be varied by the clinician. In these examples, the clinician may be provided with a system having a plurality of cut guides 150 (e.g., two, three, four, five, or more), where each cut guide defines different angles between guide surfaces. The clinician can select a cut guide with desired angle from the system of different guides based on the needs of the particular patient undergoing a procedure. In other examples, however, the angle between the metatarsal-side guide surface and the cuneiform-side guide surface may be adjustable. This can provide the clinician with flexibility to adjust the angular orientation between the metatarsal-side guide surface and the cuneiform-side guide surface for patient-specific anatomical considerations.

Figure 13:
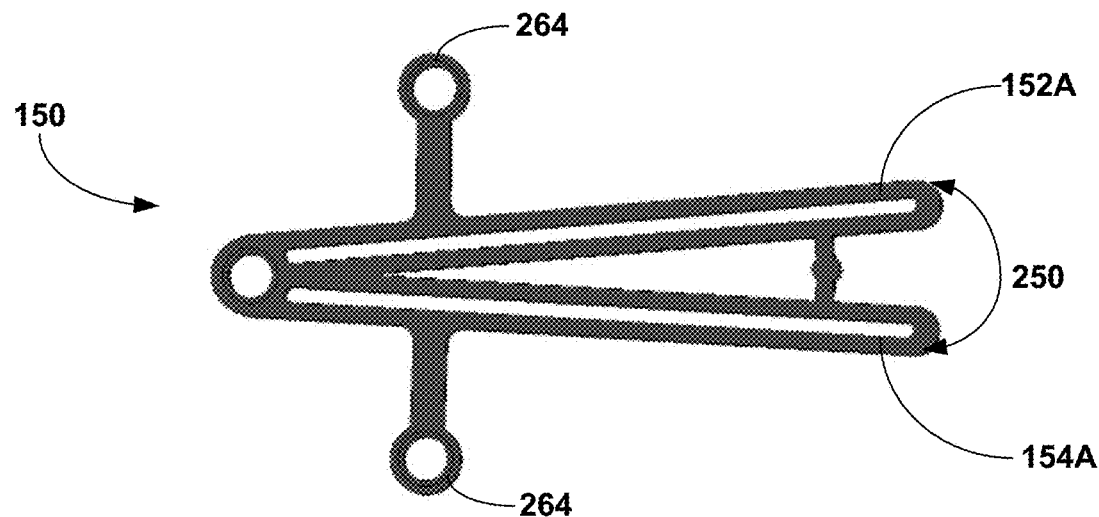
FIG. 13 is a top view of an example configuration of a cut guide in which an angle between a distal-most guide surface and a proximal-most guide surface of the guide is fixed.

FIG. 13 is a top view of an example configuration of cut guide 150 in which an angle 250 between a distal-most guide surface 152A of the cut guide (when positioned over a metatarsal) and a proximal-most guide surface 154A of the guide (when positioned over a cuneiform or cuboid) is fixed. For many clinical applications, angle 250 may be less than 75 degrees, such as less than 60 degrees, less than 45 degrees, less than 35 degrees, less than 20 degrees, less than 15 degrees, less than 10 degrees, or less than 5 degrees. For example, angle 250 may range from 1 degree to 20 degrees, such as from approximately 5 degrees to approximately 20 degrees, from approximately 5 degrees to approximately 10 degrees, or from approximately 6 to approximately 9 degrees. In other examples, angle 250 may be 0 degrees (providing parallel guide surfaces) to allow for reciprocal planing, e.g., on mild cases. Bone wedges cut and/or removed according to a surgical technique according to the disclosure may define angles within any of the forgoing angular limits (or yet different limits), whether or not cut using a cut guide according to the disclosure (e.g., including when cut freehand and/or with the aid of a bone preparation template). Further, any cut guide described herein having two guide surfaces angled relative to each other can implement any of the foregoing angles or angle ranges (or yet different limits).

Figure 14A:
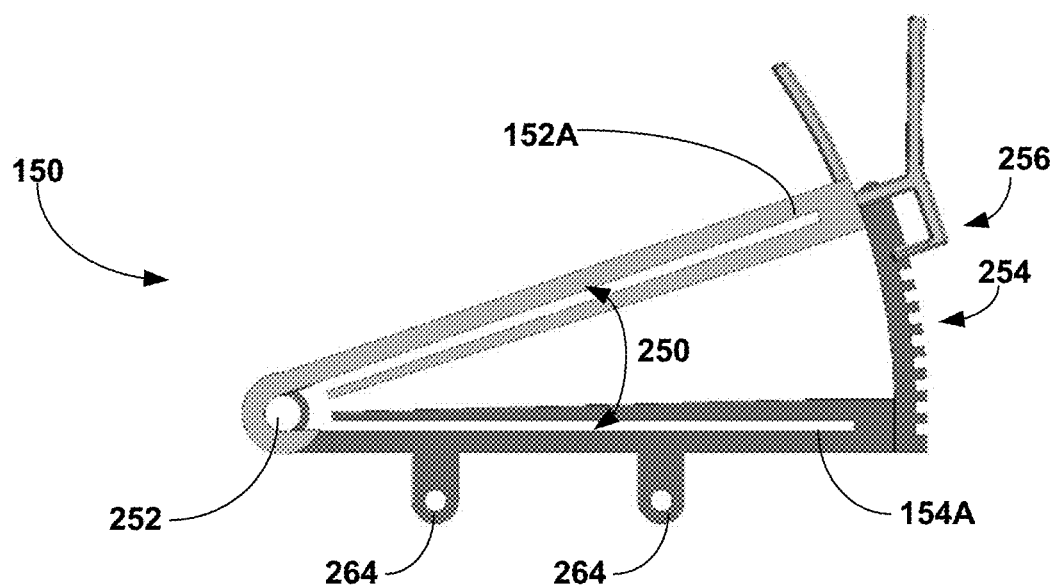
FIG. 14A is a top view of another example configuration of a cut guide in which an angle between a distal-most guide surface of the cut guide and a proximal-most guide surface of the guide is variable.

FIG. 14A is a top view of another example configuration of cut guide 150 in which the angle 250 between a distal-most guide surface 152A of the cut guide (when positioned over a metatarsal) and a proximal-most guide surface 154A of the guide (when positioned over a cuneiform or cuboid) is variable. The two guide surfaces (which, in the illustrated example, are shown as guide slots) can be hingedly or otherwise movably connected together and allowed to rotate relative to each other about a pivot axis 252. The opposite end of the two guide surfaces from pivot axis 252 may or may not be connected together. In the illustrated example, the opposite end of the two guide surfaces are movably connected together via a sliding connection 254. An adjustable cut guide configuration can be adjustable within any of the example ranges of angles discussed above.

A lock 256 may be provided to lock a desired angular orientation of the two guide surfaces relative to each other. Lock 256 may be implemented as a screw or other moving feature that bears against a surface to provide frictional engagement for locking an angular orientation of the guide surfaces. As another example, lock 256 may be a projection or recess that engages one of a series of detents to lock the angular orientation of the guide surfaces. Other features that provide a locking function can be used without departing from the scope of the disclosure. When cut guide 150 is configured without a sliding connection 254 and/or lock 256, one or both of the guide surfaces may have an associated pinhole that allows each guide surface to be pin to an underlying bone for temporarily fixing the position of the guide surface during a surgical procedure. While cut guide 150 in FIG. 14A illustrates one example configuration of implementing an adjustable cut guide, other implementations are possible.

Figure 14B:
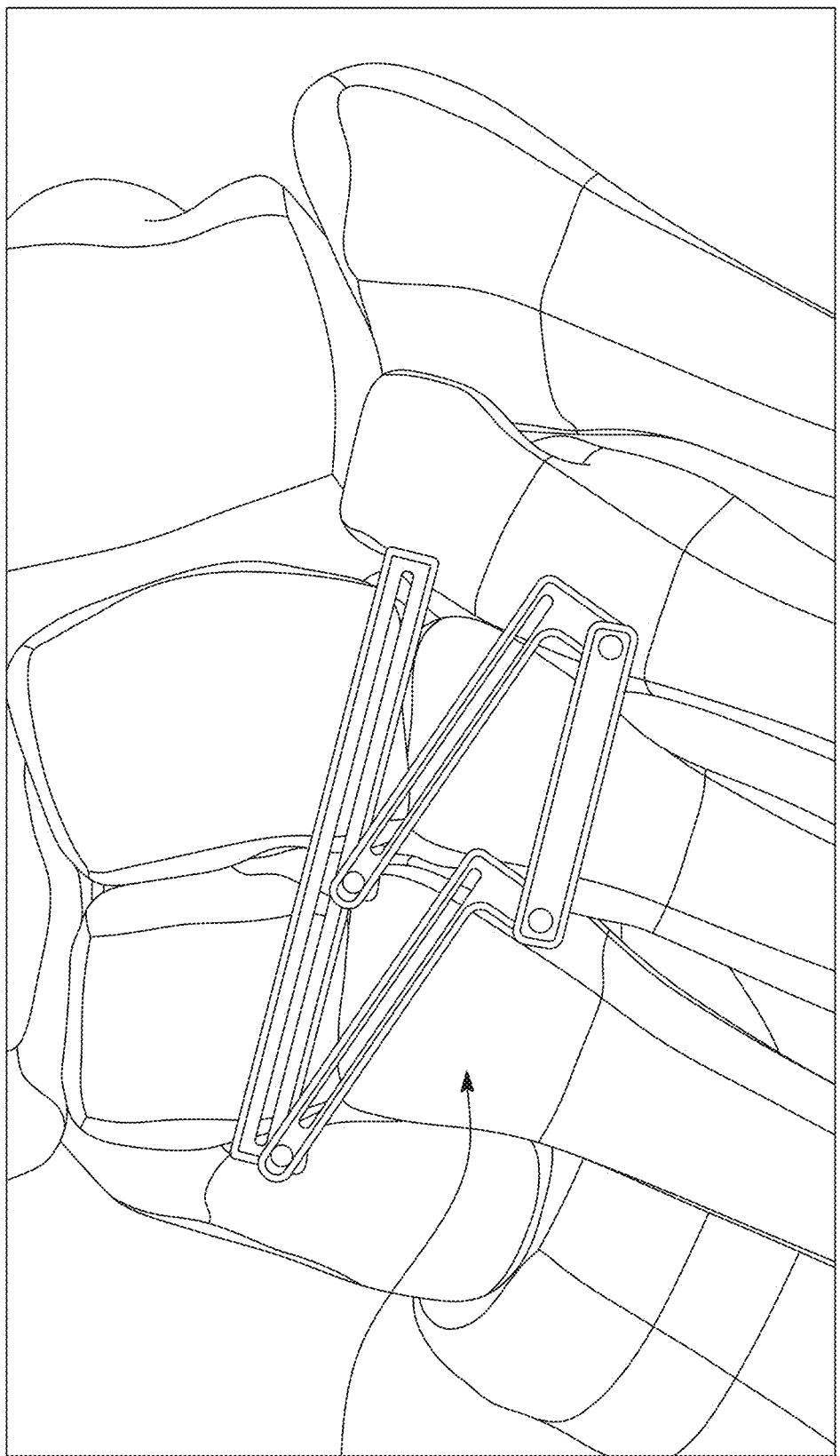
FIG. 14B illustrates an example of cut guide have separate guide surfaces for cutting two metatarsals where the angular position of the guide surfaces are both adjustable.

For example, FIG. 14B illustrates an example of cut guide 150 have separate guide surfaces for cutting the second and third metatarsals where the angular position of the guide surfaces are both adjustable. As illustrated, the two guide surfaces are connected by a joining bar, allowing the angle of the two guide surfaces to be adjusted together (e.g., so that each guide surface defines the same angle). In other examples, the guide surfaces may be independently adjustable (e.g., by omitting the joining bar).

To help facilitate positioning of cut guide 150 over one or more bones to be cut, the cut guide may include one or more locating features. The locating features may be insertable into a bone and/or a joint space between adjacent bones to provide anatomical reference locations for orienting cut guide 150 relative to the anatomy of the foot of the patient undergoing the clinical procedure. For example, cut guide 150 may include one or more pins and/or spacers that are associated with the cut guide and used to help orient the cut guide relative to the anatomy of the patient.

As used in the present disclosure, a locating pin associated with a cutting guide generally refers to a feature that is inserted into a bone and can be used to help position the cutting guide relative to a bone to be cut. By contrast, a spacer associated with the cutting guide generally refers to a feature that is inserted into a joint space between adjacent bones and can be used to help position the cutting guide relative to a bone to be cut. Each feature described as a locating pin or spacer may have any appropriate size and cross-sectional shape, including arcuate shapes (e.g., circular, oval), polygonal shapes (e.g., square, rectangular, T-shaped), and/or combinations of arcuate and polygonal shapes. The term locating feature encompasses both a locating pin and/or spacer. Each locating feature may have a shaft insertable into a bone and/or joint space.

When cut guide 150 includes one or more associated pins and/or spacers, such features can be integral with (e.g., permanently connected to) the body of the cut guide or can be detachable and separable from the cut guide. Configuring cut guide 150 to be used with at least one locating feature, e.g., spacer and/or pin that can be separately installed in a joint space between bones or in a bone, respectively, can be useful. When so configured, the spacer and/or pin may be installed independently of the cut guide into a bone structure and the cut guide then engaged with the inserted spacer and/or pin. For example, the cut guide may be slide down on the locating feature, attached to a side of the locating feature, or otherwise operatively connected to the locating feature. Once the cut guide is installed on the locating feature, the connection between the cut guide and locating feature may be fixed (e.g., preventing relative movement between the two features) or may be a relatively movable connection (e.g., allowing rotation or other relative movement between the two features). In either case, the spacer and/or pin can be used to identify an anatomical landmark for positioning cut guide 150 and the cut guide then engaged with the spacer and/or pin.

Figure 15:
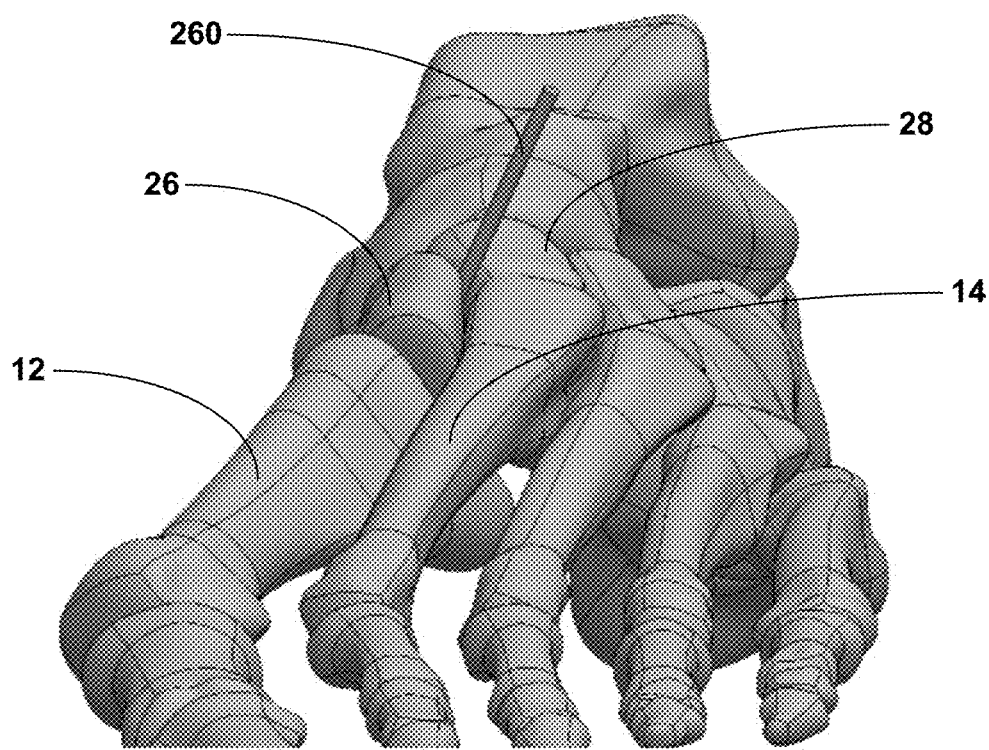
FIG. 15 is a perspective view of a foot illustrating an example locating feature that can be used with a cut guide.
Figure 16:
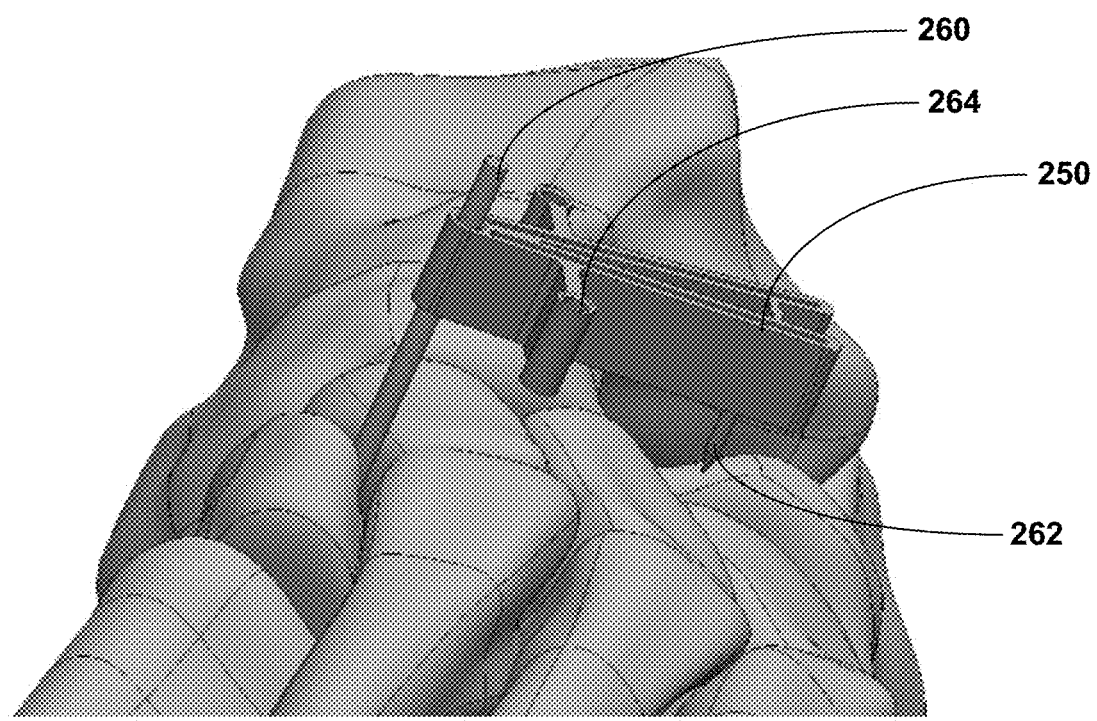
FIG. 16 illustrates an example cut guide engaged with and being advanced plantarly along a locating feature to help orient the bone guide over one or more bones to be cut.

FIG. 15 is a perspective view of foot 10 illustrating an example locating feature 260, illustrated in the form of a spacer, that can be used with cut guide 150. In use, the clinician can insert locating feature 260 in a joint space between adjacent bones and then engage bone cutting guide 150 with the locating feature, e.g., by sliding the bone cutting guide down onto the spacer. In the specific example of FIG. 15, locating feature 260 is illustrated as being inserted into the joint space between the medial cuneiform 26 and intermediate cuneiform 28. FIG. 16 illustrates cut guide 150 being engaged with and being advanced plantarly along locating feature 260 to help orient the bone guide over one or more bones to be cut. In particular, in the example of FIG. 16, cut guide 150 is illustrated as being oriented over a dorsal surface of both the second and third metatarsals as well as the intermediate and lateral cuneiforms.

As noted above, cut guide 150 can have one or more associated pins and/or spacers, each of which can be permanently affixed to and/or separable from the body of the cut guide. In FIG. 16, cut guide 150 is illustrated as including a first locating feature 260 from which the body of the cut guide is separable as well as a second locating feature 262, also illustrated in the form of a spacer, that is permanently affixed to the body of a cut guide. Second locating feature 262 is positioned on a different portion of the cut guide, specifically the lateral half of the cut guide in the illustrated example. As cut guide 150 is engaged with first locating feature 260 (e.g., by being advanced plantarly down on locating feature 260), the clinician may rotate the cut guide about locating feature 260 in the transverse plane to position the second locating feature 262 over a target insertion location. The target insertion location may be the third TMT joint space, as illustrated, or any other joint space and/or bone insertion location.

Cut guide 150 according to the disclosure can include any suitable number of locating features, which can be permanently affixed to and/or separable from the body of the cut guide. For example, cut guide 150 may include a single locating feature or multiple locating features (e.g., two, three, or more). When configured with one or multiple locating features, the one or more locating features may be arranged at different locations along the body of the cut guide.

For example, one locating feature may be on a medial-most half (e.g., medial-most quarter) of the cut guide and/or one locating feature may be on a lateral-most half (e.g., lateral-most quarter) of the cut guide, when the cut guide is positioned over bones to be cut. Additionally or alternatively, one such locating feature may be on a distal side of the cut guide (e.g., distal of a TMT joint when the cut guide is positioned over the joint) and/or one locating feature may be on a proximal side of the cut guide (e.g., proximal of a TMT joint when the cut guide is positioned over the joint). In use, the clinician may rotate cut guide 150 with an attached locating feature and/or about a locating feature to adjust an alignment of one or more guide surfaces relative to one or more bones to be cut. In some examples, the cut guide (e.g., guide surface associated therewith) has a length extending from a first end to a second end, and a locating feature is positioned at or adjacent an end of the guide to allow the guide to rotate thereabout.

The one or more locating features associated with cut guide 150 can be positioned in any desired bones and/or joint spaces suitable for positioning the cut guide over one or more target bones to be cut. Correspondingly, cut guide 150 can be configured (e.g., sized and/or shaped) to position one or more guide surfaces of the cut guide over one or more target bones to be cut, when the one or more locating features are positioned at their target location and the cut guide is engaged therewith.

FIGS. 23A-23I illustrate example target locations on the foot for inserting one or more locating features associated with cut guide 150 to position the cut guide over one or more bones to be cut. The clinician can insert the shaft of a locating feature into the indicated joint space, e.g., with cut guide 150 attached thereto and/or with the cut guide engageable to the locating feature after being inserted into the joint space. While each of FIGS. 23A-23I illustrate a single joint space location for inserting a locating feature associated with cut guide 150, any combination of two or more of the illustrated joint space locations may be utilized in combination (e.g., for cut guides employing multiple locating features). Each locating feature of cut guide 150 may be configured (e.g., sized and/or shaped) to be positioned in a specific targeted bone and/or joint space.

Figure 23A:
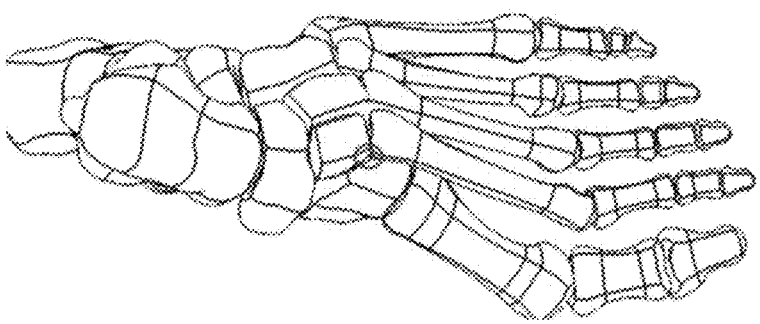
FIGS. 23A-23I illustrate example target locations on the foot for inserting one or more locating features associated with a cut guide.
Figure 23B:
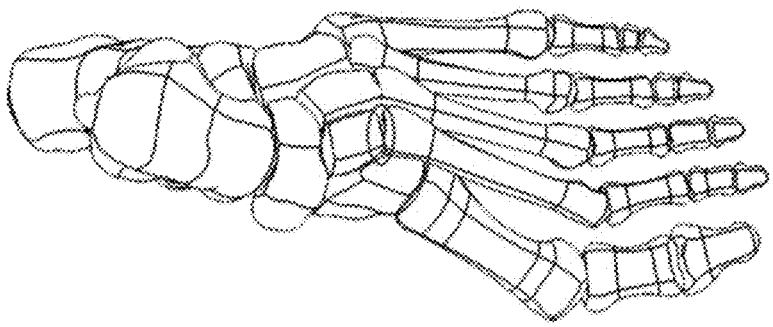
Figure 23C:
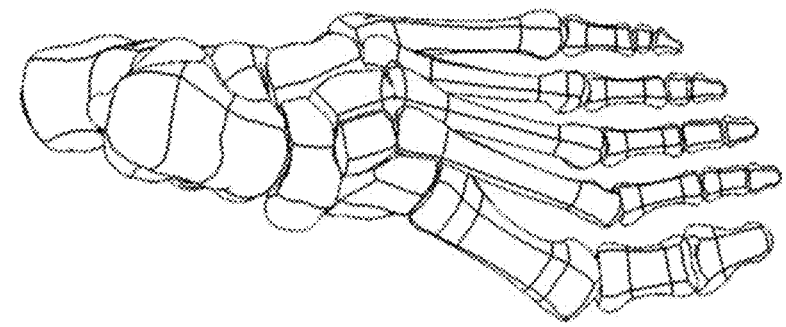
Figure 23D:
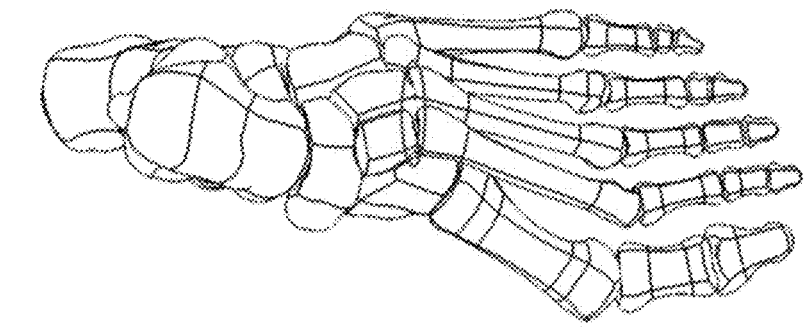
Figure 23E:
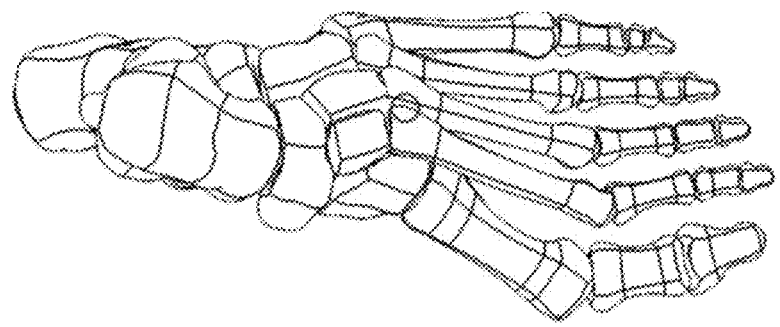
Figures 23F, 23G, 23H, 23I:
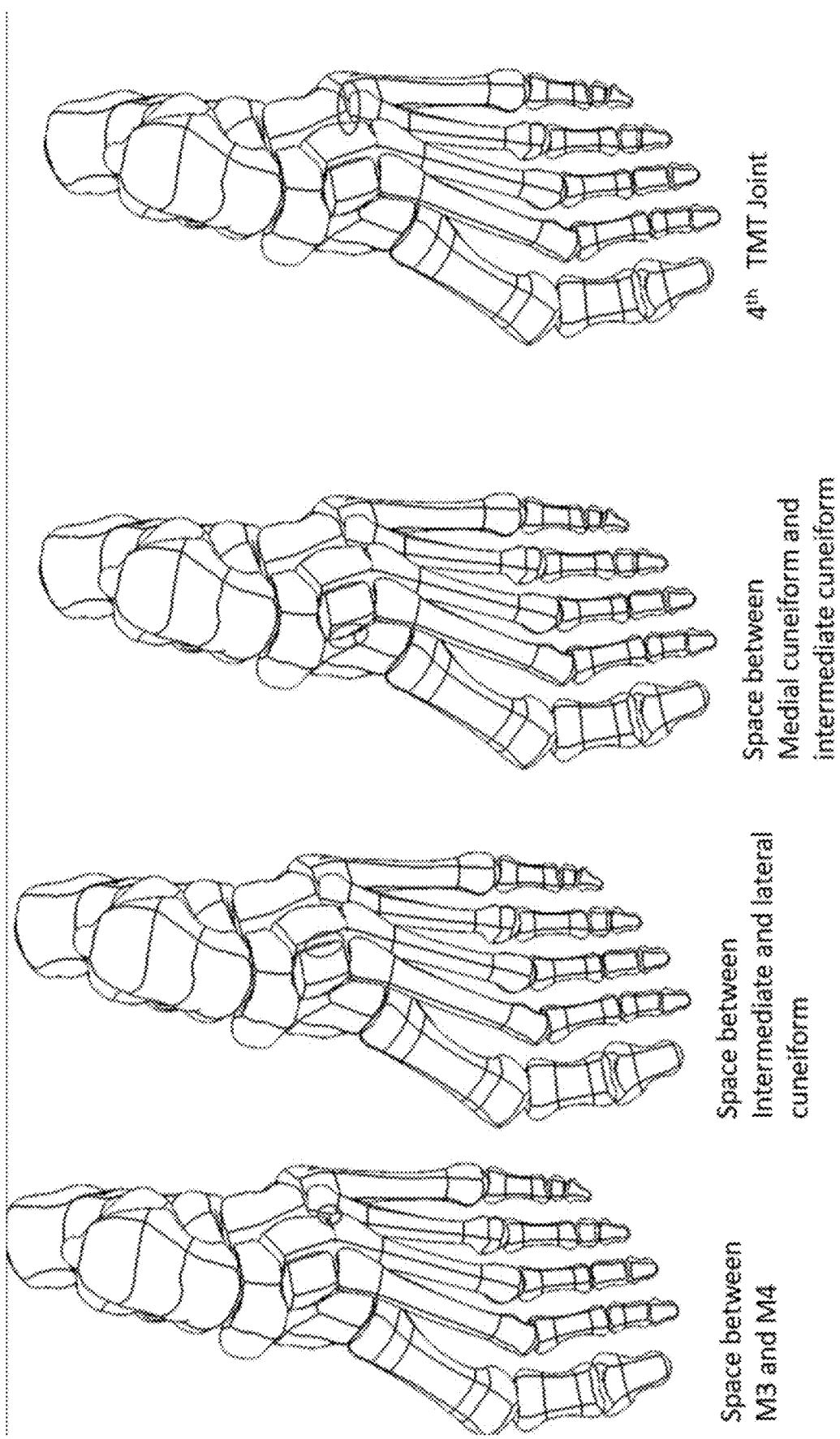

FIG. 23A illustrates a medial corner of the second metatarsal proximal base and intermediate cuneiform as a target location for a locating feature. FIG. 23B illustrates the second TMT joint as a target location for a locating feature. FIG. 23C illustrates the third TMT joint as a target location for a locating feature. FIG. 23D illustrates a combination of the second and third TMT joints as a target location for a locating feature. FIG. 23E illustrates a space between the proximal bases of the second and third metatarsals as a target location for a locating feature. FIG. 23F illustrates a space between the third and fourth metatarsals as a target location for a locating feature. FIG. 23G illustrates a space between the intermediate and lateral cuneiforms as a target location for a locating feature. FIG. 23H illustrates a space between the mediate and intermediate cuneiforms as a target location for a locating feature. FIG. 23I illustrates the fourth TMT joint as a target location for a locating feature.

Figure 17:
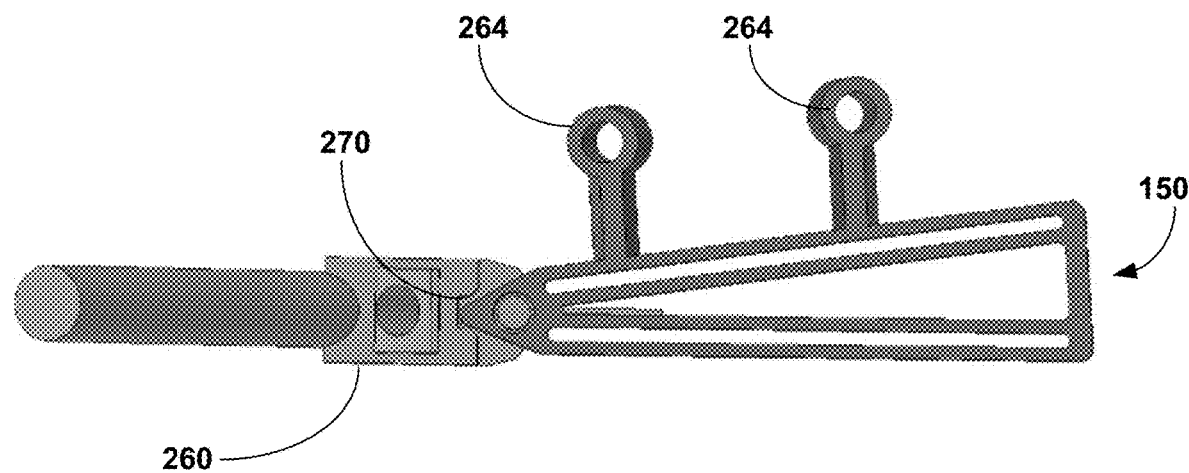
FIGS. 17 and 18 illustrate two different configurations of a cut guide in which the cut guide is restricted to a limited range of rotational movement relative to a spacer or pin insertable into an underlying bone structure.
Figure 18:
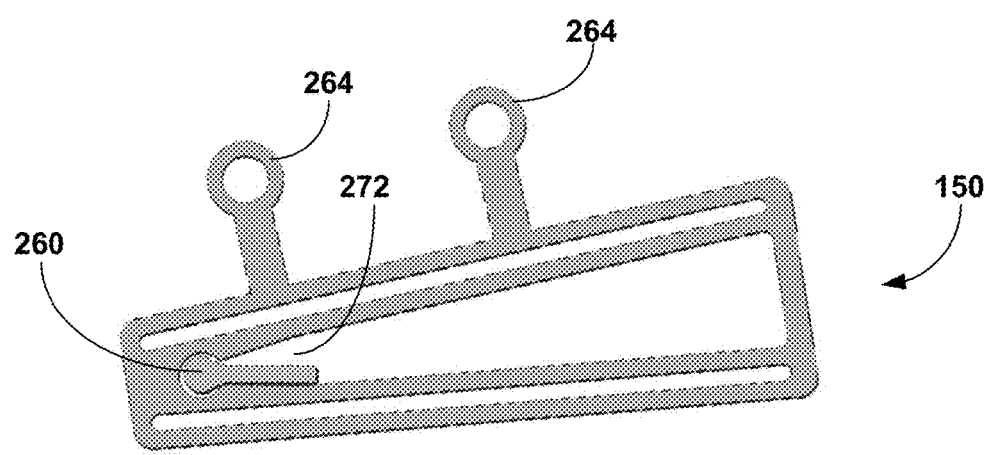

With further reference to FIGS. 15 and 16, in some configurations of cut guide 150, the cut guide may be freely rotatable about a locating feature (e.g., can rotate 360° about the spacer or pin). In other configurations, rotation of the cut guide relative to the spacer or pin may be restricted within a limited angular range of movement, such as a range of 90° or less, 45° or less, or 25° or less. FIGS. 17 and 18 illustrate two different configurations of cut guide 150 in which the cut guide is restricted to a limited range of rotational movement relative to a locating feature insertable into an underlying bone structure.

In the example of FIG. 17, a locating feature 260 is shown defining a slot 270 in which a portion of the body of cut guide 150 is inserted. Cut guide 150 can rotate within a limited range of travel defined by the size of slot 270. In the example of FIG. 18, a locating feature 260 is shown inserted into a slot 272 defined by the body of cut guide 150. Again, cut guide 150 can rotate within a limited range of travel defined by the size of slot 272. In some examples, the limited range of rotation movement is a bounded range less than 90 degrees, such as less than 60 degrees, less than 45 degrees, less than 30 degrees, or less than 15 degrees.

With further reference to FIGS. 13-18, cut guide 150 may include one or more fixation holes 264 that allow the cut guide to be provisionally fixated to an underlying bone. The one or more fixation holes may be configured to receive a fixation pin. In use, the clinician can install cut guide 150 over one or more bones to be cut and/or adjust an orientation of the one or more guide surfaces of the cut guide until such one or more guide surfaces are appropriately positioned relative to the portions of bone to be cut. For example, the clinician may rotate cut guide 150 about a locating feature (e.g., a pin or spacer), such as locating feature 260, until the rotational position of the cut guide appropriately aligns the one or more guide surfaces of the cut guide relative to the bones to be cut. Depending on the configuration of cut guide 150, the clinician may further adjust the relative angle 250 between the guide surfaces. In either case, once cut guide 150 is appropriately positioned relative to the bones to be cut, clinician may insert a pin through each of the one or more fixation holes 264 into an underlying bone. The one or more fixation pins installed through fixation holes 264 can secure and hold cut guide 150 at a desired position for the clinician to subsequently utilize the cut guide to guide movement of a cutting instrument.

In some examples, cut guide 150 includes at least two parallel fixation holes 264, such as two holes positioned to be placed on the dorsal side of two different bones separated by a joint (e.g., a metatarsal and opposed cuneiform). In use, a clinician can insert fixation pins through the two holes to attach the cut guide to the metatarsal and cuneiform, respectively. The clinician may remove the cut guide after use while leaving the parallel pins in position (e.g., by sliding the cut guide up off the parallel pins). The clinician may then insert a second instrument having two parallel fixation holes back down over the parallel fixation pins still remaining in the bones. For example, the clinician may insert a bone positioner and/or compressor back down over the parallel fixation pins. The clinician can then apply a force through the pins using the instrument to move the bones. In addition to or in lieu of providing two parallel fixation holes, cut guide 150 may define one or more fixation holes that are angled (at a non-zero degree angle) or otherwise skewed relative to one or more (e.g., two parallel) fixation holes.

In some configurations, the position of one or more (optionally all) of the fixation holes 264 defined by cut guide 150 are fixedly (e.g., non-movably) located relative to the body of the cut guide. In practice, however, the location of patient's bone surface to a fixation hole 264 defined by a cut guide may vary depending on the anatomy of the patient and extent of the patient's bone deformity. For these and other reasons, cut guide 150 can be configured with one or more adjustable fixation holes 264. A fixation hole may be adjustable in that the fixation hole may be movable relative to a length and/or width of the body of cut guide 150 and/or rotatable to adjust the orientation of the fixation hole relative to the orientation of one or more guide surfaces defined by the cut guide.

Figure 24:
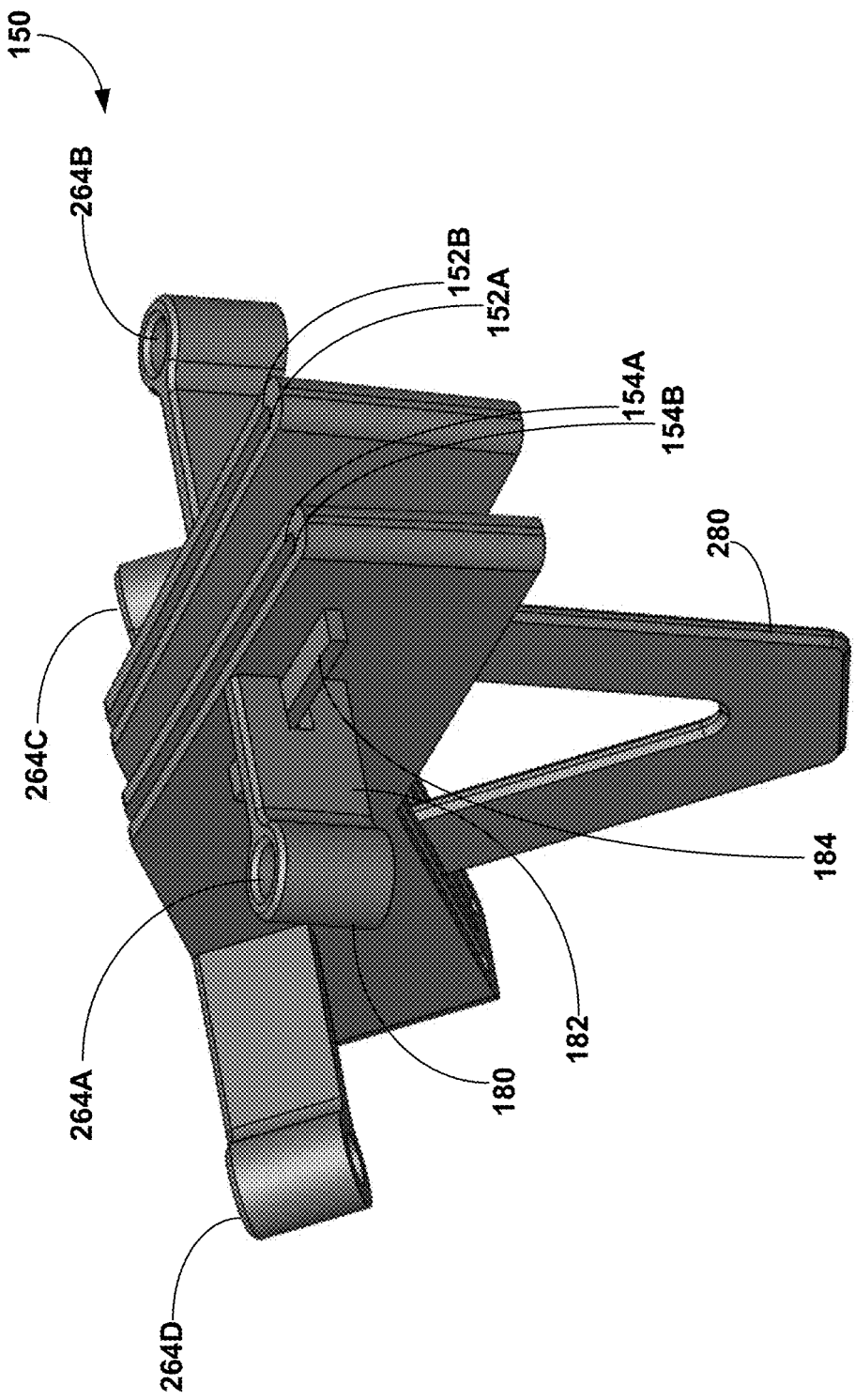
FIG. 24 is a perspective view of an example configuration of a cut guide having at least one adjustable fixation hole.

FIG. 24 is a perspective view of an example configuration of cut guide 150 having at least one adjustable fixation hole 264. Cut guide 150 in FIG. 24 is illustrated as having a plurality of fixation holes 264A-264D, each of which can receive a fixation pin. Cut guide 150 includes at least one adjustable fixation hole 264, which is illustrated as being implemented with two adjustable fixation holes 264A, 264B located on different sides of the cut guide. Cut guide may also include at least one non-adjustable fixation hole, which is illustrated as being implemented with two non-adjustable fixation holes 264C, 264D located on different sides of the cut guide.

Each adjustable fixation hole 264A, 264B on cut guide 150 of FIG. 24 may be defined by a hole body 180 bounding and defining the fixation hole. Hole body 180 may be attached to an arm 182 to position hole body 180 offset from a remainder of the body defining the cut guide (e.g., a portion of the cut guide defining a guide surface). Hole body 180 may be operatively and movably connected to the cut guide body, such as via a rail 184 along which arm 182 can translate. Accordingly, an adjustable fixation hole 264A, 264B can move relative to the length of the body defining the cut guide to reposition the hole at different relative locations along the body.

Figure 25:
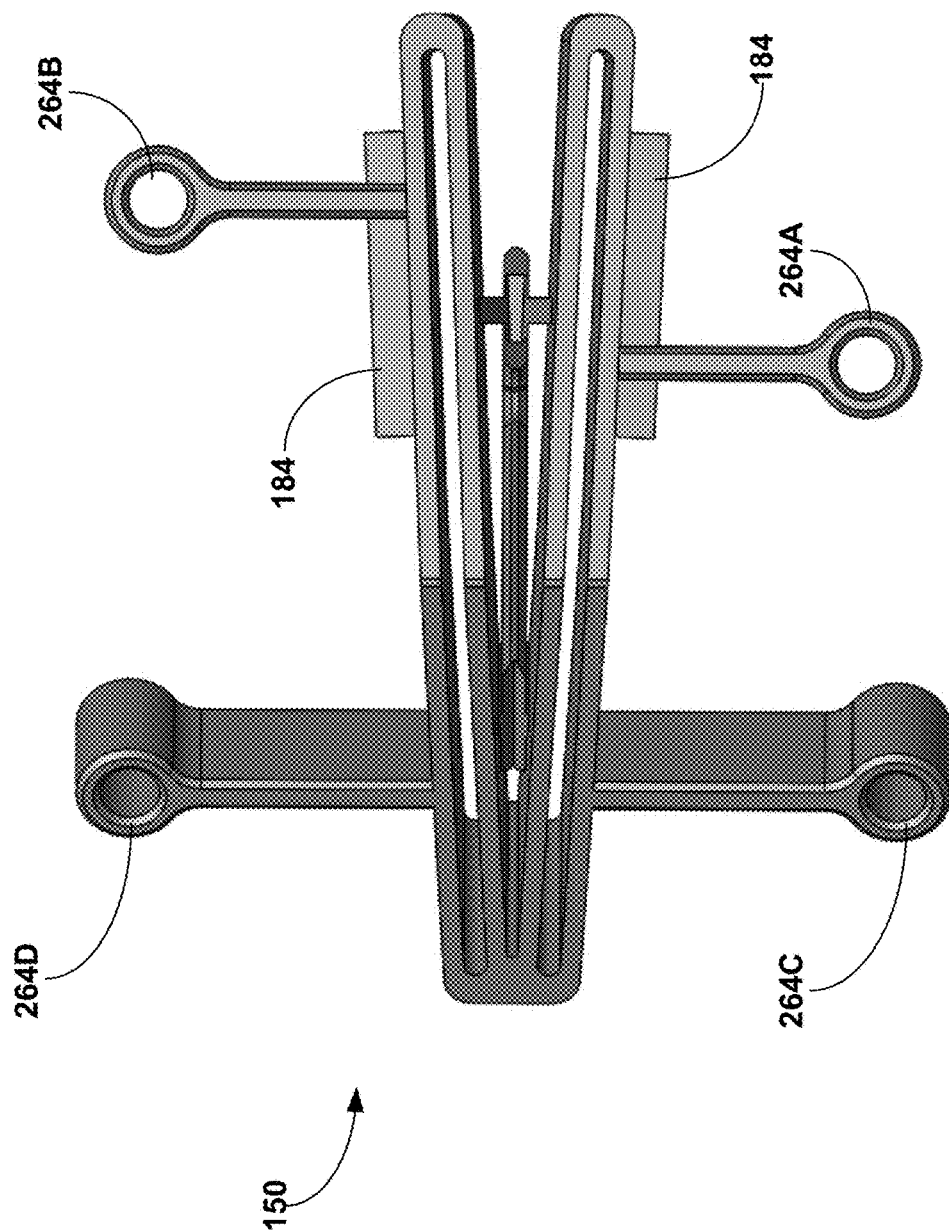
FIG. 25 is a top view of the example cut guide of FIG. 24 showing example positions to which adjustable fixation holes can be moved.

FIG. 25 is a top view of the example cut guide 150 of FIG. 24 showing example positions to which adjustable fixation holes 264A, 264B can be moved. In particular, FIG. 25 illustrates a first adjustable fixation hole 264A positioned at a first location (e.g., medial location) along a range of travel relative to the length of the cut guide and a second fixation hole 264B positioned at a second location (e.g., lateral location) along a range of travel relative to the length of the cut guide. Adjustable fixation holes 264A, 264B can be moved to different locations and/or can have different lengths of adjustability or travel than illustrated without departing from the scope of the disclosure.

As mentioned, configuring cut guide 150 with one or more adjustable fixation holes can be useful to allow the fixation hole to be moved relative to an underlying bone for pinning the cut guide to the bone. When cut guide 150 is positioned over one or more target bones to be prepared, the position of the fixation holes defined by the cut guide relative to underlying bones may vary, e.g., depending on the position of the holes and/or the anatomy of the patient undergoing the procedure. By providing one or more adjustable fixation holes, a fixation hole may be moved to better align with the anatomy of the patient before inserting a pin through the fixation hole.

Figure 26A:
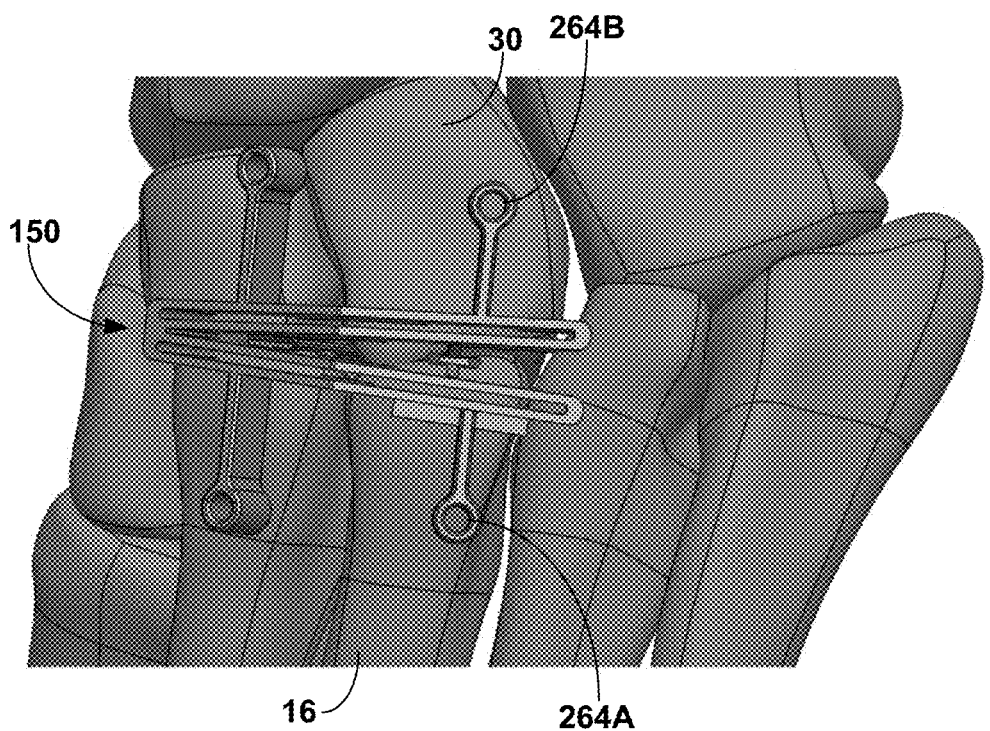
FIGS. 26A and 26B are top images of an example foot showing the cut guide of FIGS. 24 and 25 positioned on the foot.
Figure 26B:
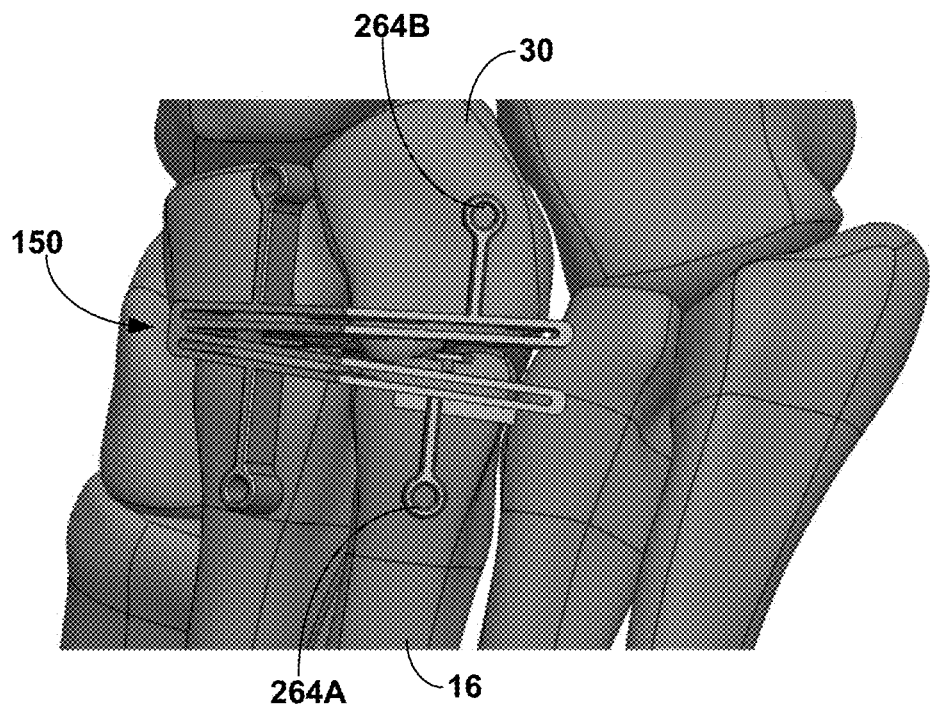

For example, FIGS. 26A and 26B are top images of an example foot showing cut guide 150 of FIGS. 24 and 25 positioned on the foot. FIG. 26A illustrates an example arrangement in which an adjustable fixation hole 264A is offset relative to a midline along the length of an underlying bone (third metatarsal 16 in the example). FIG. 26B illustrates adjustable fixation hole 264A repositioned to be substantially centered on the midline of the underlying bone.

Figure 27A:
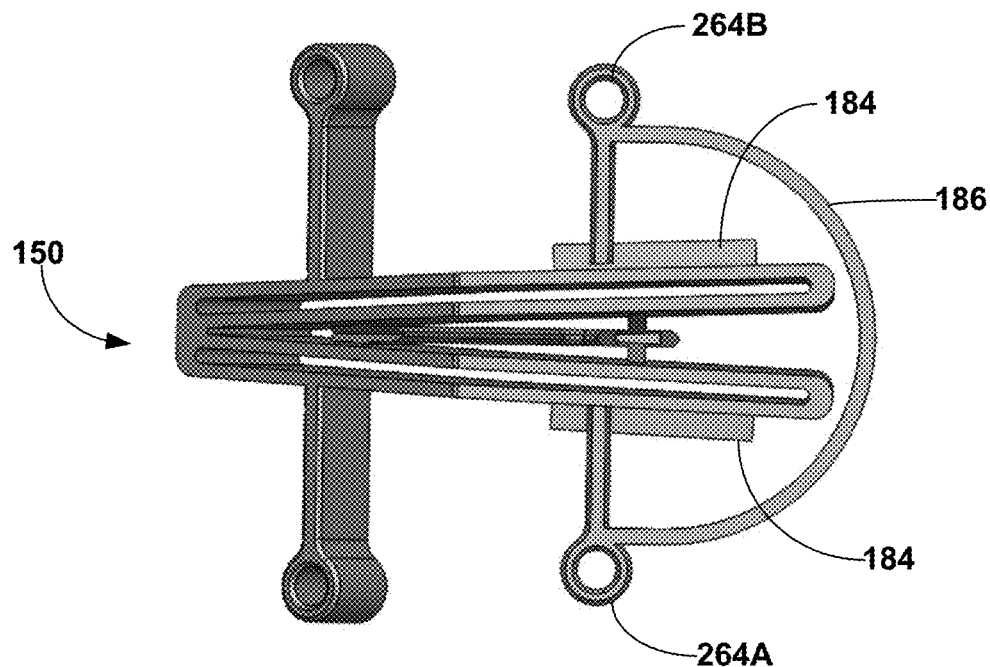
FIGS. 27A and 27B are top view illustrations of an example configuration of a cut guide showing an example linkage between two adjustable fixation holes.
Figure 27B:
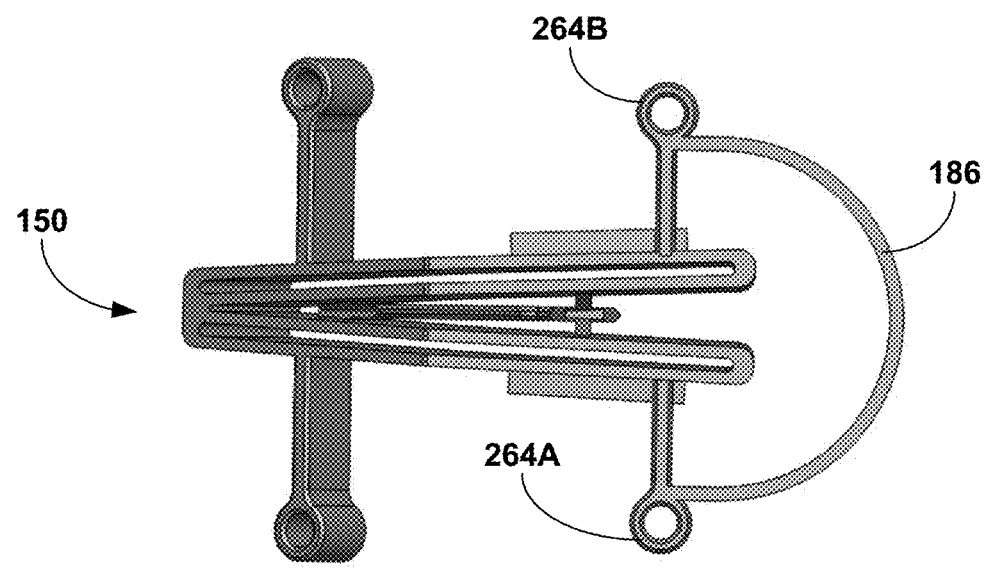

Cut guide 150 may be configured with one or more adjustable fixation holes 264A, 264B. When cut guide 150 include multiple adjustable fixation holes, each of the adjustable fixation holes may move independently of each other. Alternatively, at least two adjustable fixation holes may be operatively connected to each other and configured to move together. For example, FIGS. 27A and 27B are top view illustrations of an example configuration of cut guide 150 showing an example linkage between two adjustable fixation holes 264A, 264B. In the illustrated example, a mechanical linkage in the form of a bridge 186 connects the two adjustable fixation holes 264A, 264B. Bridge 186 may extend outwardly to a side of cut guide 150 (e.g., lateral side) and/or above the cut guide (e.g., dorsally above). In either case, the bridge may mechanically interconnect the two adjustable fixation holes 264A, 264B such that the fixation holes move as a joined pair. Other types of linkages between fixation holes can also be used.

While an adjustable fixation hole associated with cut guide 150 has generally been described and illustrated as being translatable along the length (e.g. parallel to the length) of the cut guide, an adjustable fixation hole may be adjustable in other dimensions relative to the cut guide in addition to or in lieu of being adjustable relative to the length. As one example, the adjustable fixation hole may be adjustable relative to the width of the cut guide (e.g., in the proximal to distal direction when the cut guide is positioned on a foot). For example, arm 182 connecting an adjustable fixation hole to the body of the cut guide may have an adjustable length and/or the adjustable fixation hole may be mounted on a rail or other adjustable feature relative to the width of the cut guide body.

As another example, in addition to or in lieu of being adjustable relative to the length and/or width of the cut guide body, an adjustable fixation hole may be angularly adjustable relative to the cut guide body (e.g., rotatable in the frontal plane). For example, the adjustable fixation hole may be rotatable about an axis of rotation to adjust the angle at which a pin is inserted through the fixation hole into an underlying bone, e.g., independent of the location of the fixation hole relative to the length and/or width of the cut guide body.

Figure 28A:
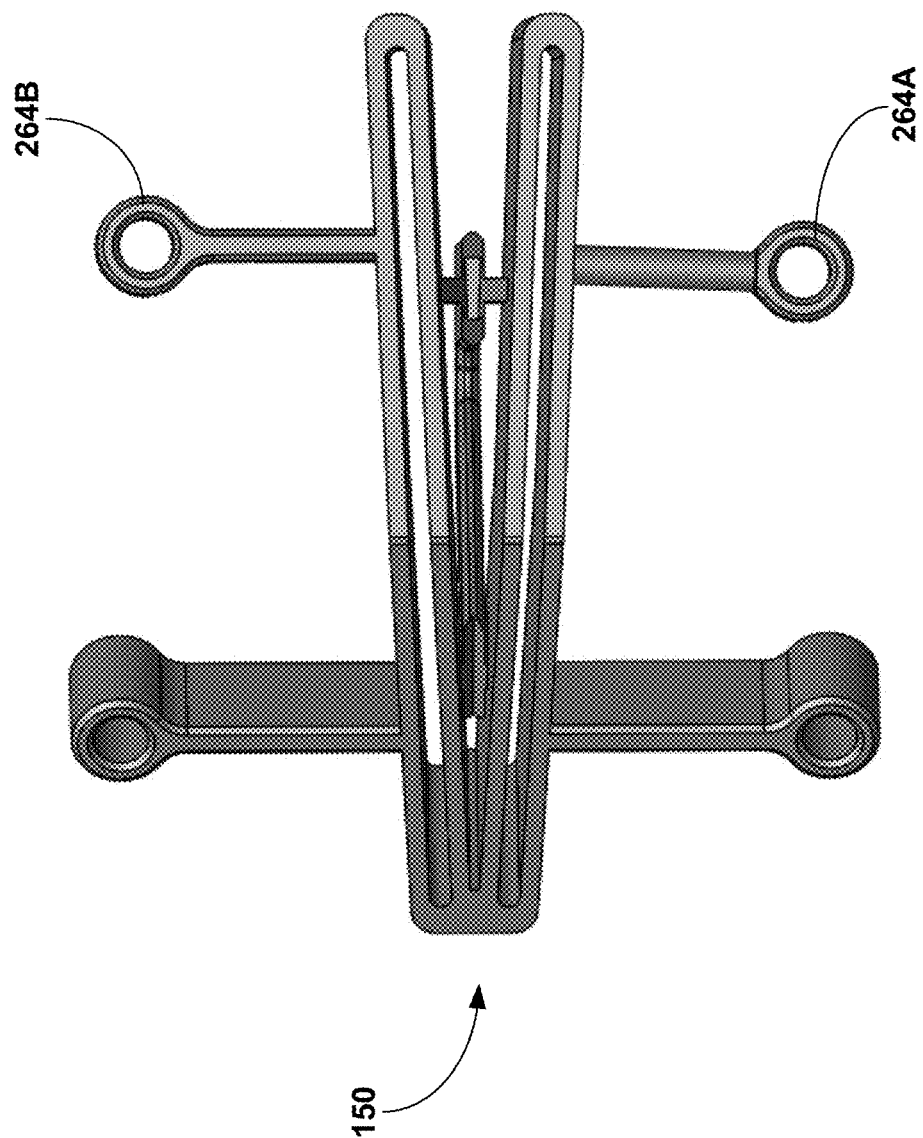
FIGS. 28A and 28B are top view illustrations of an example configuration of a cut guide showing example rotational realignment positions for an adjustable fixation hole.
Figure 28B:
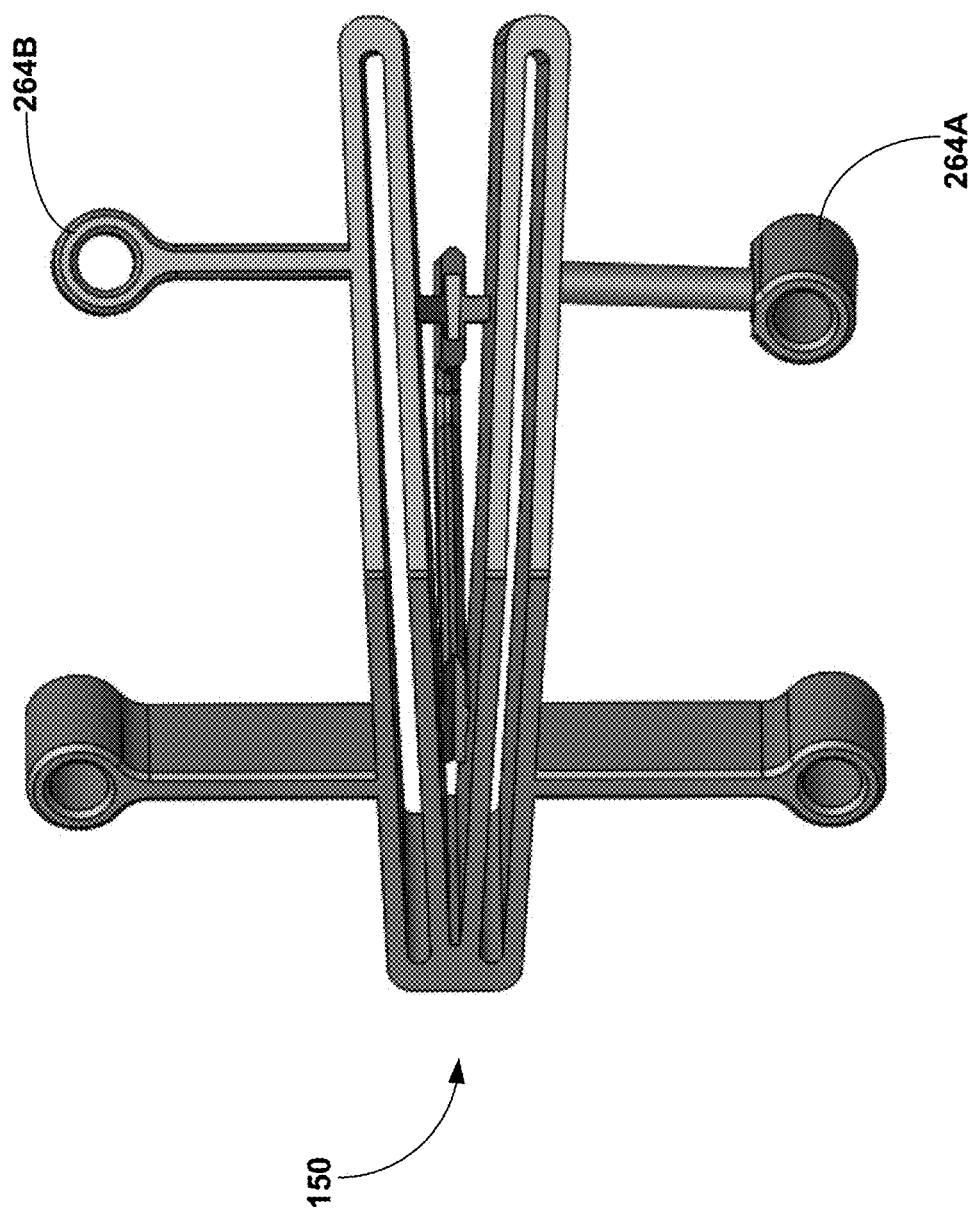

FIGS. 28A and 28B are top view illustrations of an example configuration of cut guide 150 showing example rotational realignment positions for an adjustable fixation hole. In particular, FIG. 28A illustrates adjustable fixation hole 264A angularly orientated to be co-planar with adjustable fixation hole 264B. FIG. 28B illustrates adjustable fixation hole 264A rotationally realigned to position the fixation hole out of plane with adjustable fixation hole 264B. When configured to be rotationally adjustable, the adjustable fixation hole may rotate 360 degrees or may rotate a lesser degree of rotation in a bounded arc, such as over a range of 180 degrees or less, such as 120 degrees or less, 90 degrees or less, or 45 degrees or less.

When using one or more adjustable fixation holes, a set screw, series of detents to which arm 182 can be moved, and/or other engagement/locking feature may be used to hold a position to which an adjustable fixation hole is moved. Accordingly, in use, a clinician may position cut guide 150 over one or more bone portions to be cut using one or more guide surfaces defined by the cut guide. The clinician may then adjust a position of one or more adjustable fixation holes of the cut guide (e.g., in one or more dimensions) relative to underlying bones. The clinician may adjust the position of an adjustable fixation hole so a pin subsequently inserted therethrough is substantially centered about a medial line of the underlying bone. Once adjusted to a desired position, the clinician may lock the adjusted position of the fixation hole and then insert a fixation pin through the adjusted fixation hole into an underlying bone.

Figure 19:
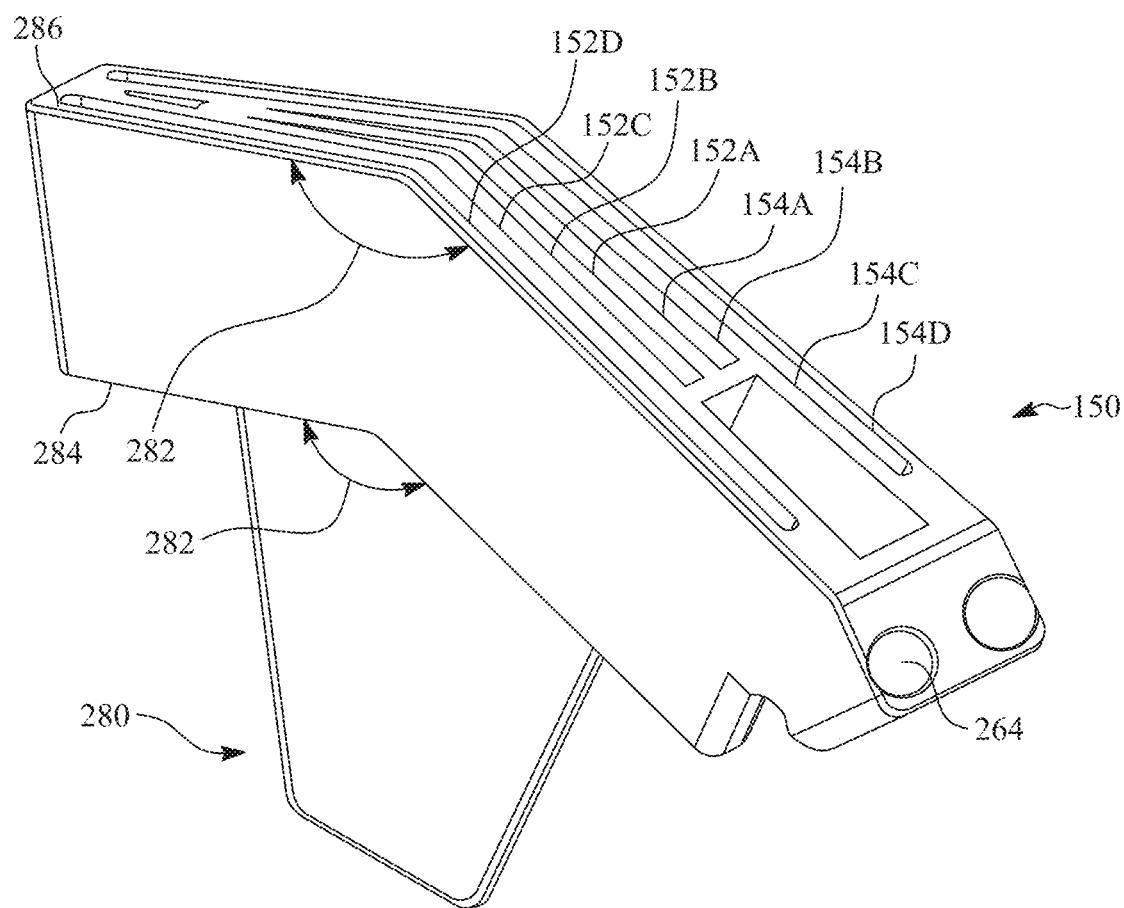
FIG. 19 is perspective view of an example cut guide with associated locating feature.

Cut guide 150 can have a variety of different configurations, as discussed above. For example, cut guide 150 can have one or more associated locating features (e.g., pins and/or spacers), each of which can be permanently affixed to or separable from the body of the cut guide. The pin(s) and/or spacer(s) can function as a locating feature insertable into a bone and/or a joint space between adjacent bones, respectively, to provide anatomical reference locations for orienting cut guide 150 relative to the anatomy of the foot of the patient undergoing the clinical procedure. FIG. 19 is perspective view of another example implementation of cut guide 150 with associated locating feature 280, which is illustrated as a spacer in the form of a keel. Spacer 280 can be permanently affixed to, or detachably couplable to, cut guide 150. Spacer 280 can be configured (e.g., sized and/or shaped) to be positioned in one or more joint spaces, such as bridging across multiple joint spaces of one or more bones to be cut.

As discussed above, cut guide 150 can include one or more guide surfaces configured to extend across multiple bones to be cut, such as across second metatarsal 14 and third metatarsal 16 and/or across intermediate cuneiform 28 and lateral cuneiform 30. Accordingly, spacer 280 may be configured to be positionable at least partially within multiple joint spaces, such as at least partially within the second tarsometatarsal joint space (between second metatarsal 14 and intermediate cuneiform 28) and also at least partially within the third tarsometatarsal joint space (between third metatarsal 16 and lateral cuneiform 30). Spacer 280 can bridge across the intermetatarsal space between second metatarsal 14 and third metatarsal 16. Configuring spacer 280 to be simultaneously positionable in two tarsometatarsal joint spaces can be useful to properly align cut guide 150 relative to bones to be cut on either side of both joint spaces.

Figure 20:
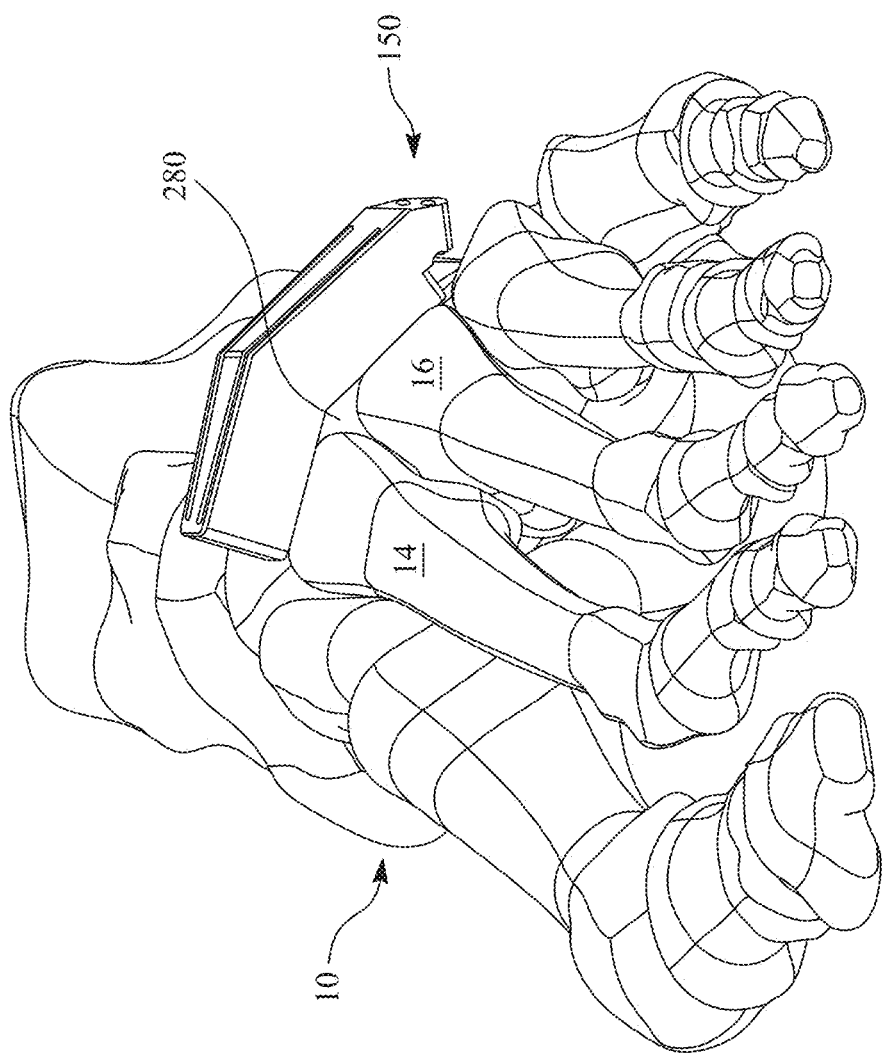
FIG. 20 is a front perspective view of a foot showing the cut guide of FIG. 19 positioned over a dorsal side of one or more bones to be cut.

FIG. 20 is a front perspective view of foot 10 showing cut guide 150 positioned over a dorsal side of one or more bones to be cut with spacer 280 inserted (plantarly) into two tarsometatarsal joint spaces. In particular, in the illustrated example, spacer 280 is positioned at least partially within the second tarsometatarsal joint space and the third tarsometatarsal joint space, with the spacer bridging across the intermetatarsal space between second metatarsal 14 and third metatarsal 16. In some examples, spacer 280 is configured to contact at least a medial quarter of the end face of second metatarsal 14 and the opposed end face of intermediate cuneiform 28, such as at least a medial half, or the full end face of the second metatarsal and the intermediate cuneiform. Additionally or alternatively, spacer 280 can be configured to contact at least a lateral quarter of the end face of third metatarsal 16 and the opposed end face of lateral cuneiform 30, such as at least a lateral half, or the full end face of the third metatarsal and the lateral cuneiform. Spacer 280 can bridge across the intermetatarsal space between the two tarsometatarsal joint spaces.

In practice, certain patients may exhibit significant step off, or distal offset, between adjacent joint planes (e.g., between the plane defining the second TMT joint and the plane defining the third TMT joint). As a result, the patient may exhibit a protruding bone portion across the combined joint space that spacer 280 is targeted to be inserted into. This can make it challenging for the clinician to insert spacer 280 across the adjacent joint spaces.

Figure 29:
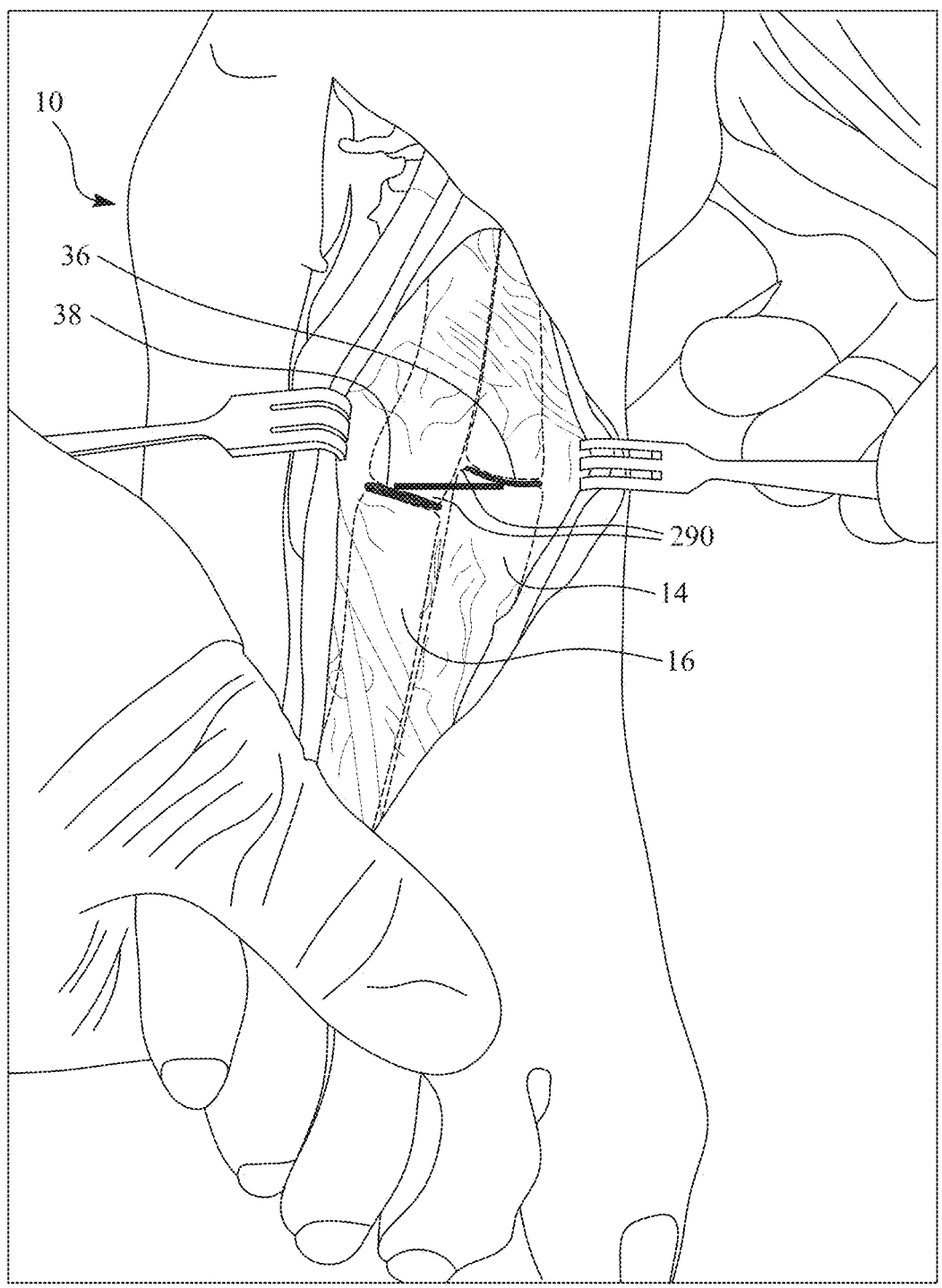
FIG. 29 is an image of an example patient's foot showing a distal offset between a second TMT joint and a third TMT joint.

For example, FIG. 29 is an image of an example patient's foot 10 showing a distal offset between the second TMT joint 36 and third TMT joint 38. In this example, protruding bone portions 290 project at least partially across the region between second TMT joint 36 and third TMT joint 38 where spacer 280 is targeted for insertion. In particular, the illustrated example shows a proximal protruding bone tip 290 on a lateral side of second metatarsal 14 and a distal protruding bone tip 290 on a medial side of third metatarsal 16. To facilitate insertion of spacer 280, the clinician may remove the one or more protruding bone portions 290, e.g., to create a pocket or continuous joint line extending across the second TMT joint and the third TMT joint for receiving spacer 280.

Figure 30:
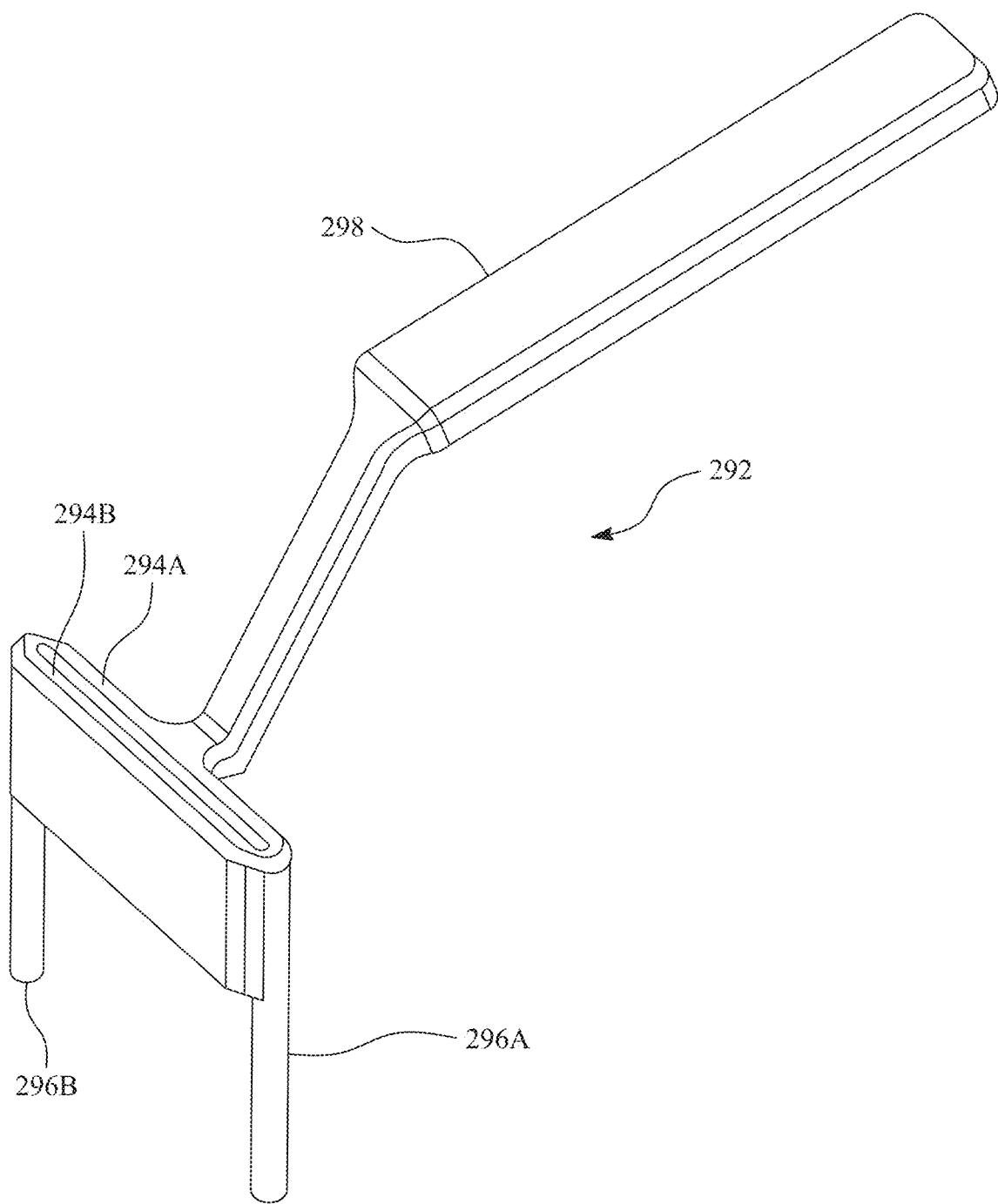
FIG. 30 is a perspective illustration of an example cutting guide that can be used to remove a protruding bone portion.
Figure 31:
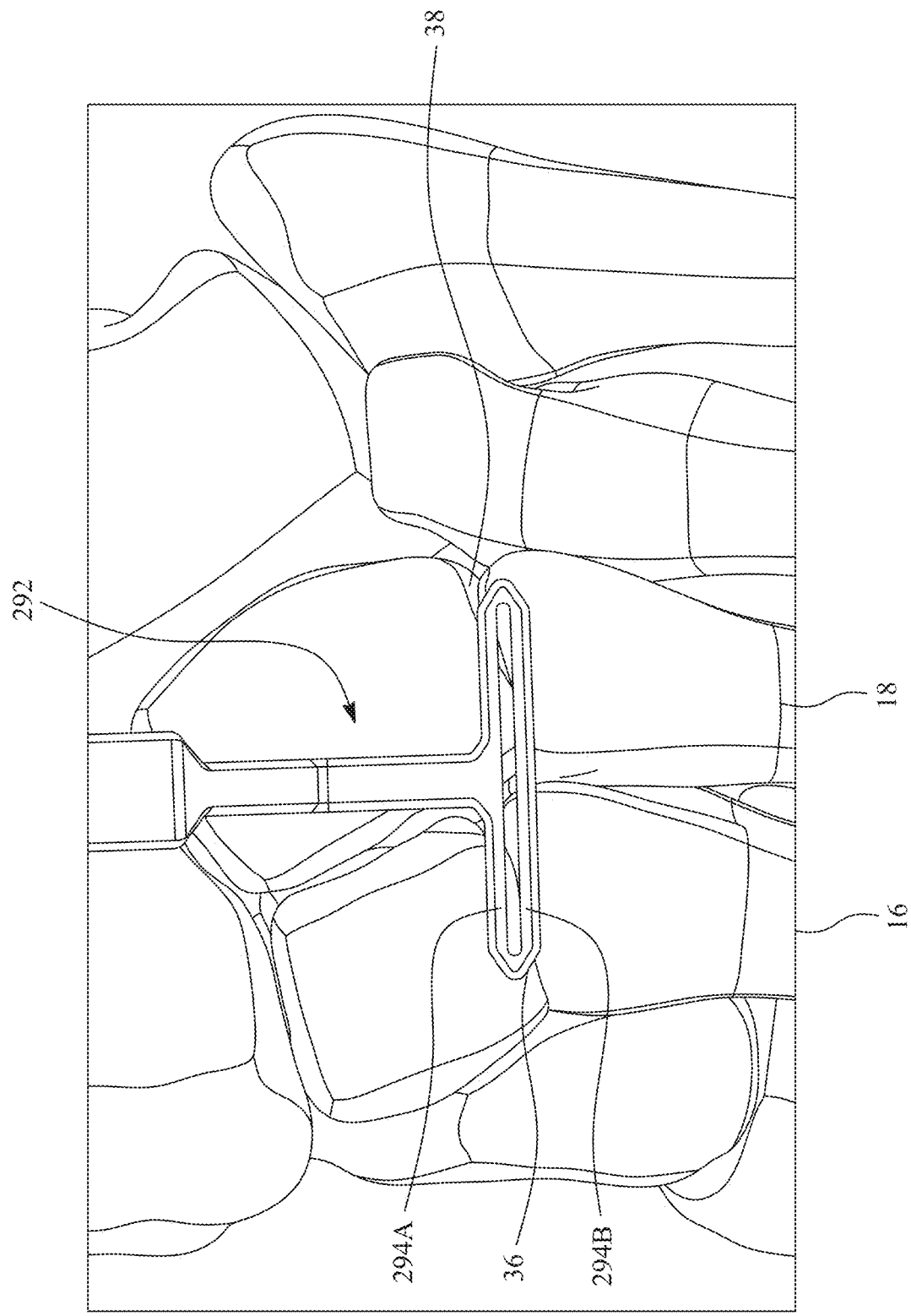
FIG. 31 is top view of a foot showing an example positioning of the cutting guide of FIG. 30.

In some examples, the clinician removes the one or more protruding bone portions 290 freehand (e.g., without the aid of a cutting guide). In other examples, however, the clinician may utilize a cut guide to help remove the one or more protruding bone portions. FIG. 30 is perspective illustration of an example cut guide 292 that can be used as a planing guide to remove a protruding bone portion. FIG. 31 is top view of a foot showing an example positioning of the cutting guide of FIG. 30. As shown in this example, cut guide 292 may define at least one guide surface 294A along which a cutting instrument can be guided. For example, the cut guide may define a pair of guide surfaces 294A, 294B defining a cutting slot therebetween through which a cutting instrument can be inserted.

The at least one guide surface 294A of cut guide 292 can be configured to extend at least partially across one or more bones and/or joint spaces for removing protruding bone. For example, the cut guide may be sized to extend from a medial side of one or more bones (e.g., second metatarsal 14) to a lateral side of one or more bones (e.g., third metatarsal 16). For example, the at least one guide surface 294A may be sized relative to the size of a corresponding locating feature 280 of cut guide 150 to be installed after opening the joint space using the preliminary cut guide 292. The at least one guide surface 294A may have a length (in the medial to lateral direction) at least as long as a width of spacer 280 (in the medial to lateral direction).

In use, the clinician can position cut guide 292 to span at least partially across a pair of adjacent joint spaces (e.g., second TMT joint space 36 and third TMT joint space 38). For example, the clinician can position cut guide 292 on a dorsal side of the foot substantially centered between the two joint spaces (e.g., substantially centered at the intersection between the proximal bases of second metatarsal 14 and third metatarsal 16). The clinician can then guide a cutting instrument along the at least one guide surface 294A to remove protruding bone portion(s). This can create an opening or pocket into which spacer 280 can then be inserted.

To help position cut guide 292 spanning over one or more joint spaces, the cut guide may include one or more locating features. For example, cut guide 292 may include a first locating feature 296A on a medial side of the cut guide and a second locating feature 296B on a lateral side of the cut guide. The two locating features may have a comparatively small cross-sectional area and be separated by a gap. As a result, first locating feature 296A can be positioned on a medial side of second TMT joint space 36 and second locating feature 296B can be positioned on a lateral side of third TMT joint space 38, with the gap spanning any protruding bone portions to be excised using the cut guide.

While cut guide 292 may be useful to open a receiving cavity between adjacent joint spaces for subsequently inserting a locating feature, the cut guide can be used for other purposes as well. For example, cut guide 292 may be used as an axillary instrument to remove a portion of a bone end, e.g., as part of a revision procedure or trimming on a bone end after removing an initial portion of bone using cut guide 150. As another example, the clinician may use cut guide 292 to prepare a joint for fusion, e.g., by making a substantially planer cut on the end faces of both bones facing the joint space to promote fusion. This can be useful, for example, to prepare an arthritic joint for fusion, which may be done with or without realignment of a bone defining the joint before or after preparing the bone end.

In addition, cut guide 292 is illustrated as having an optional handle 298 extending upwardly and outwardly away from the at least one guide surface of the cut guide. Any cut guide described herein may or may not have a handle, such as handle 298, to aid clinician manipulation of the cut guide. When used, the handle can be permanently and integrally connected to the remainder of the cut guide or may be detachably connected to the remainder of the cut guide (e.g., to the allow the handle to be removed after positioning the remainder of the cut guide at a desired location). If desired, the clinician may grasp the handle to hold the cut guide in position (e.g., with or without pinning the cut guide to underlying bones) while making one or more cuts.

With further reference to FIG. 19, cut guide 150 includes at least one guide surface positionable over a dorsal side of a bone to be cut. In the illustrated example of FIG. 19, cut guide 150 includes a first metatarsal-side guide surface 152A and a second metatarsal-side guide surface 152B parallel to the first guide surface to define a cutting slot between the two guide surfaces. The cut guide also includes a third metatarsal-side guide surface 152C and a fourth metatarsal-side guide surface 152D parallel to the third guide surface to define a second cutting slot between the two guide surfaces. The second cutting slot is positioned distally of the first cutting slot.

In addition, cut guide 150 in FIG. 19 includes a first cuneiform-side guide surface 154A and a second cuneiform-side guide surface 154B parallel to the first guide surface to define a cutting slot between the two guide surfaces. The cut guide also includes a third cuneiform-side guide surface 154C and a fourth cuneiform-side guide surface 154D parallel to the third guide surface to define a second cutting slot between the two guide surfaces. The second cuneiform-side cutting slot is positioned proximally of the first cuneiform-side cutting slot. Cut guide 150 can have a different number or arrangement of guide surfaces, as discussed above.

Configuring cut guide 150 with multiple guide surfaces (e.g., cutting slots) offset (e.g., proximally or distally) from each other can be useful to provide the clinician with flexibility in selecting the amount of bone to remove. The clinician can select one of multiple parallel guide surfaces (e.g., two, three, four, or more guide surfaces) based on the desired amount of bone to be removed and guide a cutting instrument along the selected guide surface to remove the desired amount of bone. Configuring cut guide 150 with multiple guide surface can also be useful to allow revision cuts. For example, after the clinician removes an initial amount of bone using one guide surface, the clinician may decide that additional bone removal is appropriate to achieve the desired correction. Accordingly, the clinician may reuse the same cut guide, selecting a different guide surface farther along the length of the bone to remove an additional portion of bone. Any configuration of cut guide 150 described herein can include multiple guide surfaces (e.g., cutting slots) spaced from each other (e.g., proximally and/or distally), which may or may not be parallel aligned to each other, to facilitate removing different amounts of bone depending on the specific guide surface selected by the clinician.

With reference to FIG. 19, cut guide 150 may be configured with a continuous guide surface configured to extend across two bones to be cut (e.g., from a medial-most side of the second metatarsal 14 to a lateral-most side of third metatarsal 16) or may have a discontinuous guide surface with separate portions configured to be positioned over separate bones to be cut. In either case, cut guide 150 may define a non-zero degree angle 282 between the portion of one or more guide surfaces configured to be positioned over a medial bone to be cut (e.g., second metatarsal 14, intermediate cuneiform 28) and the portion of one or more guide surfaces configured to be positioned over a lateral bone to be cut (e.g., third metatarsal 16, lateral cuneiform 30). Angling the medial and lateral portions of cut guide 150 relative to each other may be useful to orient the guide surface(s) defined by the guide relative to the anatomical contour of the foot, e.g., as illustrated in FIG. 20. In some examples, cut guide 150 defines an angle 282 between a guide surface to be positioned over a medial bone and a guide surface to be positioned over an adjacent lateral bone ranging from 90 to 179 degrees, such as from 110 to 175 degrees, from 125 to 170 degrees, or from 135 to 165 degrees.

When cut guide 150 is configured with an angled shape between medial and lateral portions of the cut guide, both the plantar side of the cut guide (e.g., bone contacting surface of the cut guide) and the dorsal side of the cut guide (e.g., outward facing side of the cut guide) may be angled. For example, FIG. 19 illustrates both the bone contacting side 284 of cut guide 150 and the outward facing side 286 of the cut guide being angled at substantially the same angle 282. This arrangement may be useful so the bone contacting side 284 of cut guide 150 conforms to the profile of the underlying bones and this profile is observable to the clinician through the mirrored profile on the outward facing side 286 of the cut guide. In other examples, however, one or both sides 284, 286 of the cut guide may be straight (e.g., non-angled) or the bone contacting side 284 may be angled at a different degree of angulation than the outward facing side 286 of the cut guide.

While cut guide 150 may define a sharp transition between the different planes defining the bone facing surfaces and/or outward facing surfaces of the cut guide, in other examples, the cut guide may define a curved bone facing surface and/or outward facing surface to effect the transition between the different planes defined by the bones. For example, the bone facing surface 284 of cut guide 150 may define a curved profile that positions the bone facing surface in contact with the dorsal surfaces of the underlying bones. The outward facing surface 286 may or may not mirror the curved bone facing surface.

In practice, angling and/or curving the outward facing surface 286 of cut guide 150 can be useful so the lateral portion of the cut guide is offset plantarly relative to the medial portion of the cut guide. This may help the clinician visualize the sagittal plane offset between the second and third metatarsals. For example, the clinician may be instructed to move the cutting instrument perpendicular to the outward facing surface of cutting guide 150, resulting in an angular reorientation of the cutting instrument as the instrument moves to the angled lateral portion of the cutting guide. This can help prevent the clinician from inadvertently cutting into the adjacent fourth metatarsal.

Figure 32:
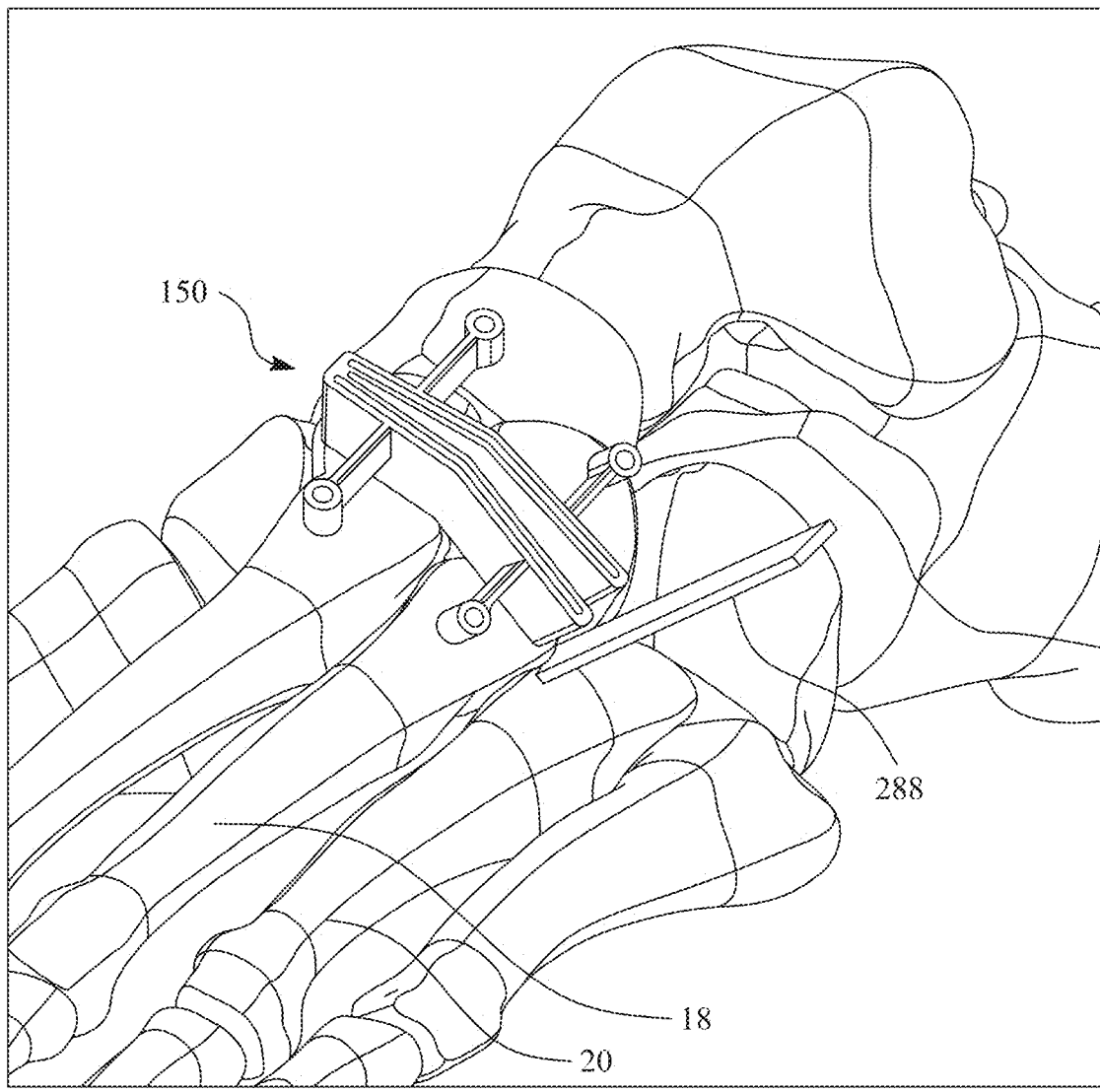
FIG. 32 is a perspective illustration of a foot showing an example cut guide and blocking element, where the blocking element is positioned to limit movement of a cutting instrument to help prevent inadvertent cutting of an adjacent metatarsal.

To help guide the clinician's cutting motion and/or to help prevent inadvertent cutting of an adjacent metatarsal, a blocking or fencing element may be positioned on a side (e.g., lateral side) of the cut guide. FIG. 32 is a perspective illustration of a foot showing an example cut guide 150 and blocking element 288, where the blocking element is positioned to limit movement of a cutting instrument to help prevent inadvertent cutting of an adjacent metatarsal. The blocking element may be a pin, osteotome, or other feature. Blocking element 288 can be connected to cut guide 150 or may be a separate feature from the cut guide. Blocking element 288 may define a length extending above the uppermost surface of cut guide 150. For example, blocking element 288 may extend to a height above the dorsal surface of a metatarsal that is at least twice the height to which the upper surface of cut guide 150 extends. In the illustrated example, blocking element is inserted between third metatarsal 16 and fourth metatarsal 18. In either case, blocking element 288 may function as a visual and/or tactile barrier to limit the lateral motion of a cutting instrument by a clinician.

Figure 21:
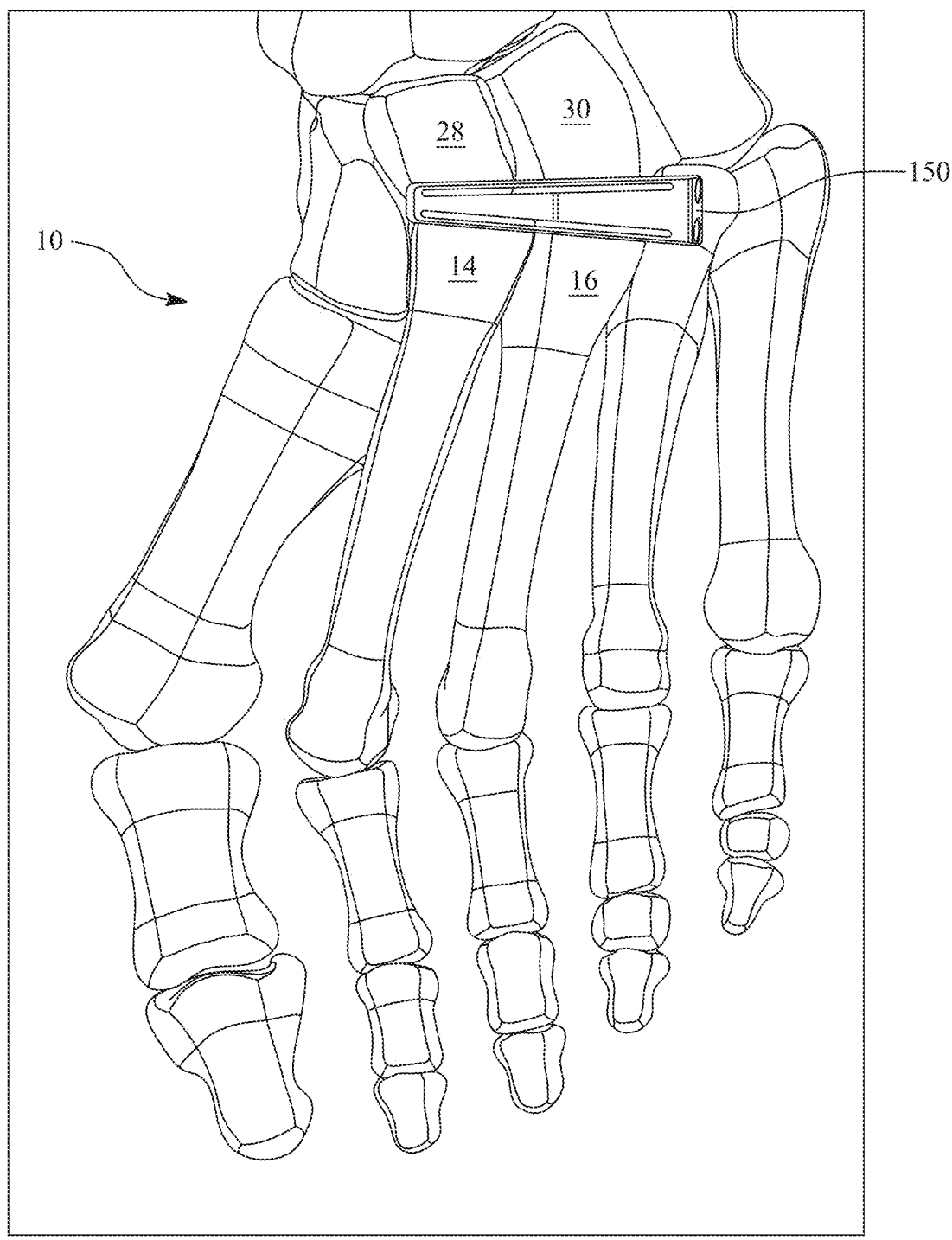
FIG. 21 is a top view of the foot with engaged cut guide of FIG. 20.

In use, spacer 280 can be positioned at least partially within two different and adjacent joint spaces, where each joint space separates two opposed bone ends. This can orient the one or more guide surfaces of cutting guide 150 over the dorsal surfaces of adjacent bone ends to be cut. FIG. 21 is a top view of foot 10 illustrating an example configuration of cutting guide 150 positioned over adjacent bone ends to be cut, with spacer 280 inserted into adjacent joint spaces defined by the bone ends to be cut. Cutting guide 150 in FIG. 21 is illustrated as having a single cuneiform-side cutting slot and a single metatarsal-side cutting slot, although can have different designs as discussed above.

In general, spacer 280 may extend from a first end attached to, or attachable to, cut guide 150 to a second end insertable plantarly into adjacent joint spaces. In some examples, such as the example of FIG. 19, spacer 280 may taper in width (e.g., the distance the spacer spans across the adjacent joint spaces) and/or thickness from the first end to the second end. In other examples, spacer 280 may have a constant width and/or thickness over the length of the spacer.

In FIG. 19, spacer 280 is illustrated as a block insertable into adjacent tarsometatarsal joint spaces, with the spacer block spanning between the two tarsometatarsal joint spaces. In other examples, cut guide 150 may be attached to, or attachable to, two spacers separately positionable in adjacent joint spaces, with a gap or void space between the two spacers. For example, FIG. 22 is a perspective view of another configuration of cut guide 150 showing the cut guide associated with two spacers 280A, 280B. Spacer 280A may be positioned in a first tarsometatarsal joint space (e.g., between second metatarsal 14 and intermediate cuneiform 28), and spacer 280B may be positioned in a second first tarsometatarsal joint space (e.g., between third metatarsal 16 and lateral cuneiform 30).

While the foregoing description of cut guide 150 and associated locating feature(s) has generally focused on a configuration for positioning over the second tarsometatarsal joint and the third tarsometatarsal joint, the cut guide can be configured to cut any tarsometatarsal joint or combination of joints. For example, cut guide 150 and associated locating feature(s) (when used) can be configured for positioning one or more guide surfaces over one or more bone ends defining the third tarsometatarsal joint and fourth tarsometatarsal joint, or the fourth tarsometatarsal joint and fifth tarsometatarsal joint, instead of the second and third tarsometatarsal joints. Accordingly, discussion of instruments and techniques for preparing an end of second metatarsal 14 and/or and end of intermediate cuneiform 28 (and/or an end of third metatarsal 16 and/or an end of lateral cuneiform 30) should be understood to apply equally to other lesser tarsometatarsal joint spaces and/or other bone ends.

Further, reference to a metatarsal-side and cuneiform-side for any device herein (e.g., bone positioner, cut guide) is intended to describe relative positions and orientations of features where the device crosses a TMT joint with a metatarsal on one side and a cuneiform on another side. Where the device is deployed across two different bones, such as the fourth metatarsal and the cuboid bone or yet other two bones or bone portions (e.g., two bone portions separated by a joint), the terminology can be changed based on that anatomy.

While the foregoing description of techniques and instruments has included discussion of example cut guides, it should be appreciated that a portion or all of one or more techniques can be performed without the use of a cut guide. For example, a technique according to disclosure may be performed freehand (without the use of a cutting guide) or with the aid of a bone preparation template in addition to or in lieu of using a cut guide. In general, a bone preparation template may be a device that is configured (e.g., sized and/or shaped) to overlay one or more bone portions to be subsequently cut. The bone preparation template may be configured to indicate where on the underlying bone the bone should be cut or otherwise prepared. Positioning the bone preparation template on the underlying bone may mark or otherwise indicate on the bone where the bone should be prepared and/or the clinician may use the bone preparation template to mark where on the bone the bone should be prepared. The clinician may subsequently remove the bone preparation template and preform a bone preparation step (e.g., cutting) at the location marked or otherwise indicated using the template.

As one example, the bone preparation template may have a sharpened surface, such as a sharpened surface projecting plantarly on a bone-contacting side of the bone preparation template. The sharpened surface can be implemented as chisel, scoring line, or other feature that imparts an indicating mark or marks on a surface (e.g., bone surface) that is contacted by the feature. The clinician can position the template relative to one or more bones to be prepared, for example, using one or more locating features and/or other orienting features, to position the template relative to one or more target anatomical locations of the patient. As the template contacts one or more bone surfaces (e.g., by the clinician pressing the template downwardly against the bone surface and/or sliding the template back and forth relative to the bone), the sharpened surface may impart an indicating mark on the bone. Additionally or alternatively, the clinician may apply energy (e.g., radio-frequency current, laser energy) through and/or adjacent to the template to burn, score, and/or otherwise generate an indicating mark on one or more bones. The clinician can subsequently perform freehand bone preparation (e.g., cutting) using a tissue removing instrument that follows or traces the indicating mark.

As another example, a bone preparation template may include a light source (e.g., built-in laser light or other light targeting device) that displays a light template on and/or over one or more bones. The light source may be positioned relative to one or more bones to be prepared, for example, using one or more locating features and/or other orienting features to position the light source relative to one or more target anatomical locations of the patient. The light source can be activated to display one or more light lines or other indicating light marks on and/or over one or more bones to be prepared. The clinician can perform freehand bone preparation (e.g., cutting) using a tissue removing instrument that follows or traces the marks or lines broadcast by the light source.

Figure 33:
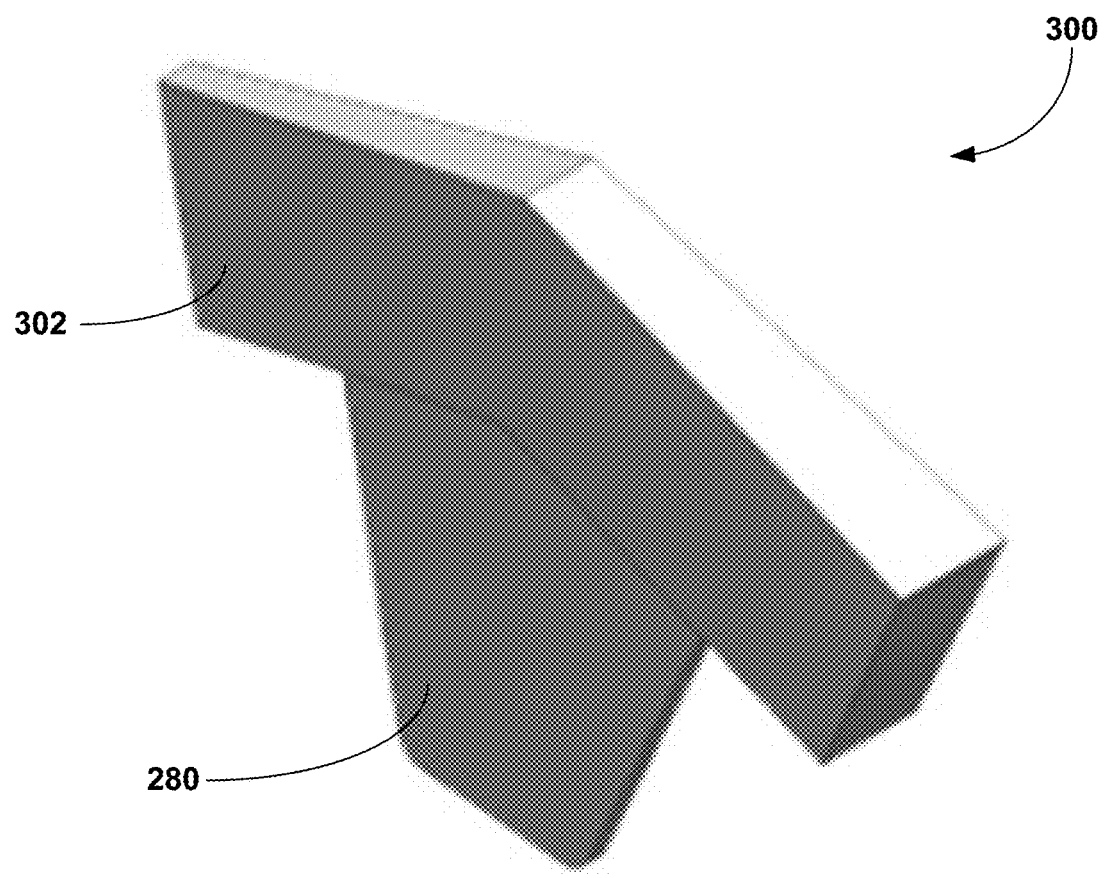
FIG. 33 is a perspective view of an example bone preparation template that defines one or more guiding surfaces that can be used to guide a marking instrument.

As another example, the bone preparation template may be a shaped structure (e.g., fabricated of metal or plastic) that has one or more guide surfaces (e.g., optionally without slots) that can be used to guide a marking source. The guide surface to guide a marking instrument can be positioned relative to one or more bones to be prepared, for example, using one or more locating features and/or other orienting features to position the surface relative to one or more target anatomical locations of the patient. The clinician can then use the template to guide a marking source (e.g., a surgical marker pen, scalpel or other sharp instrument to scribe or mark a bone surface) to impart one or more indicating marks on the bone surface to be prepared. The clinician can subsequently perform freehand bone preparation (e.g., cutting) using a tissue removing instrument that follows or traces the indicating mark. FIG. 33 is a perspective view of an example bone preparation template 300 that defines one or more guiding surfaces 302 that can be used to guide a marking instrument.

In any configuration of a bone preparation template, the template may be used to designation bone preparation locations (e.g., one or more cut lines) that can be used by the clinician to prepare one or more bone end. The bone preparation locations can be those discussed above with respect to a cut guide, resulting in removed bone portions and/or joint openings, e.g., as discussed as being generated with a cut guide. Also, the locating features used with the bone preparation template can be those discussed above with respect to a cut guide. A bone preparation template as described herein can be used to prepare any bone or combination of bones, including a first metatarsal and/or one or more lesser metatarsals.

Various examples have been described. These and other examples are within the scope of the following claims.

The invention claimed is:

1. A method for treating metatarsus adductus comprising:
   positioning a cutting guide defining a guide surface over a dorsal side of a second metatarsal and over a dorsal side of a third metatarsal;
   cutting an end of the second metatarsal by at least advancing a cutting tool along the guide surface to remove a portion of an end of the second metatarsal to create an opening between the end of the second metatarsal and an intermediate cuneiform;
   cutting an end of the third metatarsal by at least advancing the cutting tool along the guide surface to remove a portion of an end of the third metatarsal to create an opening between the end of the third metatarsal and a lateral cuneiform;
   moving the second metatarsal and the third metatarsal in at least a transverse plane to close a metatarsus adductus angle; and
   fixating a moved position of the second metatarsal and the third metatarsal.

2. The method of claim 1, wherein moving the second metatarsal and the third metatarsal comprises moving the second metatarsal and the third metatarsal together as a joined bone group.

3. The method of claim 2, wherein moving the second metatarsal and the third metatarsal together as a joined bone group comprises preserving ligamentous attachments between the second metatarsal and the third metatarsal.

4. The method of claim 2, wherein moving the second metatarsal and the third metatarsal together as a joined bone group comprises moving the second metatarsal and the third metatarsal without significantly changing an intermetatarsal angle between the second metatarsal and the third metatarsal.

5. The method of claim 1, wherein moving the second metatarsal and the third metatarsal in at least the transverse plane comprises pivoting the second metatarsal and the third metatarsal in the transverse plane about a medial aspect of the second metatarsal.

6. The method of claim 1, further comprising:
   preparing an end of the intermediate cuneiform; and
   preparing an end of the lateral cuneiform.

7. The method of claim 6, wherein preparing the end of the intermediate cuneiform comprises cutting the intermediate cuneiform, and preparing the end of the lateral cuneiform comprises cutting the end of the lateral cuneiform.

8. The method of claim 1, wherein:
   cutting the end of the second metatarsal to create the opening comprises cutting the end of the second metatarsal to create a wedge-shaped opening; and
   cutting the end of the third metatarsal to create the opening comprises cutting the end of the third metatarsal to create a wedge-shaped opening.

9. The method of claim 8, wherein:
   cutting the end of the second metatarsal to create the wedge-shaped opening comprises making a cut angled in the transverse plane to create a wedge-shaped section of bone, and further comprising, prior to moving the second metatarsal, removing the wedge-shaped section of bone, and
   cutting the end of the third metatarsal to create the wedge-shaped opening comprises making a cut angled in the transverse plane to create a wedge-shaped section of bone, and further comprising, prior to moving the third metatarsal, removing the wedge-shaped section of bone.

10. The method of claim 8, wherein:
    moving the second metatarsal in the transverse plane comprises closing the wedge-shaped opening between the end of the second metatarsal and the intermediate cuneiform; and
    moving the third metatarsal in the transverse plane comprises closing the wedge-shaped opening between the end of the third metatarsal and the lateral cuneiform.

11. The method of claim 1, further comprising, prior to fixating the moved position, compressing the end of the second metatarsal against the end of the intermediate cuneiform and compressing the end of the third metatarsal against the end of the lateral cuneiform.

12. The method of claim 1, further comprising engaging a bone positioning guide with at least one of the second metatarsal and the third metatarsal and a bone other than the second metatarsal and the third metatarsal, wherein moving the second metatarsal and the third metatarsal in the transverse plane comprises engaging the bone positioning guide.

13. The method of claim 12, wherein the bone positioning guide is a compressor, and engaging the bone positioning guide with at least one of the second metatarsal and the third metatarsal comprises attaching the compressor to at least one of:
    the intermediate cuneiform and the second metatarsal, and
    the lateral cuneiform and the third metatarsal.

14. The method of claim 12, wherein the bone positioning guide is engaged with (a) at least one of a medial side of the second metatarsal and a medial side of the third metatarsal and (b) a bone other than the second metatarsal and the third metatarsal.

15. The method of claim 1, wherein moving the second metatarsal and the third metatarsal in at least the transverse plane to close the metatarsus adductus angle further comprises moving a fourth metatarsal and a fifth metatarsal in at least the transverse plane.

16. The method of claim 1, further comprising provisionally fixating a moved position of the second metatarsal and the third metatarsal.

17. The method of claim 16, wherein provisionally fixating the moved position of the second metatarsal and the third metatarsal comprises inserting a pin through the third metatarsal and into the intermediate cuneiform.

18. The method of claim 1, wherein fixating the moved position of the second metatarsal and the third metatarsal comprises:
    applying at least one fixation device across a second tarsal-metatarsal joint between the second metatarsal and the intermediate cuneiform, and
    applying at least one fixation device across a third tarsal-metatarsal joint between the third metatarsal and the lateral cuneiform.

19. The method of claim 18, wherein:
    applying at least one fixation device across the second tarsal-metatarsal joint comprises attaching a first plate or a first staple to the second metatarsal and to the intermediate cuneiform, and
    applying at least one fixation device across the third tarsal-metatarsal joint comprises attaching a second plate or a second staple to the third metatarsal and to the lateral cuneiform.

20. The method of claim 1, further comprising realigning a first metatarsal by at least:
    preparing an end of the first metatarsal;
    preparing an end of a medial cuneiform facing the first metatarsal;
    moving the first metatarsal in at least the transverse plane to close an intermetatarsal angle between the first metatarsal and the second metatarsal; and
    fixating a moved position of the first metatarsal.

21. The method of claim 20, wherein moving the first metatarsal in at least the transverse plane further comprises rotating the first metatarsal in a frontal plane.

22. The method of claim 20, wherein moving the first metatarsal comprises moving the first metatarsal after moving the second metatarsal and the third metatarsal.

23. The method of claim 1, wherein the guide surface comprises a continuous guide surface extending from a medial-most side of the second metatarsal to a lateral-most side of the third metatarsal.

24. The method of claim 1, wherein the guide surface defines a first guide surface, and further comprises a second guide surface parallel to the first guide surface to define a cutting slot between the first guide surface and the second guide surface, wherein advancing the cutting tool along the guide surface comprises advancing the cutting tool in the cutting slot.

25. The method of claim 1, wherein positioning the cutting guide over the dorsal side of the second metatarsal and over the dorsal side of the third metatarsal comprise at least one of:
    inserting a pin associated with the cutting guide into a bone; and
    inserting a spacer associated with the cutting guide between adjacent bones.

26. The method of claim 25, wherein the at least one of the pin and the spacer is separable from the cutting guide, and inserting at least one of the pin and spacer comprises at least one of:
    inserting the pin into the bone and sliding the bone cutting guide onto the pin; and
    inserting the spacer between adjacent bones and sliding the bone cutting guide onto the spacer.

27. The method of claim 25, wherein the cutting guide comprises at least one fixation hole, and further comprising, after sliding the cutting guide onto the at least one of the pin and the spacer, inserting a pin through the at least one fixation hole into an underlying bone to fix a position of the cutting guide.

28. The method of claim 1, wherein the guide surface comprises a metatarsal-side guide surface, and further comprising cutting the end of the intermediate cuneiform and cutting the end of the lateral cuneiform by at least:
    positioning a cuneiform-side guide surface of the cutting guide over a dorsal side of the intermediate cuneiform and over a dorsal side of the lateral cuneiform,
    positioning the metatarsal-side guide surface of the cutting guide over the dorsal side of the second metatarsal and over the dorsal side of the third metatarsal,
    using the cuneiform-side guide surface to advance a cutting tool parallel to the cuneiform-side guide surface to remove a portion of the end of the intermediate cuneiform and to remove a portion of the end of the lateral cuneiform, and
    using the metatarsal-side guide surface to advance the cutting tool parallel to the metatarsal-side guide surface to remove the portion of the end of the second metatarsal and to remove the portion of the end of the third metatarsal.

29. The method of claim 28, wherein the cuneiform-side guide surface comprises a continuous cuneiform-side guide surface extending from a medial-most side of the intermediate cuneiform to a lateral-most side of the lateral cuneiform.

30. The method of claim 28, wherein the metatarsal-side guide surface comprises a continuous metatarsal-side guide surface extending from a medial-most side of the second metatarsal to a lateral-most side of the third metatarsal.

31. The method of claim 28, wherein the metatarsal-side guide surface comprises a first cuneiform-side guide surface extending across the second metatarsal and a second cuneiform-side guide surface extending across the third metatarsal.

32. The method of claim 28, wherein:
    the cuneiform-side guide surface defines a first cuneiform-side guide surface, and further comprising a second cuneiform-side guide surface parallel to the first cuneiform-side guide surface to define a cuneiform-side cutting slot therebetween, wherein using the cuneiform-side guide surface to advance the cutting tool in the plane parallel to the cuneiform-side guide surface comprises advancing the cutting tool in the cuneiform-side guide surface cutting slot, and
    the metatarsal-side guide surface defines a first metatarsal-side guide surface, and further comprising a second metatarsal-side guide surface parallel to the first metatarsal-side guide surface to define a metatarsal-side cutting slot therebetween, wherein using the metatarsal-side guide surface to advance the cutting tool in the plane parallel to the metatarsal-side guide surface comprises advancing the cutting tool in the metatarsal-side guide surface cutting slot.

33. The method of claim 28, wherein an angle between the cuneiform-side guide surface and the metatarsal-side guide surface is fixed.

34. The method of claim 28, wherein an angle between the cuneiform-side guide surface and the metatarsal-side guide surface is adjustable, and further comprising, prior to using the cuneiform-side guide surface and using the metatarsal-side guide surface to advance the cutting tool, setting the angle between the cuneiform-side guide surface and the metatarsal-side guide surface.

35. A method for treating metatarsus adductus comprising:
positioning a cuneiform-side guide surface of a cutting guide over a dorsal side of an intermediate cuneiform and over a dorsal side of a lateral cuneiform;
positioning a metatarsal-side guide surface of the cutting guide over a dorsal side of a second metatarsal opposing the intermediate cuneiform and over a dorsal side of a third metatarsal opposing the lateral cuneiform;
using the cuneiform-side guide surface to advance a cutting tool along the cuneiform-side guide surface to remove a portion of the intermediate cuneiform and to remove a portion of the lateral cuneiform;
using the metatarsal-side guide surface to advance the cutting tool along the metatarsal-side guide surface to remove a portion of the second metatarsal and to remove a portion of the third metatarsal;
moving the second metatarsal and the third metatarsal in a transverse plane to close a metatarsus adductus angle;
provisionally fixating a moved position of the second metatarsal and the third metatarsal; and
permanently fixating the moved position of the second metatarsal and the third metatarsal.

36. A method for treating metatarsus adductus comprising:
cutting an end of at least one of a second metatarsal and an intermediate cuneiform to create an opening between the end of the second metatarsal and the intermediate cuneiform;
cutting an end of at least one of a third metatarsal and a lateral cuneiform to create an opening between the end of the third metatarsal and the lateral cuneiform;
moving the second metatarsal and the third metatarsal in at least a transverse plane to close a metatarsus adductus angle by at least moving the second metatarsal and the third metatarsal together as a joined bone group with preserved ligamentous attachments between the second metatarsal and the third metatarsal; and
fixating a moved position of the second metatarsal and the third metatarsal.

37. The method of claim 36, wherein moving the second metatarsal and the third metatarsal together as a joined bone group comprises moving the second metatarsal and the third metatarsal without significantly changing an intermetatarsal angle between the second metatarsal and the third metatarsal.

38. The method of claim 36, wherein moving the second metatarsal and the third metatarsal in at least the transverse plane comprises pivoting the second metatarsal and the third metatarsal in the transverse plane about a medial aspect of the second metatarsal.

39. The method of claim 36, further comprising:
preparing an end of the other of the second metatarsal and the intermediate cuneiform; and
preparing an end of the other of the third metatarsal and the lateral cuneiform.

40. The method of claim 39, wherein cutting the end of at least one of the second metatarsal and the intermediate cuneiform and preparing the end of the other of the second metatarsal and intermediate cuneiform comprises cutting the end of the second metatarsal and cutting the end of the intermediate cuneiform.

41. The method of claim 39, wherein cutting the end of at least one of the third metatarsal and the lateral cuneiform and preparing the end of the other of the third metatarsal and lateral cuneiform comprises cutting the end of the third metatarsal and cutting the end of the lateral cuneiform.

42. The method of claim 36, wherein:
cutting the end of at least one of the second metatarsal and the intermediate cuneiform to create the opening comprises cutting the end of at least one of the second metatarsal and the intermediate cuneiform to create a wedge-shaped opening; and
cutting the end of at least one of the third metatarsal and the lateral cuneiform to create the opening comprises cutting the end of at least one of the third metatarsal and the lateral cuneiform to create a wedge-shaped opening.

43. The method of claim 42, wherein:
cutting the end of at least one of the second metatarsal and the intermediate cuneiform to create the wedge-shaped opening comprises making a cut angled in the transverse plane to create a wedge-shaped section of bone, and further comprising, prior to moving the second metatarsal, removing the wedge-shaped section of bone, and
cutting the end of at least one of the third metatarsal and the lateral cuneiform to create the wedge-shaped opening comprises making a cut angled in the transverse plane to create a wedge-shaped section of bone, and further comprising, prior to moving the third metatarsal, removing the wedge-shaped section of bone.

44. The method of claim 42, wherein:
moving the second metatarsal in the transverse plane comprises closing the wedge-shaped opening between the end of the second metatarsal and the intermediate cuneiform; and
moving the third metatarsal in the transverse plane comprises closing the wedge-shaped opening between the end of the third metatarsal and the lateral cuneiform.

45. The method of claim 36, further comprising, prior to fixating the moved position, compressing the end of the second metatarsal against the end of the intermediate cuneiform and compressing the end of the third metatarsal against the end of the lateral cuneiform.

46. The method of claim 36, further comprising engaging a bone positioning guide with at least one of the second metatarsal and the third metatarsal and a bone other than the second metatarsal and the third metatarsal, wherein moving the second metatarsal and the third metatarsal in the transverse plane comprises engaging the bone positioning guide.

47. The method of claim 46, wherein the bone positioning guide is a compressor, and engaging the bone positioning guide with at least one of the second metatarsal and the third metatarsal comprises attaching the compressor to at least one of:
the intermediate cuneiform and the second metatarsal, and
the lateral cuneiform and the third metatarsal.

48. The method of claim 46, wherein the bone positioning guide is engaged with (a) at least one of a medial side of the second metatarsal and a medial side of the third metatarsal and (b) a bone other than the second metatarsal and the third metatarsal.

49. The method of claim 36, wherein moving the second metatarsal and the third metatarsal in at least the transverse plane to close the metatarsus adductus angle further comprises moving a fourth metatarsal and a fifth metatarsal in at least the transverse plane.

50. The method of claim 36, further comprising provisionally fixating a moved position of the second metatarsal and the third metatarsal.

51. The method of claim 36, wherein fixating the moved position of the second metatarsal and the third metatarsal comprises:
applying at least one fixation device across a second tarsal-metatarsal joint between the second metatarsal and the intermediate cuneiform, and
applying at least one fixation device across a third tarsal-metatarsal joint between the third metatarsal and the lateral cuneiform.

52. The method of claim 51, wherein:
applying at least one fixation device across the second tarsal-metatarsal joint comprises attaching a first plate or a first staple to the second metatarsal and to the intermediate cuneiform, and
applying at least one fixation device across the third tarsal-metatarsal joint comprises attaching a second plate or a second staple to the third metatarsal and to the lateral cuneiform.

53. The method of claim 36, further comprising:
positioning a cutting guide defining a guide surface over a dorsal side of the second metatarsal and over a dorsal side of the third metatarsal, and using the guide surface to advance a cutting tool along the guide surface to remove a portion of the end of the second metatarsal and to remove a portion of the end of the third metatarsal.

54. The method of claim 53, wherein the guide surface comprises a continuous guide surface extending from a medial-most side of the second metatarsal to a lateral-most side of the third metatarsal.

55. The method of claim 53, wherein the guide surface defines a first guide surface, and further comprises a second guide surface parallel to the first guide surface to define a cutting slot between the first guide surface and the second guide surface, wherein using the guide surface to advance the cutting tool in the plane parallel to the guide surface comprises advancing the cutting tool in the cutting slot.

56. The method of claim 53, wherein positioning the cutting guide over the dorsal side of the second metatarsal and over the dorsal side of the third metatarsal comprise at least one of:
inserting a pin associated with the cutting guide into a bone; and
inserting a spacer associated with the cutting guide between adjacent bones.

57. The method of claim 36, wherein cutting the end of at least one of the second metatarsal and the intermediate cuneiform comprises cutting the end of the second metatarsal and cutting the end of the intermediate cuneiform, and cutting the end of at least one of the third metatarsal and the lateral cuneiform comprises cutting the end of the third metatarsal and cutting the end of the lateral cuneiform, and further comprising:
positioning a cuneiform-side guide surface of a cutting guide over a dorsal side of the intermediate cuneiform and over a dorsal side of the lateral cuneiform,
positioning a metatarsal-side guide surface of the cutting guide over a dorsal side of the second metatarsal and over a dorsal side of the third metatarsal,
using the cuneiform-side guide surface to advance a cutting tool parallel to the cuneiform-side guide surface to remove a portion of the end of the intermediate cuneiform and to remove a portion of the end of the lateral cuneiform, and
using the metatarsal-side guide surface to advance the cutting tool parallel to the metatarsal-side guide surface to remove a portion of the end of the second metatarsal and to remove a portion of the end of the third metatarsal.

\* \* \* \* \*